US011813320B2

(12) United States Patent
Rieder et al.

(10) Patent No.: US 11,813,320 B2
(45) **Date of Patent: *Nov. 14, 2023**

(54) GENETICALLY ENGINEERED FOOT AND MOUTH DISEASE VIRUS AND RELATED PROTEINS, POLYNUCLEOTIDES, COMPOSITIONS, METHODS AND SYSTEMS

(71) Applicants: LAWRENCE LIVERMORE NATIONAL SECURITY, LLC, Livermore, CA (US); THE UNITED STATES OF AMERICA, AS REPRESENTED BY THE SECRETARY OF AGRICULTURE, Washington, DC (US); THE UNIVERSITY OF CONNECTICUT, Farmington, CT (US)

(72) Inventors: Aida E. Rieder, Westbrook, CT (US); Teresa B. De Los Santos, Miller Place, NY (US); Luis L. Rodriguez, Clinton, CT (US); Devendra Rai, Old Saybrook, CT (US); Fayna C. Diaz-San Segundo, Ronkonkoma, NY (US); Paul D. Hoeprich, Pleasanton, CA (US)

(73) Assignees: LAWRENCE LIVERMORE NATIONAL SECURITY, LLC, Livermore, CA (US); THE UNITED STATES OF AMERICA, REPRESENTED BY THE SECRETARY OF AGRICULTURE, Washington, DC (US); THE UNIVERSITY OF CONNECTICUT, Farmington, CT (US)

( * ) Notice: Subject to any disclaimer, the term of this patent is extended or adjusted under 35 U.S.C. 154(b) by 176 days.

This patent is subject to a terminal disclaimer.

(21) Appl. No.: 17/176,989

(22) Filed: Feb. 16, 2021

(65) Prior Publication Data

US 2021/0187095 A1 Jun. 24, 2021

Related U.S. Application Data

(63) Continuation of application No. 15/590,918, filed on May 9, 2017, now Pat. No. 10,953,085.

(51) Int. Cl.
*A61K 39/135* (2006.01)
*C12N 7/00* (2006.01)
(Continued)

(52) U.S. Cl.
CPC ............ *A61K 39/135* (2013.01); *A61K 39/12* (2013.01); *A61P 31/14* (2018.01); *C12N 7/00* (2013.01);
(Continued)

(58) Field of Classification Search
None
See application file for complete search history.

(56) References Cited

U.S. PATENT DOCUMENTS 8,883,729 B2 11/2014 Hoeprich et al.
8,889,623 B2 11/2014 Hoeprich et al.
(Continued)

OTHER PUBLICATIONS

Salguero, Francisco J. et al., "Foot-and-mouth disease virus (FMDV) causes an acute disease that can be lethal for adult laboratory mice," Virology 332, Issue 1, Feb. 5, 2005, pp. 384-396. (13 pages).

*Primary Examiner* — Shanon A. Foley
(74) *Attorney, Agent, or Firm* — Steinfl + Bruno LLP

(57) ABSTRACT

Genetically engineered Foot and Mouth Disease Virus (FMDV) and related engineered proteins and polynucleotides, nanolipoprotein particles, compositions, methods and systems are described. The genetically engineered FMDV is modified by the strategic insertion of a protein tag
(Continued)

into select regions of the FMDV genome which encode viral proteins that are exposed on the surface of the FMDV viral capsid. The inserted protein tag is displayed as a decoration or attachment on the viral capsid surface.

27 Claims, 31 Drawing Sheets

Specification includes a Sequence Listing.

(51) Int. Cl.

| | |
|---|---|
| ***G01N 33/53*** | (2006.01) |
| ***C12Q 1/70*** | (2006.01) |
| ***A61K 39/12*** | (2006.01) |
| ***A61P 31/14*** | (2006.01) |
| *A61K 39/00* | (2006.01) |

(52) U.S. Cl.
CPC ............... *C12Q 1/70* (2013.01); *G01N 33/53* (2013.01); *A61K 2039/5254* (2013.01); *A61K 2039/55555* (2013.01); *A61K 2039/55566* (2013.01); *A61K 2039/55572* (2013.01); *C12N 2770/32122* (2013.01); *C12N 2770/32134* (2013.01); *C12N 2770/32141* (2013.01); *C12N 2770/32162* (2013.01)

(56) References Cited

U.S. PATENT DOCUMENTS

| | | | | |
|---|---|---|---|---|
| 10,953,085 | B2 * | 3/2021 | Rieder ................... | G01N 33/53 |
| 2014/0219918 | A1 * | 8/2014 | Seago .................. | A61K 39/135 424/9.1 |
| 2018/0326038 | A1 | 11/2018 | Rieder et al. | |

* cited by examiner

ACCACCGCTACCGGGGAATCAGCAGACCCGGTCACCACCACCGTGGAGAACTACGGCGGTGAGAC
ACAAATCCAGAGACGTCACCACACGGACATTGGTTTCATCATGGACAGATTTGTGAAGATCCAAAGC
TTGAGCCCAACACATGTCATTGACCTCATGCAGACTCACCAACACGGTCTGGTGGGTGCCTTGCTGC
GTGCAGCCACGTACTACTTTTCTGACCTGGAAATTGTTGTACGGCACGAAGGCAATCTGACCTGGGT
GCCCAACGGCGCCCCTGAATCAGCCCTGTTGAACACCAGCAACCCCACTGCCTACAACAAGGCACC
ATTCACGAGACTCGCTCTCCCCTACACTGCGCCGCACCGTGTGCTGGCAACAGTGTACAACGGGAC
GAGTAAGTATGCTGTGGGTGGTTCAGGCAGAAGAGGCGACATGGGGTCTCTCGCGGCGCGAGTCG
TGAAACAGCTTCCTGCTTCATTTAACTACGGTGCAATCAAGGCGGACGCCATCCACGAACTTCTCGT
GCGCATGAAACGGGCCGAGCTCTACTGCCCCAGACCGCTGTTGGCAATAGAGGTGTCTTCGCAAGA
CAGGCACAAGCAAAAGATCATTGCACCAGCAAAGCAGCACCACCACCACCACCACAAGCAG*CTTCT
GAATTTTGACCTGCTTAAGCTAGCCGGAGACGTTGAGTCCAACCCTGGG* (SEQ ID NO:12).

FIG. 2A

TTATGESADPVTTTVENYGGETQIQRRHHTDIGFIMDRFVKIQSLSPTHVIDLMQTHQHGLVGALLRAATY
YFSDLEIVVRHEGNLTWVPNGAPESALLNTSNPTAYNKAPFTRLALPYTAPHRVLATVYNGTSKYAVGGS
GRRGDMGSLAARVVKQLPASFNYGAIKADAIHELLVRMKRAELYCPRPLLAIEVSSQDRHKQKIIAPAKQ**H
HHHHH**KQ*LLNFDLLKLAGDVESNPG* (SEQ ID NO:13).

FIG. 2B

ACCACCGCTACCGGGGAATCAGCAGACCCGGTCACCACCACCGTGGAGAACTACGGCGGTGAGAC
ACAAATCCAGAGACGTCACCACACGGACATTGGTTTCATCATGGACAGATTTGTGAAGATCCAAAGC
TTGAGCCCAACACATGTCATTGACCTCATGCAGACTCACCAACACGGTCTGGTGGGTGCCTTGCTGC
GTGCAGCCACGTACTACTTTTCTGACCTGGAAATTGTTGTACGGCACGAAGGCAATCTGACCTGGGT
GCCCAACGGCGCCCCTGAATCAGCCCTGTTGAACACCAGCAACCCCACTGCCTACAACAAGGCACC
ATTCACGAGACTCGCTCTCCCCTACACTGCGCCGCACCGTGTGCTGGCAACAGTGTACAACGGGAC
GAGTAAGTATGCTGTGGGTGGTTCAGGCAGAAGAGGCGACATGGGGTCTCTCGCGGCGCGAGTCG
TGAAACAGCTTCCTGCTTCATTTAACTACGGTGCAATCAAGGCCGACGCCATCCACGAACTTCTCGT
GCGCATGAAACGGGCCGAGCTCTACTGCCCCAGACCGCTGTTGGCAATAGAGGTGTCTTCGCAAGA
CAGGCACAAGCAAAAGATCATTGCACCAGCAAAGCACCACCACCACCACCACatcattgcaccagcaaagC
AG*CTTCTGAATTTTGACCTGCTTAAGCTAGCCGGAGACGTTGAGTCCAACCCTGGG* (SEQ ID NO:14).

FIG. 2C

TTATGESADPVTTTVENYGGETQIQRRHHTDIGFIMDRFVKIQSLSPTHVIDLMQTHQHGLVGALLRAATY
YFSDLEIVVRHEGNLTWVPNGAPESALLNTSNPTAYNKAPFTRLALPYTAPHRVLATVYNGTSKYAVGGS
GRRGDMGSLAARVVKQLPASFNYGAIKADAIHELLVRMKRAELYCPRPLLAIEVSSQDRHKQKIIAPAKHH
HHHHiiapakQ*LLNFDLLKLAGDVESNPG* (SEQ ID NO:15].

FIG. 2D

A$_{24}$ FMDV WT
2.0 X 10$^7$

A$_{24}$ FMD P1$_{6H}$
1.1 X 10$^7$

A$_{24}$ FMDV 2A$_{6H}$
0.8 X 10$^7$

| Virus | Cow id # 755 Serum A24FMDV WT Titer $TCID_{50}$/ml | r1 value |
|---|---|---|
| $A_{24}$FMDV WT | 3.15 | 1.00 |
| $A_{24}$FMDV $2A_{6H}$ | 3.45 | 1.99 |
| $A_{24}$FMDV $P1_{6H}$ | 3.00 | 0.7 |

| No. of NiNLP-MPLA bound | A24 FMDV WT | A24 FMDV P16H |
|---|---|---|
| 0 | 124 | 15 |
| 1 | 9 | 23 |
| 2 | 0 | 18 |
| 3 | 0 | 22 |
| 4 | 0 | 14 |
| 5 | 0 | 9 |

Ni-NLP MLPA     −    +    +    +    +
$A_{24}$ FMD $P1_{6H}$ Virus     +    +    +    +    +

Ni-NLP-MLPA-$A_{24}$ + FMD $P1_{6H}$ →
$A_{24}$ FMD $P1_{6H}$ alone →

1    2    3    4    5

SEQUENCE LISTING

<160> NUMBER OF SEQ ID NOS: 50

<210> SEQ ID NO 1
<211> LENGTH: 10871
<212> TYPE: DNA
<213> ORGANISM: Artificial sequence
<220> FEATURE:
<223> OTHER INFORMATION: Foot-and-mouth disease virus

<400> SEQUENCE: 1

```
ttcttgaaag ggggcgctag ggtctcaccc ctagcatgcc aacgacagtc cccgcgttgc      60
actccacact cacgttgtgc gtgcgcggag ctcgatggac tatcgttcac ccacctacag     120
ctggactcac ggcaccgtgt ggccacttgg ctggattgtg cggacgaaca ccgcttgcgc     180
ttctcgcgtg accggttagt actctcacca ccttccgccc acttggttgt tagcgctgtc     240
ttgggcactc ctgttggggg ccgttcgacg ctccgcgagt ttccccgcac ggcaactacg     300
gtgatggggc cgtaccgcgc gggctgatcg cctggtgtgc ttcggctgtc acccgaagcc     360
tacctttcac cccccccccc cccccccccc cccccccccc cccccccccc taagttctac     420
cgtcgttccc gacgtaaagg gatgtaacca caagcttact accgcctttc ccggcgttaa     480
agggatgtaa ccacaagact taccttcacc cggaagtaaa acggcaactt cacacagttt     540
tgcccgtttt catgagaaat gggacgtctg cgcacgaaac gcgccgtcgc ttgaggagga     600
cttgtacaaa cacgatctaa gcaggtttcc ccaactgaca caaaccgtgc aatttgaaac     660
tccgcctggg ctttccaggt ctagaggggt gacactttgt actgtgtttg actccacgtt     720
cgatccactg gcgagtgtta gtaacaacac tgctgcttcg tagcggagca tgacggccgt     780
gggacccccc ccttggtaac aaggacccac ggggccaaaa gccacgtccg aatggacccg     840
tcatgtgtgc aaacccagca cagtagcttt gttgtgaaac tcactttaaa gtgacattga     900
tactggtact caagcactgg tgacaggcta aggatgccct tcaggtaccc cgaggtaaca     960
cgtgacactc gggatctgag aaggggaccg gggcttctat aaaagcgccc ggtttaaaaa    1020
gcttctatgt ctgaataggt gaccggaggc cggcaccttt cttttaatta cactggactt    1080
atgaacacaa ctgattgttt tatcgctttg gtacacgcta tcagagagat cagagcattt    1140
ttcctaccac gagccacagg aaggatggaa ttcacactgc acaacggtga gagaaaagtg    1200
ttctattcta gacccaacaa ccacgacaac tgttggttga acaccatcct tcagctgttc    1260
aggtacgtcg gagaaccctt cttcgactgg gtctatgact cacccgagaa cctcactctc    1320
gaagctatcg agcaactgga ggagctcaca gggttagagt tgcacgaggg cggaccacct    1380
gccctcgtga tctggaacat caaacacctg cttcataccg gcatcggcac cgcctcgcgg    1440
```

-continued

```
cccagcgagg tgtgcatggt ggacggcacg aacatgtgtc ttgctgactt ccacgcaggc   1500
attttcctga aaggacagga acacgctgtg tttgcgtgtg tcacctccaa cgggtggtac   1560
gcgattgacg acgaggactt ttacccatgg acgccggacc cgtccgacgt tttggtgttt   1620
gttccgtacg atcaagagcc acttaacgga gaatggaaaa ccaaggttca gcagaagctc   1680
aagggggccg ggcaatccag tccggcgacc ggctcgcaga accaatctgg caacactggc   1740
agcataatta acaactacta catgcagcaa taccagaact ccatggacac acagttggga   1800
gacaatgcca tcagtggagg ctccaacgag ggctccacgg acacaacttc aacacacaca   1860
accaacactc aaaacaatga ctggttctcg aagctcgcca gttcagcttt taccggtctg   1920
ttcggtgcac tgctcgccga caagaagaca gaggaaacga cacttcttga ggaccgcatc   1980
ctcaccaccc gcaacgggca caccacctcg acgacccaat cgagtgtggg tgtcacacac   2040
gggtactcca cagaggagga ccacgttgct gggcccaaca catcgggcct ggagacgcga   2100
gtggtgcagg cagagagatt ctacaaaaag tacttgtttg actggacaac ggacaaggca   2160
tttggacacc tggaaaagct ggagctcccg tccgaccacc acggtgtctt tggacacttg   2220
gtggactcgt acgcctatat gagaaatggc tgggatgttg aggtgtccgc tgttggcaac   2280
cagttcaacg gcgggtgcct cctggtggcc atggtacctg aatggaagga atttgacaca   2340
cgggagaaat accaactcac ccttttcccg caccagttta ttagccccag aactaacatg   2400
actgcccaca tcacggtccc ctaccttggt gtgaacaggt atgatcagta caagaagcat   2460
aagccctgga cattggttgt catggtcgtg tcgccactta cggtcaacaa cactagtgcg   2520
gcacaaatca aggtctacgc caacatagct ccgacctatg ttcacgtggc cggtgaactc   2580
ccctcgaaag aggggatttt cccggttgca tgtgcggacg gttacggagg attggtgacg   2640
acagacccga agacagctga ccctgcttat ggcaaggtgt acaacccgcc taggactaac   2700
taccctgggc gcttcaccaa cctgttggac gtggccgaag cgtgtcccac tttcctctgc   2760
tttgacgacg ggaaaccgta cgtcaccacg cggacggatg acacccgact tttggccaag   2820
tttgaccttt cccttgccgc aaaacatatg tccaacacat acctgtcagg gattgctcag   2880
tactacacac agtactctgg caccatcaat ttgcatttca tgttcacagg ttccactgat   2940
tcaaaggccc gatacatggt ggcctacatc ccacctgggg tggagacacc accggacaca   3000
cctgaaaggg ctgcccactg cattcacgct gaatgggaca ctggactaaa ctccaaattc   3060
actttctcaa tcccgtacgt atccgccgcg gattacgcgt acacagcgtc tgacacggca   3120
gaaacaatca acgtacaggg atgggtctgc atctaccaaa ttacacacgg gaaggctgaa   3180
aatgacacct tggtcgtgtc ggttagcgcc ggcaaagact ttgagttgcg cctcccgatt   3240
gacccccgcc agcagaccac cgctaccggg gaatcagcag acccggtcac caccaccgtg   3300
gagaactacg gcggtgagac acaaatccag agacgtcacc acacggacat tggtttcatc   3360
atggacagat ttgtgaagat ccaaagcttg agcccaacac atgtcattga cctcatgcag   3420
actcaccaac acggtctggt gggtgccttg ctgcgtgcag ccacgtacta cttttctgac   3480
ctggaaattg ttgtacggca cgaaggcaat ctgacctggg tgcccaacgg cgcccctgaa   3540
tcagccctgt tgaacaccag caaccccact gcctacaaca aggcaccatt cacgagactc   3600
gctctcccct acactgcgcc gcaccgtgtg ctggcaacag tgtacaacgg gacgagtaag   3660
tatgctgtgg gtggttcagg cagaagaggc gacatggggt ctctcgcggc gcgagtcgtg   3720
aaacagcttc ctgcttcatt taactacggt gcaatcaagg ccgacgccat ccacgaactt   3780
ctcgtgcgca tgaaacgggc cgagctctac tgccccagac cgctgttggc aatagaggtg   3840
```

-continued

```
tcttcgcaag acaggcacaa gcaaaagatc attgcaccag caaagcagca ccaccaccac   3900
caccacaagc agcttctgaa ttttgacctg cttaagctag ccggagacgt tgagtccaac   3960
cctgggccct tcttcttctc cgacgttagg tcaaactttt ccaagctggt agacacaatc   4020
aaccagatgc aggaagacat gtccacaaag cacggacctg actttaaccg gttggtgtcc   4080
gcttttgagg agttggccac tggagtgaaa gccatcagga ccggtcttga cgaggccaag   4140
ccctggtaca agcttatcaa gctcctgagc cgcctgtcgt gcatggccgc tgtggcagca   4200
cggtcaaagg acccagtcct tgtggccatc atgctggctg acaccggtct cgagattctg   4260
gacagcacct tcgtcgtgaa gaagatctcc gactcgctct ccagtctctt ccacgtgccg   4320
gcccccgtct tcagtttcgg agccccgatt ctgttagccg ggttggtcaa ggtcgcctcg   4380
agtttcttcc ggtccacgcc cgaagacctt gagagagcag agaaacagct caaagcacgt   4440
gacatcaacg acattttcgc cattctcaag aacggcgagt ggctggtcaa attgatcctt   4500
gccatccgcg actggatcaa ggcatggata gcctcagaag aaaagtttgt caccacgaca   4560
gacttggtac ctagcatcct tgaaaaacag caggacctca acgacccaag caagtacaag   4620
gaagccaagg agtggctcga caacgcgcgc caagcgtgtt tgaagagcgg gaacgtccac   4680
attgccaacc tgtgcaaagt ggtcgccccg gcacccagca ggtcgagacc cgagcccgtg   4740
gtcgtttgcc tccgtggcaa gtccggtcag ggcaagagtt tccttgcaaa cgtgctcgca   4800
caagcaatct ctacccattt cactggcagg accgattcag tttggtactg cccgcctgac   4860
cctgaccact tcgacggtta caaccaacag actgtcgttg tgatggacga tttgggccag   4920
aaccccgacg gcaaagactt caagtacttc gcccaaatgg tttcaacaac ggggttcatc   4980
ccgcccatgg catcgcttga ggataaaggc aaacccttca acagtaaggt catcatagca   5040
accaccaacc tgtactcggg cttcaccccg aggactatgg tgtgccctga tgccctgaac   5100
cggaggtttc actttgacat cgacgtgagc gccaaggacg ggtacaaaat taacaacaaa   5160
ttggacatca tcaaagcact tgaagatact cacaccaacc cagtggcaat gtttcagtac   5220
gactgtgccc ttctcaacgg catggctgtt gaaatgaaga gaatgcaaca agatatgttc   5280
aagcctcaac caccccttca gaacgtgtac caactggttc aagaggtgat tgagcgggtg   5340
gagctccacg agaaggtgtc gagccacccg attttcaaac agatctcaat tccttcccaa   5400
aaatccgtgt tgtacttcct cattgagaaa ggacagcacg aggcagcaat tgaattcttt   5460
gagggcatgg tgcacgactc catcaaggag gagctccggc cgctcatcca acaaacctca   5520
tttgtgaaac gcgcttttaa gcgcctgaag gaaaactttg agattgttgc cctatgtctg   5580
accctcctgg ccaacatagt gatcatgatc cgcgaaactc gcaagagaca gaagatggtg   5640
gacgatgcag tgagtgagta cattgagaga gcaaacatca ccaccgacga caagactctt   5700
gatgaggcgg aaaagaaccc tctggaaacc agcggtgcca gcaccgtcgg cttcagagag   5760
agacctctcc caggccaaaa ggcgcgtaat gacgagaact ccgagcccgc ccagcctgct   5820
gaagagcaac cacaagctga aggaccctac gccgggccgc tagaacgaca gaaacctctg   5880
aaagtgagag ccaagctccc acaacaagag ggaccttacg ctggcccgat ggagagacag   5940
aaaccactga aagtgaaagc aaaagccccg gtcgttaagg aaggacctta cgagggaccg   6000
gtgaagaagc ctgttgcttt gaaagtgaaa gctaagaact tgatcgtcac tgagagtggt   6060
gccccaccga ccgacttgca aaagttggtc atgggcaaca ccaagcccgt tgagctcatc   6120
cttgacggga agacggtagc catttgctgt gctactggag ttttcggcac tgcttacctc   6180
```

-continued

```
gtgcctcgtc atcttttcgc agaaaagtac gacaagatca tgttggacgg cagagccatg   6240

acagatagtg actacagagt gtttgagttt gagattaaag taaaaggaca ggacatgctc   6300

tcagacgctg cgctcatggt gctccaccgt gggaatcgcg tgagagacat cacgaaacac   6360

tttcgtgaca cagcaagaat gaagaaaggc acccccgtcg ttggtgtgat caacaacgcc   6420

gatgtcggga gactgatttt ctctggtgaa gcccttacct acaaggacat tgtagtgtgc   6480

atggatggag acaccatgcc tggctctttt gcctacaaag ccgcaaccaa ggctggttat   6540

tgcggaggag ccgtcctcgc taaggacggg gctgacacgt tcatcgttgg cacccactcc   6600

gctggaggca atggcgttgg atactgctct tgcgtttcca ggtccatgct tctcaagatg   6660

aaggcacacg ttgaccccga accacaccac gaggggttga ttgttgacac cagagatgtg   6720

gaagagcgcg ttcacgtgat gcgcaaaacc aagcttgcac ccaccgttgc gcacggtgtg   6780

ttcaaccctg agttcgggcc tgccgccttg tccaacaagg acccgcgcct gaacgacggt   6840

gttgtcctcg acgaagtcat cttctccaaa cacaagggag acacaaagat gtctgaggaa   6900

gacaaagcgc tgttccgccg ctgtgctgct gactacgcgt cacgcctgca cagcgtgttg   6960

ggtacggcaa atgccccact gagcatctac gaggcaatta aaggcgttga tggactcgac   7020

gcaatggaac cagacaccgc acccggcctc ccctgggcac tccaggggaa gcgccgtggc   7080

gcgctcatcg acttcgagaa cggcactgtt ggacccgaag ttgaggctgc cttgaagctc   7140

atggagaaaa gagaatacaa gtttgcttgc caaaccttcc tgaaggacga gattcgcccg   7200

atggagaaag tacgtgccgg taagactcgc attgtcgacg tcctacctgt tgaacacatc   7260

ctctacacca ggatgatgat tggcagattt tgtgcacaaa tgcactcaaa caacggaccc   7320

caaattggct cggcggtcgg ttgtaaccct gatgttgatt ggcaaagatt tggcacacac   7380

ttcgcccaat acagaaacgt gtgggatgtg gactattcgg ccttcgatgc taaccactgc   7440

agtgacgcca tgaacatcat gtttgaggaa gtgtttcgca cagaattcgg gttccaccca   7500

aacgctgagt ggatcctgaa gactctcgtg aacacggaac acgcctatga gaacaaacgc   7560

atcactgttg aaggcgggat gccatctggt tgttccgcaa caagcatcat caacacaatt   7620

ttgaacaaca tctacgtgct ctacgctttg cgtagacact atgagggagt tgagctggac   7680

acttacacca tgatctctta cggagacgat atcgtggtgg caagtgatta cgatttggac   7740

tttgaggctc tcaagcccca cttcaaatcc cttggtcaaa ccatcactcc agctgacaaa   7800

agcgacaaag gttttgttct tggtcactcc attactgatg tcactttcct caaaagacac   7860

ttccacatgg attatggaac tgggttttac aaacctgtga tggcctcaaa gacccttgag   7920

gctatcctct cctttgcacg ccgtgggacc atacaggaga agttgatctc cgtggcagga   7980

ctcgctgttc actctggacc agacgagtac cggcgtctct tcgagccctt tcaaggcctc   8040

ttcgagattc caagctacag atcactttac ctgcgttggg tgaacgccgt gtgcggcgac   8100

gcataatccc tcagagacta cattggcata ctgtttctga ggcgcgcgac gccgtaggag   8160

tgaaaagcct gaaagggctt ttcccgcttc ctattccaaa aaaaaaaaaa aaaaagcggc   8220

cggcatggtc ccagcctcct cgctggcgcc ggctgggcaa cattccgagg ggaccgtccc   8280

ctcggtaatg gcgaatggga cggggccggg ctgctaacaa agcccgaaag gaagctgagt   8340

tggctgctgc caccgctgag caataactag cataacccct tggggcctct aaacgggtct   8400

tgaggggttt tttgctgaaa ggaggaacta tatccggagg cctatttaaa tggccgcaat   8460

tccggtctcc ctatagtgag tcgtattaat ttcgataagc cattaatgaa tcggccaacg   8520

cgcggggaga ggcggtttgc gtattgggcg ctcttccgct tcctcgctca ctgactcgct   8580
```

-continued

```
gcgctcggtc gttcggctgc ggcgagcggt atcagctcac tcaaaggcgg taatacggtt   8640
atccacagaa tcaggggata acgcaggaaa gaacatgtga gcaaaaggcc agcaaaaggc   8700
caggaaccgt aaaaaggccg cgttgctggc gtttttccat aggctccgcc cccctgacga   8760
gcatcacaaa aatcgacgct caagtcagag gtggcgaaac ccgacaggac tataaagata   8820
ccaggcgttt ccccctggaa gctccctcgt gcgctctcct gttccgaccc tgccgcttac   8880
cggatacctg tccgcctttc tcccttcggg aagcgtggcg ctttctcata gctcacgctg   8940
taggtatctc agttcggtgt aggtcgttcg ctccaagctg ggctgtgtgc acgaaccccc   9000
cgttcagccc gaccgctgcg ccttatccgg taactatcgt cttgagtcca acccggtaag   9060
acacgactta tcgccactgg cagcagccac tggtaacagg attagcagag cgaggtatgt   9120
aggcggtgct acagagttct tgaagtggtg gcctaactac ggctacacta gaaggacagt   9180
atttggtatc tgcgctctgc tgaagccagt taccttcgga aaaagagttg gtagctcttg   9240
atccggcaaa caaaccaccg ctggtagcgg tggttttttt gtttgcaagc agcagattac   9300
gcgcagaaaa aaaggatctc aagaagatcc tttgatcttt tctacggggt ctgacgctca   9360
gtggaacgaa aactcacgtt aagggatttt ggtcatgaga ttatcaaaaa ggatcttcac   9420
ctagatcctt ttaaattaaa aatgaagttt taaatcaatc taaagtatat atgagtaaac   9480
ttggtctgac agttaccaat gcttaatcag tgaggcacct atctcagcga tctgtctatt   9540
tcgttcatcc atagttgcct gactccccgt cgtgtagata actacgatac gggagggctt   9600
accatctggc cccagtgctg caatgatacc gcgagaccca cgctcaccgg ctccagattt   9660
atcagcaata aaccagccag ccggaagggc cgagcgcaga agtggtcctg caactttatc   9720
cgcctccatc cagtctatta attgttgccg ggaagctaga gtaagtagtt cgccagttaa   9780
tagtttgcgc aacgttgttg ccattgctac aggcatcgtg gtgtcacgct cgtcgtttgg   9840
tatggcttca ttcagctccg gttcccaacg atcaaggcga gttacatgat cccccatgtt   9900
gtgcaaaaaa gcggttagct ccttcggtcc tccgatcgtt gtcagaagta agttggccgc   9960
agtgttatca ctcatggtta tggcagcact gcataattct cttactgtca tgccatccgt  10020
aagatgcttt tctgtgactg gtgagtactc aaccaagtca ttctgagaat agtgtatgcg  10080
gcgaccgagt tgctcttgcc cggcgtcaat acgggataat accgcgccac atagcagaac  10140
tttaaaagtg ctcatcattg gaaaacgttc ttcggggcga aaactctcaa ggatcttacc  10200
gctgttgaga tccagttcga tgtaacccac tcgtgcaccc aactgatctt cagcatcttt  10260
tactttcacc agcgtttctg ggtgagcaaa aacaggaagg caaaatgccg caaaaaaggg  10320
aataagggcg acacggaaat gttgaatact catactcttc ctttttcaat tattgaagca  10380
tttatcaggg ttattgtctc atgagcggat acatatttga atgtatttag aaaaataaac  10440
aaataggggt tccgcgcaca tttccccgaa aagtgccacc tgacgtctaa gaaaccatta  10500
ttatcatgac attaacctat aaaaataggc gtatcacgag gccctttcgt ctcgcgcgtt  10560
tcggtgatga cggtgaaaac ctctgacaac ggcgttacca gaaactcaga aggttcgtcc  10620
aaccaaaccg actctgacgg cagtttacga gagagatgat agggtctgct tcagtaagcc  10680
agatgctaca caattaggct tgtacatatt gtcgttagaa cgcggctaca attaatacat  10740
aaccttatgt atcatacaca tacgatttag gtgacactat agaatacaag ctgactctag  10800
catgctaata cgactcacta tagggccttt caactgatga ggccgaaagg ccgaaaaccc  10860
ggtatcccgg g                                                        10871
```

-continued

<210> SEQ ID NO 2
<211> LENGTH: 2313
<212> TYPE: PRT
<213> ORGANISM: Artificial Sequence
<220> FEATURE:
<223> OTHER INFORMATION: Foot-and-mouth disease virus

<400> SEQUENCE: 2

Met Glu Phe Thr Leu His Asn Gly Glu Arg Lys Val Phe Tyr Ser Arg
1 5 10 15

Pro Asn Asn His Asp Asn Cys Trp Leu Asn Thr Ile Leu Gln Leu Phe
20 25 30

Arg Tyr Val Gly Glu Pro Phe Phe Asp Trp Val Tyr Asp Ser Pro Glu
35 40 45

Asn Leu Thr Leu Glu Ala Ile Glu Gln Leu Glu Glu Leu Thr Gly Leu
50 55 60

Glu Leu His Glu Gly Gly Pro Pro Ala Leu Val Ile Trp Asn Ile Lys
65 70 75 80

His Leu Leu His Thr Gly Ile Gly Thr Ala Ser Arg Pro Ser Glu Val
85 90 95

Cys Met Val Asp Gly Thr Asn Met Cys Leu Ala Asp Phe His Ala Gly
100 105 110

Ile Phe Leu Lys Gly Gln Glu His Ala Val Phe Ala Cys Val Thr Ser
115 120 125

Asn Gly Trp Tyr Ala Ile Asp Asp Glu Asp Phe Tyr Pro Trp Thr Pro
130 135 140

Asp Pro Ser Asp Val Leu Val Phe Val Pro Tyr Asp Gln Glu Pro Leu
145 150 155 160

Asn Gly Glu Trp Lys Thr Lys Val Gln Gln Lys Leu Lys Gly Ala Gly
165 170 175

Gln Ser Ser Pro Ala Thr Gly Ser Gln Asn Gln Ser Gly Asn Thr Gly
180 185 190

Ser Ile Ile Asn Asn Tyr Tyr Met Gln Gln Tyr Gln Asn Ser Met Asp
195 200 205

Thr Gln Leu Gly Asp Asn Ala Ile Ser Gly Gly Ser Asn Glu Gly Ser
210 215 220

Thr Asp Thr Thr Ser Thr His Thr Thr Asn Thr Gln Asn Asn Asp Trp
225 230 235 240

Phe Ser Lys Leu Ala Ser Ser Ala Phe Thr Gly Leu Phe Gly Ala Leu
245 250 255

Leu Ala Asp Lys Lys Thr Glu Glu Thr Thr Leu Leu Glu Asp Arg Ile
260 265 270

Leu Thr Thr Arg Asn Gly His Thr Thr Ser Thr Thr Gln Ser Ser Val
275 280 285

Gly Val Thr His Gly Tyr Ser Thr Glu Glu Asp His Val Ala Gly Pro
290 295 300

Asn Thr Ser Gly Leu Glu Thr Arg Val Val Gln Ala Glu Arg Phe Tyr
305 310 315 320

Lys Lys Tyr Leu Phe Asp Trp Thr Thr Asp Lys Ala Phe Gly His Leu
325 330 335

Glu Lys Leu Glu Leu Pro Ser Asp His His Gly Val Phe Gly His Leu
340 345 350

Val Asp Ser Tyr Ala Tyr Met Arg Asn Gly Trp Asp Val Glu Val Ser
355 360 365

-continued

```
Ala Val Gly Asn Gln Phe Asn Gly Gly Cys Leu Leu Val Ala Met Val
    370                 375                 380

Pro Glu Trp Lys Glu Phe Asp Thr Arg Glu Lys Tyr Gln Leu Thr Leu
385                 390                 395                 400

Phe Pro His Gln Phe Ile Ser Pro Arg Thr Asn Met Thr Ala His Ile
                405                 410                 415

Thr Val Pro Tyr Leu Gly Val Asn Arg Tyr Asp Gln Tyr Lys Lys His
            420                 425                 430

Lys Pro Trp Thr Leu Val Val Met Val Val Ser Pro Leu Thr Val Asn
        435                 440                 445

Asn Thr Ser Ala Ala Gln Ile Lys Val Tyr Ala Asn Ile Ala Pro Thr
    450                 455                 460

Tyr Val His Val Ala Gly Glu Leu Pro Ser Lys Glu Gly Ile Phe Pro
465                 470                 475                 480

Val Ala Cys Ala Asp Gly Tyr Gly Gly Leu Val Thr Thr Asp Pro Lys
                485                 490                 495

Thr Ala Asp Pro Ala Tyr Gly Lys Val Tyr Asn Pro Pro Arg Thr Asn
            500                 505                 510

Tyr Pro Gly Arg Phe Thr Asn Leu Leu Asp Val Ala Glu Ala Cys Pro
        515                 520                 525

Thr Phe Leu Cys Phe Asp Asp Gly Lys Pro Tyr Val Thr Thr Arg Thr
    530                 535                 540

Asp Asp Thr Arg Leu Leu Ala Lys Phe Asp Leu Ser Leu Ala Ala Lys
545                 550                 555                 560

His Met Ser Asn Thr Tyr Leu Ser Gly Ile Ala Gln Tyr Tyr Thr Gln
                565                 570                 575

Tyr Ser Gly Thr Ile Asn Leu His Phe Met Phe Thr Gly Ser Thr Asp
            580                 585                 590

Ser Lys Ala Arg Tyr Met Val Ala Tyr Ile Pro Pro Gly Val Glu Thr
        595                 600                 605

Pro Pro Asp Thr Pro Glu Arg Ala Ala His Cys Ile His Ala Glu Trp
    610                 615                 620

Asp Thr Gly Leu Asn Ser Lys Phe Thr Phe Ser Ile Pro Tyr Val Ser
625                 630                 635                 640

Ala Ala Asp Tyr Ala Tyr Thr Ala Ser Asp Thr Ala Glu Thr Ile Asn
                645                 650                 655

Val Gln Gly Trp Val Cys Ile Tyr Gln Ile Thr His Gly Lys Ala Glu
            660                 665                 670

Asn Asp Thr Leu Val Val Ser Val Ser Ala Gly Lys Asp Phe Glu Leu
        675                 680                 685

Arg Leu Pro Ile Asp Pro Arg Gln Gln Thr Thr Ala Thr Gly Glu Ser
    690                 695                 700

Ala Asp Pro Val Thr Thr Thr Val Glu Asn Tyr Gly Gly Glu Thr Gln
705                 710                 715                 720

Ile Gln Arg Arg His His Thr Asp Ile Gly Phe Ile Met Asp Arg Phe
                725                 730                 735

Val Lys Ile Gln Ser Leu Ser Pro Thr His Val Ile Asp Leu Met Gln
            740                 745                 750

Thr His Gln His Gly Leu Val Gly Ala Leu Leu Arg Ala Ala Thr Tyr
        755                 760                 765

Tyr Phe Ser Asp Leu Glu Ile Val Val Arg His Glu Gly Asn Leu Thr
    770                 775                 780

Trp Val Pro Asn Gly Ala Pro Glu Ser Ala Leu Leu Asn Thr Ser Asn
```

-continued

```
785                 790                 795                 800

Pro Thr Ala Tyr Asn Lys Ala Pro Phe Thr Arg Leu Ala Leu Pro Tyr
                805                 810                 815

Thr Ala Pro His Arg Val Leu Ala Thr Val Tyr Asn Gly Thr Ser Lys
            820                 825                 830

Tyr Ala Val Gly Gly Ser Gly Arg Arg Gly Asp Met Gly Ser Leu Ala
        835                 840                 845

Ala Arg Val Val Lys Gln Leu Pro Ala Ser Phe Asn Tyr Gly Ala Ile
    850                 855                 860

Lys Ala Asp Ala Ile His Glu Leu Leu Val Arg Met Lys Arg Ala Glu
865                 870                 875                 880

Leu Tyr Cys Pro Arg Pro Leu Leu Ala Ile Glu Val Ser Ser Gln Asp
                885                 890                 895

Arg His Lys Gln Lys Ile Ile Ala Pro Ala Lys Gln His His His His
            900                 905                 910

His His Lys Gln Leu Leu Asn Phe Asp Leu Leu Lys Leu Ala Gly Asp
        915                 920                 925

Val Glu Ser Asn Pro Gly Pro Phe Phe Phe Ser Asp Val Arg Ser Asn
    930                 935                 940

Phe Ser Lys Leu Val Asp Thr Ile Asn Gln Met Gln Glu Asp Met Ser
945                 950                 955                 960

Thr Lys His Gly Pro Asp Phe Asn Arg Leu Val Ser Ala Phe Glu Glu
                965                 970                 975

Leu Ala Thr Gly Val Lys Ala Ile Arg Thr Gly Leu Asp Glu Ala Lys
            980                 985                 990

Pro Trp Tyr Lys Leu Ile Lys Leu  Leu Ser Arg Leu Ser  Cys Met Ala
        995                 1000                1005

Ala Val  Ala Ala Arg Ser Lys  Asp Pro Val Leu Val  Ala Ile Met
    1010                 1015                 1020

Leu Ala  Asp Thr Gly Leu Glu  Ile Leu Asp Ser Thr  Phe Val Val
    1025                 1030                 1035

Lys Lys  Ile Ser Asp Ser Leu  Ser Ser Leu Phe His  Val Pro Ala
    1040                 1045                 1050

Pro Val  Phe Ser Phe Gly Ala  Pro Ile Leu Leu Ala  Gly Leu Val
    1055                 1060                 1065

Lys Val  Ala Ser Ser Phe Phe  Arg Ser Thr Pro Glu  Asp Leu Glu
    1070                 1075                 1080

Arg Ala  Glu Lys Gln Leu Lys  Ala Arg Asp Ile Asn  Asp Ile Phe
    1085                 1090                 1095

Ala Ile  Leu Lys Asn Gly Glu  Trp Leu Val Lys Leu  Ile Leu Ala
    1100                 1105                 1110

Ile Arg  Asp Trp Ile Lys Ala  Trp Ile Ala Ser Glu  Glu Lys Phe
    1115                 1120                 1125

Val Thr  Thr Thr Asp Leu Val  Pro Ser Ile Leu Glu  Lys Gln Gln
    1130                 1135                 1140

Asp Leu  Asn Asp Pro Ser Lys  Tyr Lys Glu Ala Lys  Glu Trp Leu
    1145                 1150                 1155

Asp Asn  Ala Arg Gln Ala Cys  Leu Lys Ser Gly Asn  Val His Ile
    1160                 1165                 1170

Ala Asn  Leu Cys Lys Val Val  Ala Pro Ala Pro Ser  Arg Ser Arg
    1175                 1180                 1185

Pro Glu  Pro Val Val Val Cys  Leu Arg Gly Lys Ser  Gly Gln Gly
    1190                 1195                 1200
```

-continued

```
Lys Ser  Phe Leu Ala Asn Val  Leu Ala Gln Ala Ile  Ser Thr His
    1205                 1210                 1215

Phe Thr  Gly Arg Thr Asp Ser  Val Trp Tyr Cys Pro  Pro Asp Pro
    1220                 1225                 1230

Asp His  Phe Asp Gly Tyr Asn  Gln Gln Thr Val Val  Val Met Asp
    1235                 1240                 1245

Asp Leu  Gly Gln Asn Pro Asp  Gly Lys Asp Phe Lys  Tyr Phe Ala
    1250                 1255                 1260

Gln Met  Val Ser Thr Thr Gly  Phe Ile Pro Pro Met  Ala Ser Leu
    1265                 1270                 1275

Glu Asp  Lys Gly Lys Pro Phe  Asn Ser Lys Val Ile  Ile Ala Thr
    1280                 1285                 1290

Thr Asn  Leu Tyr Ser Gly Phe  Thr Pro Arg Thr Met  Val Cys Pro
    1295                 1300                 1305

Asp Ala  Leu Asn Arg Arg Phe  His Phe Asp Ile Asp  Val Ser Ala
    1310                 1315                 1320

Lys Asp  Gly Tyr Lys Ile Asn  Asn Lys Leu Asp Ile  Ile Lys Ala
    1325                 1330                 1335

Leu Glu  Asp Thr His Thr Asn  Pro Val Ala Met Phe  Gln Tyr Asp
    1340                 1345                 1350

Cys Ala  Leu Leu Asn Gly Met  Ala Val Glu Met Lys  Arg Met Gln
    1355                 1360                 1365

Gln Asp  Met Phe Lys Pro Gln  Pro Pro Leu Gln Asn  Val Tyr Gln
    1370                 1375                 1380

Leu Val  Gln Glu Val Ile Glu  Arg Val Glu Leu His  Glu Lys Val
    1385                 1390                 1395

Ser Ser  His Pro Ile Phe Lys  Gln Ile Ser Ile Pro  Ser Gln Lys
    1400                 1405                 1410

Ser Val  Leu Tyr Phe Leu Ile  Glu Lys Gly Gln His  Glu Ala Ala
    1415                 1420                 1425

Ile Glu  Phe Phe Glu Gly Met  Val His Asp Ser Ile  Lys Glu Glu
    1430                 1435                 1440

Leu Arg  Pro Leu Ile Gln Gln  Thr Ser Phe Val Lys  Arg Ala Phe
    1445                 1450                 1455

Lys Arg  Leu Lys Glu Asn Phe  Glu Ile Val Ala Leu  Cys Leu Thr
    1460                 1465                 1470

Leu Leu  Ala Asn Ile Val Ile  Met Ile Arg Glu Thr  Arg Lys Arg
    1475                 1480                 1485

Gln Lys  Met Val Asp Asp Ala  Val Ser Glu Tyr Ile  Glu Arg Ala
    1490                 1495                 1500

Asn Ile  Thr Thr Asp Asp Lys  Thr Leu Asp Glu Ala  Glu Lys Asn
    1505                 1510                 1515

Pro Leu  Glu Thr Ser Gly Ala  Ser Thr Val Gly Phe  Arg Glu Arg
    1520                 1525                 1530

Pro Leu  Pro Gly Gln Lys Ala  Arg Asn Asp Glu Asn  Ser Glu Pro
    1535                 1540                 1545

Ala Gln  Pro Ala Glu Glu Gln  Pro Gln Ala Glu Gly  Pro Tyr Ala
    1550                 1555                 1560

Gly Pro  Leu Glu Arg Gln Lys  Pro Leu Lys Val Arg  Ala Lys Leu
    1565                 1570                 1575

Pro Gln  Gln Glu Gly Pro Tyr  Ala Gly Pro Met Glu  Arg Gln Lys
    1580                 1585                 1590
```

-continued

```
Pro Leu  Lys Val Lys Ala Lys  Ala Pro Val Val Lys  Glu Gly Pro
    1595                 1600                 1605

Tyr Glu  Gly Pro Val Lys Lys  Pro Val Ala Leu Lys  Val Lys Ala
    1610                 1615                 1620

Lys Asn  Leu Ile Val Thr Glu  Ser Gly Ala Pro Pro  Thr Asp Leu
    1625                 1630                 1635

Gln Lys  Leu Val Met Gly Asn  Thr Lys Pro Val Glu  Leu Ile Leu
    1640                 1645                 1650

Asp Gly  Lys Thr Val Ala Ile  Cys Cys Ala Thr Gly  Val Phe Gly
    1655                 1660                 1665

Thr Ala  Tyr Leu Val Pro Arg  His Leu Phe Ala Glu  Lys Tyr Asp
    1670                 1675                 1680

Lys Ile  Met Leu Asp Gly Arg  Ala Met Thr Asp Ser  Asp Tyr Arg
    1685                 1690                 1695

Val Phe  Glu Phe Glu Ile Lys  Val Lys Gly Gln Asp  Met Leu Ser
    1700                 1705                 1710

Asp Ala  Ala Leu Met Val Leu  His Arg Gly Asn Arg  Val Arg Asp
    1715                 1720                 1725

Ile Thr  Lys His Phe Arg Asp  Thr Ala Arg Met Lys  Lys Gly Thr
    1730                 1735                 1740

Pro Val  Val Gly Val Ile Asn  Asn Ala Asp Val Gly  Arg Leu Ile
    1745                 1750                 1755

Phe Ser  Gly Glu Ala Leu Thr  Tyr Lys Asp Ile Val  Val Cys Met
    1760                 1765                 1770

Asp Gly  Asp Thr Met Pro Gly  Leu Phe Ala Tyr Lys  Ala Ala Thr
    1775                 1780                 1785

Lys Ala  Gly Tyr Cys Gly Gly  Ala Val Leu Ala Lys  Asp Gly Ala
    1790                 1795                 1800

Asp Thr  Phe Ile Val Gly Thr  His Ser Ala Gly Gly  Asn Gly Val
    1805                 1810                 1815

Gly Tyr  Cys Ser Cys Val Ser  Arg Ser Met Leu Leu  Lys Met Lys
    1820                 1825                 1830

Ala His  Val Asp Pro Glu Pro  His His Glu Gly Leu  Ile Val Asp
    1835                 1840                 1845

Thr Arg  Asp Val Glu Glu Arg  Val His Val Met Arg  Lys Thr Lys
    1850                 1855                 1860

Leu Ala  Pro Thr Val Ala His  Gly Val Phe Asn Pro  Glu Phe Gly
    1865                 1870                 1875

Pro Ala  Ala Leu Ser Asn Lys  Asp Pro Arg Leu Asn  Asp Gly Val
    1880                 1885                 1890

Val Leu  Asp Glu Val Ile Phe  Ser Lys His Lys Gly  Asp Thr Lys
    1895                 1900                 1905

Met Ser  Glu Glu Asp Lys Ala  Leu Phe Arg Arg Cys  Ala Ala Asp
    1910                 1915                 1920

Tyr Ala  Ser Arg Leu His Ser  Val Leu Gly Thr Ala  Asn Ala Pro
    1925                 1930                 1935

Leu Ser  Ile Tyr Glu Ala Ile  Lys Gly Val Asp Gly  Leu Asp Ala
    1940                 1945                 1950

Met Glu  Pro Asp Thr Ala Pro  Gly Leu Pro Trp Ala  Leu Gln Gly
    1955                 1960                 1965

Lys Arg  Arg Gly Ala Leu Ile  Asp Phe Glu Asn Gly  Thr Val Gly
    1970                 1975                 1980

Pro Glu  Val Glu Ala Ala Leu  Lys Leu Met Glu Lys  Arg Glu Tyr
```

```
    1985                1990                1995

Lys Phe  Ala Cys Gln Thr Phe  Leu Lys Asp Glu Ile  Arg Pro Met
    2000                2005                2010

Glu Lys  Val Arg Ala Gly Lys  Thr Arg Ile Val Asp  Val Leu Pro
    2015                2020                2025

Val Glu  His Ile Leu Tyr Thr  Arg Met Met Ile Gly  Arg Phe Cys
    2030                2035                2040

Ala Gln  Met His Ser Asn Asn  Gly Pro Gln Ile Gly  Ser Ala Val
    2045                2050                2055

Gly Cys  Asn Pro Asp Val Asp  Trp Gln Arg Phe Gly  Thr His Phe
    2060                2065                2070

Ala Gln  Tyr Arg Asn Val Trp  Asp Val Asp Tyr Ser  Ala Phe Asp
    2075                2080                2085

Ala Asn  His Cys Ser Asp Ala  Met Asn Ile Met Phe  Glu Glu Val
    2090                2095                2100

Phe Arg  Thr Glu Phe Gly Phe  His Pro Asn Ala Glu  Trp Ile Leu
    2105                2110                2115

Lys Thr  Leu Val Asn Thr Glu  His Ala Tyr Glu Asn  Lys Arg Ile
    2120                2125                2130

Thr Val  Glu Gly Gly Met Pro  Ser Gly Cys Ser Ala  Thr Ser Ile
    2135                2140                2145

Ile Asn  Thr Ile Leu Asn Asn  Ile Tyr Val Leu Tyr  Ala Leu Arg
    2150                2155                2160

Arg His  Tyr Glu Gly Val Glu  Leu Asp Thr Tyr Thr  Met Ile Ser
    2165                2170                2175

Tyr Gly  Asp Asp Ile Val Val  Ala Ser Asp Tyr Asp  Leu Asp Phe
    2180                2185                2190

Glu Ala  Leu Lys Pro His Phe  Lys Ser Leu Gly Gln  Thr Ile Thr
    2195                2200                2205

Pro Ala  Asp Lys Ser Asp Lys  Gly Phe Val Leu Gly  His Ser Ile
    2210                2215                2220

Thr Asp  Val Thr Phe Leu Lys  Arg His Phe His Met  Asp Tyr Gly
    2225                2230                2235

Thr Gly  Phe Tyr Lys Pro Val  Met Ala Ser Lys Thr  Leu Glu Ala
    2240                2245                2250

Ile Leu  Ser Phe Ala Arg Arg  Gly Thr Ile Gln Glu  Lys Leu Ile
    2255                2260                2265

Ser Val  Ala Gly Leu Ala Val  His Ser Gly Pro Asp  Glu Tyr Arg
    2270                2275                2280

Arg Leu  Phe Glu Pro Phe Gln  Gly Leu Phe Glu Ile  Pro Ser Tyr
    2285                2290                2295

Arg Ser  Leu Tyr Leu Arg Trp  Val Asn Ala Val Cys  Gly Asp Ala
    2300                2305                2310
```

<210> SEQ ID NO 3
<211> LENGTH: 10883
<212> TYPE: DNA
<213> ORGANISM: Artificial Sequence
<220> FEATURE:
<223> OTHER INFORMATION: Foot-and-mouth disease virus

<400> SEQUENCE: 3

```
ttgaaagggg gcgctagggt ctcacccta gcatgccaac gacagtcccc gcgttgcact      60

ccacactcac gttgtgcgtg cgcggagctc gatggactat cgttcaccca cctacagctg     120
```

-continued gactcacggc accgtgtggc cacttggctg gattgtgcgg acgaacaccg cttgcgcttc 180
tcgcgtgacc ggttagtact ctcaccacct tccgcccact tggttgttag cgctgtcttg 240
ggcactcctg ttgggggccg ttcgacgctc cgcgagtttc cccgcacggc aactacggtg 300
atggggccgt accgcgcggg ctgatcgcct ggtgtgcttc ggctgtcacc cgaagcctac 360
ctttcacccc cccccccccc cccccccccc cccccccccc cccccctaa gttctaccgt 420
cgttcccgac gtaaagggat gtaaccacaa gcttactacc gcctttcccg gcgttaaagg 480
gatgtaacca caagacttac cttcacccgg aagtaaaacg gcaacttcac acagttttgc 540
ccgttttcat gagaaatggg acgtctgcgc acgaaacgcg ccgtcgcttg aggaggactt 600
gtacaaacac gatctaagca ggtttcccca actgacacaa accgtgcaat ttgaaactcc 660
gcctgggctt tccaggtcta gaggggtgac actttgtact gtgtttgact ccacgttcga 720
tccactggcg agtgttagta acaacactgc tgcttcgtag cggagcatga cggccgtggg 780
acccccccct tggtaacaag gacccacggg gccaaaagcc acgtccgaat ggacccgtca 840
tgtgtgcaaa cccagcacag tagctttgtt gtgaaactca ctttaaagtg acattgatac 900
tggtactcaa gcactggtga caggctaagg atgcccttca ggtaccccga ggtaacacgt 960
gacactcggg atctgagaag gggaccgggg cttctataaa agcgcccggt ttaaaaagct 1020
tctatgtctg aataggtgac cggaggccgg cacctttctt ttaattacac tggacttatg 1080
aacacaactg attgttttat cgctttggta cacgctatca gagagatcag agcatttttc 1140
ctaccacgag ccacaggaag gatggaattc acactgcaca acggtgagag aaaagtgttc 1200
tattctagac ccaacaacca cgacaactgt tggttgaaca ccatccttca gctgttcagg 1260
tacgtcggag aacccttctt cgactgggtc tatgactcac ccgagaacct cactctcgaa 1320
gctatcgagc aactggagga gctcacaggg ttagagttgc acgagggcgg accacctgcc 1380
ctcgtgatct ggaacatcaa acacctgctt cataccggca tcggcaccgc ctcgcggccc 1440
agcgaggtgt gcatggtgga cggcacgaac atgtgtcttg ctgacttcca cgcaggcatt 1500
ttcctgaaag gacaggaaca cgctgtgttt gcgtgtgtca cctccaacgg gtggtacgcg 1560
attgacgacg aggactttta cccatggacg ccggacccgt ccgacgtttt ggtgtttgtt 1620
ccgtacgatc aagagccact taacggagaa tggaaaacca aggttcagca gaagctcaag 1680
ggggccgggc aatccagtcc ggcgaccggc tcgcagaacc aatctggcaa cactggcagc 1740
ataattaaca actactacat gcagcaatac cagaactcca tggacacaca gttgggagac 1800
aatgccatca gtggaggctc caacgagggc tccacggaca caacttcaac acacacaacc 1860
aacactcaaa acaatgactg gttctcgaag ctcgccagtt cagcttttac cggtctgttc 1920
ggtgcactgc tcgccgacaa gaagacagag gaaacgacac ttcttgagga ccgcatcctc 1980
accacccgca acgggcacac cacctcgacg acccaatcga gtgtgggtgt cacacacggg 2040
tactccacag aggaggacca cgttgctggg cccaacacat cgggcctgga gacgcgagtg 2100
gtgcaggcag agagattcta caaaaagtac ttgtttgact ggacaacgga caaggcattt 2160
ggacacctgg aaaagctgga gctcccgtcc gaccaccacg gtgtctttgg acacttggtg 2220
gactcgtacg cctatatgag aaatggctgg gatgttgagg tgtccgctgt tggcaaccag 2280
ttcaacggcg ggtgcctcct ggtggccatg gtacctgaat ggaaggaatt tgacacacgg 2340
gagaaatacc aactcaccct tttcccgcac cagtttatta gccccagaac taacatgact 2400
gcccacatca cggtccccta ccttggtgtg aacaggtatg atcagtacaa gaagcataag 2460
ccctggacat tggttgtcat ggtcgtgtcg ccacttacgg tcaacaacac tagtgcggca 2520

-continued

```
caaatcaagg tctacgccaa catagctccg acctatgttc acgtggccgg tgaactcccc   2580
tcgaaagagg ggattttccc ggttgcatgt gcggacggtt acggaggatt ggtgacgaca   2640
gacccgaaga cagctgaccc tgcttatggc aaggtgtaca acccgcctag gactaactac   2700
cctgggcgct tcaccaacct gttggacgtg gccgaagcgt gtcccacttt cctctgcttt   2760
gacgacggga aaccgtacgt caccacgcgg acggatgaca cccgactttt ggccaagttt   2820
gacctttccc ttgccgcaaa acatatgtcc aacacatacc tgtcagggat tgctcagtac   2880
tacacacagt actctggcac catcaatttg catttcatgt tcacaggttc cactgattca   2940
aaggcccgat acatggtggc ctacatccca cctggggtgg agacaccacc ggacacacct   3000
gaaagggctg cccactgcat tcacgctgaa tgggacactg gactaaactc caaattcact   3060
ttctcaatcc cgtacgtatc cgccgcggat tacgcgtaca cagcgtctga cacggcagaa   3120
acaatcaacg tacagggatg ggtctgcatc taccaaatta cacacgggaa ggctgaaaat   3180
gacaccttgg tcgtgtcggt tagcgccggc aaagactttg agttgcgcct cccgattgac   3240
ccccgccagc agaccaccgc taccggggaa tcagcagacc cggtcaccac caccgtggag   3300
aactacggcg gtgagacaca aatccagaga cgtcaccaca cggacattgg tttcatcatg   3360
gacagatttg tgaagatcca aagcttgagc ccaacacatg tcattgacct catgcagact   3420
caccaacacg gtctggtggg tgccttgctg cgtgcagcca cgtactactt ttctgacctg   3480
gaaattgttg tacggcacga aggcaatctg acctgggtgc ccaacggcgc ccctgaatca   3540
gccctgttga acaccagcaa ccccactgcc tacaacaagg caccattcac gagactcgct   3600
ctcccctaca ctgcgccgca ccgtgtgctg gcaacagtgt acaacgggac gagtaagtat   3660
gctgtgggtg gttcaggcag aagaggcgac atggggtctc tcgcggcgcg agtcgtgaaa   3720
cagcttcctg cttcatttaa ctacggtgca atcaaggccg acgccatcca cgaacttctc   3780
gtgcgcatga aacgggccga gctctactgc cccagaccgc tgttggcaat agaggtgtct   3840
tcgcaagaca ggcacaagca aaagatcatt gcaccagcaa agcaccacca ccaccaccac   3900
atcattgcac cagcaaagca gcttctgaat tttgacctgc ttaagctagc cggagacgtt   3960
gagtccaacc ctgggccctt cttcttctcc gacgttaggt caaacttttc caagctggta   4020
gacacaatca accagatgca ggaagacatg tccacaaagc acggacctga ctttaaccgg   4080
ttggtgtccg cttttgagga gttggccact ggagtgaaag ccatcaggac cggtcttgac   4140
gaggccaagc cctggtacaa gcttatcaag ctcctgagcc gcctgtcgtg catggccgct   4200
gtggcagcac ggtcaaagga cccagtcctt gtggccatca tgctggctga caccggtctc   4260
gagattctgg acagcacctt cgtcgtgaag aagatctccg actcgctctc cagtctcttc   4320
cacgtgccgg cccccgtctt cagtttcgga gccccgattc tgttagccgg gttggtcaag   4380
gtcgcctcga gtttcttccg gtccacgccc gaagaccttg agagagcaga gaaacagctc   4440
aaagcacgtg acatcaacga cattttcgcc attctcaaga acggcgagtg gctggtcaaa   4500
ttgatccttg ccatccgcga ctggatcaag gcatggatag cctcagaaga aaagtttgtc   4560
accacgacag acttggtacc tagcatcctt gaaaaacagc aggacctcaa cgacccaagc   4620
aagtacaagg aagccaagga gtggctcgac aacgcgcgcc aagcgtgttt gaagagcggg   4680
aacgtccaca ttgccaacct gtgcaaagtg gtcgccccgg cacccagcag gtcgagaccc   4740
gagcccgtgg tcgtttgcct ccgtggcaag tccggtcagg gcaagagttt ccttgcaaac   4800
gtgctcgcac aagcaatctc tacccatttc actggcagga ccgattcagt ttggtactgc   4860
```

-continued

```
ccgcctgacc ctgaccactt cgacggttac aaccaacaga ctgtcgttgt gatggacgat   4920
ttgggccaga accccgacgg caaagacttc aagtacttcg cccaaatggt ttcaacaacg   4980
gggttcatcc cgcccatggc atcgcttgag gataaaggca aacccttcaa cagtaaggtc   5040
atcatagcaa ccaccaacct gtactcgggc ttcaccccga ggactatggt gtgccctgat   5100
gccctgaacc ggaggtttca ctttgacatc gacgtgagcg ccaaggacgg gtacaaaatt   5160
aacaacaaat tggacatcat caaagcactt gaagatactc acaccaaccc agtggcaatg   5220
tttcagtacg actgtgccct tctcaacggc atggctgttg aaatgaagag aatgcaacaa   5280
gatatgttca agcctcaacc accccttcag aacgtgtacc aactggttca agaggtgatt   5340
gagcgggtgg agctccacga gaaggtgtcg agccacccga ttttcaaaca gatctcaatt   5400
ccttcccaaa aatccgtgtt gtacttcctc attgagaaag gacagcacga ggcagcaatt   5460
gaattctttg agggcatggt gcacgactcc atcaaggagg agctccggcc gctcatccaa   5520
caaacctcat ttgtgaaacg cgcttttaag cgcctgaagg aaaactttga gattgttgcc   5580
ctatgtctga ccctcctggc caacatagtg atcatgatcc gcgaaactcg caagagacag   5640
aagatggtgg acgatgcagt gagtgagtac attgagagag caaacatcac caccgacgac   5700
aagactcttg atgaggcgga aaagaaccct ctggaaacca gcggtgccag caccgtcggc   5760
ttcagagaga gacctctccc aggccaaaag gcgcgtaatg acgagaactc cgagcccgcc   5820
cagcctgctg aagagcaacc acaagctgaa ggaccctacg ccgggccgct agaacgacag   5880
aaacctctga aagtgagagc caagctccca caacaagagg gaccttacgc tggcccgatg   5940
gagagacaga aaccactgaa agtgaaagca aaagccccgg tcgttaagga aggaccttac   6000
gagggaccgg tgaagaagcc tgttgctttg aaagtgaaag ctaagaactt gatcgtcact   6060
gagagtggtg ccccaccgac cgacttgcaa aagttggtca tgggcaacac caagcccgtt   6120
gagctcatcc ttgacgggaa gacggtagcc atttgctgtg ctactggagt tttcggcact   6180
gcttacctcg tgcctcgtca tcttttcgca gaaaagtacg acaagatcat gttggacggc   6240
agagccatga cagatagtga ctacagagtg tttgagtttg agattaaagt aaaaggacag   6300
gacatgctct cagacgctgc gctcatggtg ctccaccgtg ggaatcgcgt gagagacatc   6360
acgaaacact ttcgtgacac agcaagaatg aagaaaggca cccccgtcgt tggtgtgatc   6420
aacaacgccg atgtcgggag actgattttc tctggtgaag cccttaccta caaggacatt   6480
gtagtgtgca tggatggaga caccatgcct gggctctttg cctacaaagc cgcaaccaag   6540
gctggttatt gcggaggagc cgtcctcgct aaggacgggg ctgacacgtt catcgttggc   6600
acccactccg ctggaggcaa tggcgttgga tactgctctt gcgtttccag gtccatgctt   6660
ctcaagatga aggcacacgt tgaccccgaa ccacaccacg aggggttgat tgttgacacc   6720
agagatgtgg aagagcgcgt tcacgtgatg cgcaaaacca agcttgcacc caccgttgcg   6780
cacggtgtgt tcaaccctga gttcgggcct gccgccttgt ccaacaagga cccgcgcctg   6840
aacgacggtg ttgtcctcga cgaagtcatc ttctccaaac acaagggaga cacaaagatg   6900
tctgaggaag acaaagcgct gttccgccgc tgtgctgctg actacgcgtc acgcctgcac   6960
agcgtgttgg gtacggcaaa tgccccactg agcatctacg aggcaattaa aggcgttgat   7020
ggactcgacg caatggaacc agacaccgca cccggcctcc cctgggcact ccaggggaag   7080
cgccgtggcg cgctcatcga cttcgagaac ggcactgttg gacccgaagt tgaggctgcc   7140
ttgaagctca tggagaaaag agaatacaag tttgcttgcc aaaccttcct gaaggacgag   7200
attcgcccga tggagaaagt acgtgccggt aagactcgca ttgtcgacgt cctacctgtt   7260
```

-continued

```
gaacacatcc tctacaccag gatgatgatt ggcagatttt gtgcacaaat gcactcaaac   7320
aacggacccc aaattggctc ggcggtcggt tgtaaccctg atgttgattg gcaaagattt   7380
ggcacacact tcgcccaata cagaaacgtg tgggatgtgg actattcggc cttcgatgct   7440
aaccactgca gtgacgccat gaacatcatg tttgaggaag tgtttcgcac agaattcggg   7500
ttccacccaa acgctgagtg gatcctgaag actctcgtga acacggaaca cgcctatgag   7560
aacaaacgca tcactgttga aggcgggatg ccatctggtt gttccgcaac aagcatcatc   7620
aacacaattt tgaacaacat ctacgtgctc tacgctttgc gtagacacta tgagggagtt   7680
gagctggaca cttacaccat gatctcttac ggagacgata tcgtggtggc aagtgattac   7740
gatttggact ttgaggctct caagccccac ttcaaatccc ttggtcaaac catcactcca   7800
gctgacaaaa gcgacaaagg ttttgttctt ggtcactcca ttactgatgt cactttcctc   7860
aaaagacact tccacatgga ttatggaact gggttttaca aacctgtgat ggcctcaaag   7920
acccttgagg ctatcctctc ctttgcacgc cgtgggacca tacaggagaa gttgatctcc   7980
gtggcaggac tcgctgttca ctctggacca gacgagtacc ggcgtctctt cgagcccttt   8040
caaggcctct tcgagattcc aagctacaga tcactttacc tgcgttgggt gaacgccgtg   8100
tgcggcgacg cataatccct cagagactac attggcatac tgtttctgag gcgcgcgacg   8160
ccgtaggagt gaaaagcctg aaagggcttt tcccgcttcc tattccaaaa aaaaaaaaaa   8220
aaaagcggcc ggcatggtcc cagcctcctc gctggcgccg gctgggcaac attccgaggg   8280
gaccgtcccc tcggtaatgg cgaatgggac ggggccgggc tgctaacaaa gcccgaaagg   8340
aagctgagtt ggctgctgcc accgctgagc aataactagc ataacccctt ggggcctcta   8400
aacgggtctt gaggggtttt ttgctgaaag gaggaactat atccggaggc ctatttaaat   8460
ggccgcaatt ccggtctccc tatagtgagt cgtattaatt tcgataagcc attaatgaat   8520
cggccaacgc gcggggagag gcggtttgcg tattgggcgc tcttccgctt cctcgctcac   8580
tgactcgctg cgctcggtcg ttcggctgcg gcgagcggta tcagctcact caaaggcggt   8640
aatacggtta tccacagaat caggggataa cgcaggaaag aacatgtgag caaaaggcca   8700
gcaaaaggcc aggaaccgta aaaaggccgc gttgctggcg tttttccata ggctccgccc   8760
ccctgacgag catcacaaaa atcgacgctc aagtcagagg tggcgaaacc cgacaggact   8820
ataaagatac caggcgtttc cccctggaag ctccctcgtg cgctctcctg ttccgaccct   8880
gccgcttacc ggatacctgt ccgcctttct cccttcggga agcgtggcgc tttctcatag   8940
ctcacgctgt aggtatctca gttcggtgta ggtcgttcgc tccaagctgg gctgtgtgca   9000
cgaacccccc gttcagcccg accgctgcgc cttatccggt aactatcgtc ttgagtccaa   9060
cccggtaaga cacgacttat cgccactggc agcagccact ggtaacagga ttagcagagc   9120
gaggtatgta ggcggtgcta cagagttctt gaagtggtgg cctaactacg gctacactag   9180
aaggacagta tttggtatct gcgctctgct gaagccagtt accttcggaa aaagagttgg   9240
tagctcttga tccggcaaac aaaccaccgc tggtagcggt ggtttttttg tttgcaagca   9300
gcagattacg cgcagaaaaa aaggatctca agaagatcct ttgatctttt ctacggggtc   9360
tgacgctcag tggaacgaaa actcacgtta agggattttg gtcatgagat tatcaaaaag   9420
gatcttcacc tagatccttt taaattaaaa atgaagtttt aaatcaatct aaagtatata   9480
tgagtaaact tggtctgaca gttaccaatg cttaatcagt gaggcaccta tctcagcgat   9540
ctgtctattt cgttcatcca tagttgcctg actccccgtc gtgtagataa ctacgatacg   9600
```

```
ggagggctta ccatctggcc ccagtgctgc aatgataccg cgagacccac gctcaccggc   9660

tccagattta tcagcaataa accagccagc cggaagggcc gagcgcagaa gtggtcctgc   9720

aactttatcc gcctccatcc agtctattaa ttgttgccgg gaagctagag taagtagttc   9780

gccagttaat agtttgcgca acgttgttgc cattgctaca ggcatcgtgg tgtcacgctc   9840

gtcgtttggt atggcttcat tcagctccgg ttcccaacga tcaaggcgag ttacatgatc   9900

ccccatgttg tgcaaaaaag cggttagctc cttcggtcct ccgatcgttg tcagaagtaa   9960

gttggccgca gtgttatcac tcatggttat ggcagcactg cataattctc ttactgtcat  10020

gccatccgta agatgctttt ctgtgactgg tgagtactca accaagtcat tctgagaata  10080

gtgtatgcgg cgaccgagtt gctcttgccc ggcgtcaata cgggataata ccgcgccaca  10140

tagcagaact ttaaaagtgc tcatcattgg aaaacgttct tcggggcgaa aactctcaag  10200

gatcttaccg ctgttgagat ccagttcgat gtaacccact cgtgcaccca actgatcttc  10260

agcatctttt actttcacca gcgtttctgg gtgagcaaaa acaggaaggc aaaatgccgc  10320

aaaaaaggga ataagggcga cacggaaatg ttgaatactc atactcttcc tttttcaatt  10380

attgaagcat ttatcagggt tattgtctca tgagcggata catatttgaa tgtatttaga  10440

aaaataaaca aataggggtt ccgcgcacat ttccccgaaa agtgccacct gacgtctaag  10500

aaaccattat tatcatgaca ttaacctata aaaataggcg tatcacgagg ccctttcgtc  10560

tcgcgcgttt cggtgatgac ggtgaaaacc tctgacaacg gcgttaccag aaactcagaa  10620

ggttcgtcca accaaaccga ctctgacggc agtttacgag agagatgata gggtctgctt  10680

cagtaagcca gatgctacac aattaggctt gtacatattg tcgttagaac gcggctacaa  10740

ttaatacata accttatgta tcatacacat acgatttagg tgacactata gaatacaagc  10800

tgactctagc atgctaatac gactcactat agggcctttc aactgatgag gccgaaaggc  10860

cgaaaacccg gtatcccggg ttc                                          10883
```

```
<210> SEQ ID NO 4
<211> LENGTH: 2317
<212> TYPE: PRT
<213> ORGANISM: Artificial Sequence
<220> FEATURE:
<223> OTHER INFORMATION: Foot-and-mouth disease virus

<400> SEQUENCE: 4

Met Glu Phe Thr Leu His Asn Gly Glu Arg Lys Val Phe Tyr Ser Arg
1               5                   10                  15

Pro Asn Asn His Asp Asn Cys Trp Leu Asn Thr Ile Leu Gln Leu Phe
            20                  25                  30

Arg Tyr Val Gly Glu Pro Phe Phe Asp Trp Val Tyr Asp Ser Pro Glu
        35                  40                  45

Asn Leu Thr Leu Glu Ala Ile Glu Gln Leu Glu Glu Leu Thr Gly Leu
    50                  55                  60

Glu Leu His Glu Gly Gly Pro Pro Ala Leu Val Ile Trp Asn Ile Lys
65                  70                  75                  80

His Leu Leu His Thr Gly Ile Gly Thr Ala Ser Arg Pro Ser Glu Val
                85                  90                  95

Cys Met Val Asp Gly Thr Asn Met Cys Leu Ala Asp Phe His Ala Gly
            100                 105                 110

Ile Phe Leu Lys Gly Gln Glu His Ala Val Phe Ala Cys Val Thr Ser
        115                 120                 125

Asn Gly Trp Tyr Ala Ile Asp Asp Glu Asp Phe Tyr Pro Trp Thr Pro
```

-continued

```
    130                 135                 140

Asp Pro Ser Asp Val Leu Val Phe Val Pro Tyr Asp Gln Glu Pro Leu
145                 150                 155                 160

Asn Gly Glu Trp Lys Thr Lys Val Gln Gln Lys Leu Lys Gly Ala Gly
                165                 170                 175

Gln Ser Ser Pro Ala Thr Gly Ser Gln Asn Gln Ser Gly Asn Thr Gly
            180                 185                 190

Ser Ile Ile Asn Asn Tyr Tyr Met Gln Gln Tyr Gln Asn Ser Met Asp
        195                 200                 205

Thr Gln Leu Gly Asp Asn Ala Ile Ser Gly Gly Ser Asn Glu Gly Ser
    210                 215                 220

Thr Asp Thr Thr Ser Thr His Thr Thr Asn Thr Gln Asn Asn Asp Trp
225                 230                 235                 240

Phe Ser Lys Leu Ala Ser Ser Ala Phe Thr Gly Leu Phe Gly Ala Leu
                245                 250                 255

Leu Ala Asp Lys Lys Thr Glu Glu Thr Thr Leu Leu Glu Asp Arg Ile
            260                 265                 270

Leu Thr Thr Arg Asn Gly His Thr Thr Ser Thr Thr Gln Ser Ser Val
        275                 280                 285

Gly Val Thr His Gly Tyr Ser Thr Glu Glu Asp His Val Ala Gly Pro
    290                 295                 300

Asn Thr Ser Gly Leu Glu Thr Arg Val Val Gln Ala Glu Arg Phe Tyr
305                 310                 315                 320

Lys Lys Tyr Leu Phe Asp Trp Thr Thr Asp Lys Ala Phe Gly His Leu
                325                 330                 335

Glu Lys Leu Glu Leu Pro Ser Asp His His Gly Val Phe Gly His Leu
            340                 345                 350

Val Asp Ser Tyr Ala Tyr Met Arg Asn Gly Trp Asp Val Glu Val Ser
        355                 360                 365

Ala Val Gly Asn Gln Phe Asn Gly Gly Cys Leu Leu Val Ala Met Val
    370                 375                 380

Pro Glu Trp Lys Glu Phe Asp Thr Arg Glu Lys Tyr Gln Leu Thr Leu
385                 390                 395                 400

Phe Pro His Gln Phe Ile Ser Pro Arg Thr Asn Met Thr Ala His Ile
                405                 410                 415

Thr Val Pro Tyr Leu Gly Val Asn Arg Tyr Asp Gln Tyr Lys Lys His
            420                 425                 430

Lys Pro Trp Thr Leu Val Val Met Val Val Ser Pro Leu Thr Val Asn
        435                 440                 445

Asn Thr Ser Ala Ala Gln Ile Lys Val Tyr Ala Asn Ile Ala Pro Thr
    450                 455                 460

Tyr Val His Val Ala Gly Glu Leu Pro Ser Lys Glu Gly Ile Phe Pro
465                 470                 475                 480

Val Ala Cys Ala Asp Gly Tyr Gly Gly Leu Val Thr Thr Asp Pro Lys
                485                 490                 495

Thr Ala Asp Pro Ala Tyr Gly Lys Val Tyr Asn Pro Pro Arg Thr Asn
            500                 505                 510

Tyr Pro Gly Arg Phe Thr Asn Leu Leu Asp Val Ala Glu Ala Cys Pro
        515                 520                 525

Thr Phe Leu Cys Phe Asp Asp Gly Lys Pro Tyr Val Thr Thr Arg Thr
    530                 535                 540

Asp Asp Thr Arg Leu Leu Ala Lys Phe Asp Leu Ser Leu Ala Ala Lys
545                 550                 555                 560
```

-continued

```
His Met Ser Asn Thr Tyr Leu Ser Gly Ile Ala Gln Tyr Tyr Thr Gln
                565                 570                 575

Tyr Ser Gly Thr Ile Asn Leu His Phe Met Phe Thr Gly Ser Thr Asp
            580                 585                 590

Ser Lys Ala Arg Tyr Met Val Ala Tyr Ile Pro Pro Gly Val Glu Thr
        595                 600                 605

Pro Pro Asp Thr Pro Glu Arg Ala Ala His Cys Ile His Ala Glu Trp
    610                 615                 620

Asp Thr Gly Leu Asn Ser Lys Phe Thr Phe Ser Ile Pro Tyr Val Ser
625                 630                 635                 640

Ala Ala Asp Tyr Ala Tyr Thr Ala Ser Asp Thr Ala Glu Thr Ile Asn
                645                 650                 655

Val Gln Gly Trp Val Cys Ile Tyr Gln Ile Thr His Gly Lys Ala Glu
            660                 665                 670

Asn Asp Thr Leu Val Val Ser Val Ser Ala Gly Lys Asp Phe Glu Leu
        675                 680                 685

Arg Leu Pro Ile Asp Pro Arg Gln Gln Thr Thr Ala Thr Gly Glu Ser
    690                 695                 700

Ala Asp Pro Val Thr Thr Thr Val Glu Asn Tyr Gly Gly Glu Thr Gln
705                 710                 715                 720

Ile Gln Arg Arg His His Thr Asp Ile Gly Phe Ile Met Asp Arg Phe
                725                 730                 735

Val Lys Ile Gln Ser Leu Ser Pro Thr His Val Ile Asp Leu Met Gln
            740                 745                 750

Thr His Gln His Gly Leu Val Gly Ala Leu Leu Arg Ala Ala Thr Tyr
        755                 760                 765

Tyr Phe Ser Asp Leu Glu Ile Val Val Arg His Glu Gly Asn Leu Thr
    770                 775                 780

Trp Val Pro Asn Gly Ala Pro Glu Ser Ala Leu Leu Asn Thr Ser Asn
785                 790                 795                 800

Pro Thr Ala Tyr Asn Lys Ala Pro Phe Thr Arg Leu Ala Leu Pro Tyr
                805                 810                 815

Thr Ala Pro His Arg Val Leu Ala Thr Val Tyr Asn Gly Thr Ser Lys
            820                 825                 830

Tyr Ala Val Gly Gly Ser Gly Arg Arg Gly Asp Met Gly Ser Leu Ala
        835                 840                 845

Ala Arg Val Val Lys Gln Leu Pro Ala Ser Phe Asn Tyr Gly Ala Ile
    850                 855                 860

Lys Ala Asp Ala Ile His Glu Leu Leu Val Arg Met Lys Arg Ala Glu
865                 870                 875                 880

Leu Tyr Cys Pro Arg Pro Leu Leu Ala Ile Glu Val Ser Ser Gln Asp
                885                 890                 895

Arg His Lys Gln Lys Ile Ile Ala Pro Ala Lys His His His His His
            900                 905                 910

His Ile Ile Ala Pro Ala Lys Gln Leu Leu Asn Phe Asp Leu Leu Lys
        915                 920                 925

Leu Ala Gly Asp Val Glu Ser Asn Pro Gly Pro Phe Phe Phe Ser Asp
    930                 935                 940

Val Arg Ser Asn Phe Ser Lys Leu Val Asp Thr Ile Asn Gln Met Gln
945                 950                 955                 960

Glu Asp Met Ser Thr Lys His Gly Pro Asp Phe Asn Arg Leu Val Ser
                965                 970                 975
```

```
Ala Phe Glu Glu Leu Ala Thr Gly Val Lys Ala Ile Arg Thr Gly Leu
            980                 985                 990

Asp Glu Ala Lys Pro Trp Tyr Lys  Leu Ile Lys Leu Leu  Ser Arg Leu
        995                 1000                1005

Ser Cys  Met Ala Ala Val Ala  Ala Arg Ser Lys Asp  Pro Val Leu
    1010                 1015                 1020

Val Ala  Ile Met Leu Ala Asp  Thr Gly Leu Glu Ile  Leu Asp Ser
    1025                 1030                 1035

Thr Phe  Val Val Lys Lys Ile  Ser Asp Ser Leu Ser  Ser Leu Phe
    1040                 1045                 1050

His Val  Pro Ala Pro Val Phe  Ser Phe Gly Ala Pro  Ile Leu Leu
    1055                 1060                 1065

Ala Gly  Leu Val Lys Val Ala  Ser Ser Phe Phe Arg  Ser Thr Pro
    1070                 1075                 1080

Glu Asp  Leu Glu Arg Ala Glu  Lys Gln Leu Lys Ala  Arg Asp Ile
    1085                 1090                 1095

Asn Asp  Ile Phe Ala Ile Leu  Lys Asn Gly Glu Trp  Leu Val Lys
    1100                 1105                 1110

Leu Ile  Leu Ala Ile Arg Asp  Trp Ile Lys Ala Trp  Ile Ala Ser
    1115                 1120                 1125

Glu Glu  Lys Phe Val Thr Thr  Thr Asp Leu Val Pro  Ser Ile Leu
    1130                 1135                 1140

Glu Lys  Gln Gln Asp Leu Asn  Asp Pro Ser Lys Tyr  Lys Glu Ala
    1145                 1150                 1155

Lys Glu  Trp Leu Asp Asn Ala  Arg Gln Ala Cys Leu  Lys Ser Gly
    1160                 1165                 1170

Asn Val  His Ile Ala Asn Leu  Cys Lys Val Val Ala  Pro Ala Pro
    1175                 1180                 1185

Ser Arg  Ser Arg Pro Glu Pro  Val Val Val Cys Leu  Arg Gly Lys
    1190                 1195                 1200

Ser Gly  Gln Gly Lys Ser Phe  Leu Ala Asn Val Leu  Ala Gln Ala
    1205                 1210                 1215

Ile Ser  Thr His Phe Thr Gly  Arg Thr Asp Ser Val  Trp Tyr Cys
    1220                 1225                 1230

Pro Pro  Asp Pro Asp His Phe  Asp Gly Tyr Asn Gln  Gln Thr Val
    1235                 1240                 1245

Val Val  Met Asp Asp Leu Gly  Gln Asn Pro Asp Gly  Lys Asp Phe
    1250                 1255                 1260

Lys Tyr  Phe Ala Gln Met Val  Ser Thr Thr Gly Phe  Ile Pro Pro
    1265                 1270                 1275

Met Ala  Ser Leu Glu Asp Lys  Gly Lys Pro Phe Asn  Ser Lys Val
    1280                 1285                 1290

Ile Ile  Ala Thr Thr Asn Leu  Tyr Ser Gly Phe Thr  Pro Arg Thr
    1295                 1300                 1305

Met Val  Cys Pro Asp Ala Leu  Asn Arg Arg Phe His  Phe Asp Ile
    1310                 1315                 1320

Asp Val  Ser Ala Lys Asp Gly  Tyr Lys Ile Asn Asn  Lys Leu Asp
    1325                 1330                 1335

Ile Ile  Lys Ala Leu Glu Asp  Thr His Thr Asn Pro  Val Ala Met
    1340                 1345                 1350

Phe Gln  Tyr Asp Cys Ala Leu  Leu Asn Gly Met Ala  Val Glu Met
    1355                 1360                 1365

Lys Arg  Met Gln Gln Asp Met  Phe Lys Pro Gln Pro  Pro Leu Gln
```

```
    1370                1375                1380

Asn Val  Tyr Gln Leu Val Gln  Glu Val Ile Glu Arg  Val Glu Leu
    1385                1390                1395

His Glu  Lys Val Ser Ser His  Pro Ile Phe Lys Gln  Ile Ser Ile
    1400                1405                1410

Pro Ser  Gln Lys Ser Val Leu  Tyr Phe Leu Ile Glu  Lys Gly Gln
    1415                1420                1425

His Glu  Ala Ala Ile Glu Phe  Phe Glu Gly Met Val  His Asp Ser
    1430                1435                1440

Ile Lys  Glu Glu Leu Arg Pro  Leu Ile Gln Gln Thr  Ser Phe Val
    1445                1450                1455

Lys Arg  Ala Phe Lys Arg Leu  Lys Glu Asn Phe Glu  Ile Val Ala
    1460                1465                1470

Leu Cys  Leu Thr Leu Leu Ala  Asn Ile Val Ile Met  Ile Arg Glu
    1475                1480                1485

Thr Arg  Lys Arg Gln Lys Met  Val Asp Asp Ala Val  Ser Glu Tyr
    1490                1495                1500

Ile Glu  Arg Ala Asn Ile Thr  Thr Asp Asp Lys Thr  Leu Asp Glu
    1505                1510                1515

Ala Glu  Lys Asn Pro Leu Glu  Thr Ser Gly Ala Ser  Thr Val Gly
    1520                1525                1530

Phe Arg  Glu Arg Pro Leu Pro  Gly Gln Lys Ala Arg  Asn Asp Glu
    1535                1540                1545

Asn Ser  Glu Pro Ala Gln Pro  Ala Glu Glu Gln Pro  Gln Ala Glu
    1550                1555                1560

Gly Pro  Tyr Ala Gly Pro Leu  Glu Arg Gln Lys Pro  Leu Lys Val
    1565                1570                1575

Arg Ala  Lys Leu Pro Gln Gln  Glu Gly Pro Tyr Ala  Gly Pro Met
    1580                1585                1590

Glu Arg  Gln Lys Pro Leu Lys  Val Lys Ala Lys Ala  Pro Val Val
    1595                1600                1605

Lys Glu  Gly Pro Tyr Glu Gly  Pro Val Lys Lys Pro  Val Ala Leu
    1610                1615                1620

Lys Val  Lys Ala Lys Asn Leu  Ile Val Thr Glu Ser  Gly Ala Pro
    1625                1630                1635

Pro Thr  Asp Leu Gln Lys Leu  Val Met Gly Asn Thr  Lys Pro Val
    1640                1645                1650

Glu Leu  Ile Leu Asp Gly Lys  Thr Val Ala Ile Cys  Cys Ala Thr
    1655                1660                1665

Gly Val  Phe Gly Thr Ala Tyr  Leu Val Pro Arg His  Leu Phe Ala
    1670                1675                1680

Glu Lys  Tyr Asp Lys Ile Met  Leu Asp Gly Arg Ala  Met Thr Asp
    1685                1690                1695

Ser Asp  Tyr Arg Val Phe Glu  Phe Glu Ile Lys Val  Lys Gly Gln
    1700                1705                1710

Asp Met  Leu Ser Asp Ala Ala  Leu Met Val Leu His  Arg Gly Asn
    1715                1720                1725

Arg Val  Arg Asp Ile Thr Lys  His Phe Arg Asp Thr  Ala Arg Met
    1730                1735                1740

Lys Lys  Gly Thr Pro Val Val  Gly Val Ile Asn Asn  Ala Asp Val
    1745                1750                1755

Gly Arg  Leu Ile Phe Ser Gly  Glu Ala Leu Thr Tyr  Lys Asp Ile
    1760                1765                1770
```

-continued

```
Val Val  Cys Met Asp Gly Asp  Thr Met Pro Gly Leu  Phe Ala Tyr
    1775                 1780                 1785

Lys Ala  Ala Thr Lys Ala Gly  Tyr Cys Gly Gly Ala  Val Leu Ala
    1790                 1795                 1800

Lys Asp  Gly Ala Asp Thr Phe  Ile Val Gly Thr His  Ser Ala Gly
    1805                 1810                 1815

Gly Asn  Gly Val Gly Tyr Cys  Ser Cys Val Ser Arg  Ser Met Leu
    1820                 1825                 1830

Leu Lys  Met Lys Ala His Val  Asp Pro Glu Pro His  His Glu Gly
    1835                 1840                 1845

Leu Ile  Val Asp Thr Arg Asp  Val Glu Glu Arg Val  His Val Met
    1850                 1855                 1860

Arg Lys  Thr Lys Leu Ala Pro  Thr Val Ala His Gly  Val Phe Asn
    1865                 1870                 1875

Pro Glu  Phe Gly Pro Ala Ala  Leu Ser Asn Lys Asp  Pro Arg Leu
    1880                 1885                 1890

Asn Asp  Gly Val Val Leu Asp  Glu Val Ile Phe Ser  Lys His Lys
    1895                 1900                 1905

Gly Asp  Thr Lys Met Ser Glu  Glu Asp Lys Ala Leu  Phe Arg Arg
    1910                 1915                 1920

Cys Ala  Ala Asp Tyr Ala Ser  Arg Leu His Ser Val  Leu Gly Thr
    1925                 1930                 1935

Ala Asn  Ala Pro Leu Ser Ile  Tyr Glu Ala Ile Lys  Gly Val Asp
    1940                 1945                 1950

Gly Leu  Asp Ala Met Glu Pro  Asp Thr Ala Pro Gly  Leu Pro Trp
    1955                 1960                 1965

Ala Leu  Gln Gly Lys Arg Arg  Gly Ala Leu Ile Asp  Phe Glu Asn
    1970                 1975                 1980

Gly Thr  Val Gly Pro Glu Val  Glu Ala Ala Leu Lys  Leu Met Glu
    1985                 1990                 1995

Lys Arg  Glu Tyr Lys Phe Ala  Cys Gln Thr Phe Leu  Lys Asp Glu
    2000                 2005                 2010

Ile Arg  Pro Met Glu Lys Val  Arg Ala Gly Lys Thr  Arg Ile Val
    2015                 2020                 2025

Asp Val  Leu Pro Val Glu His  Ile Leu Tyr Thr Arg  Met Met Ile
    2030                 2035                 2040

Gly Arg  Phe Cys Ala Gln Met  His Ser Asn Asn Gly  Pro Gln Ile
    2045                 2050                 2055

Gly Ser  Ala Val Gly Cys Asn  Pro Asp Val Asp Trp  Gln Arg Phe
    2060                 2065                 2070

Gly Thr  His Phe Ala Gln Tyr  Arg Asn Val Trp Asp  Val Asp Tyr
    2075                 2080                 2085

Ser Ala  Phe Asp Ala Asn His  Cys Ser Asp Ala Met  Asn Ile Met
    2090                 2095                 2100

Phe Glu  Glu Val Phe Arg Thr  Glu Phe Gly Phe His  Pro Asn Ala
    2105                 2110                 2115

Glu Trp  Ile Leu Lys Thr Leu  Val Asn Thr Glu His  Ala Tyr Glu
    2120                 2125                 2130

Asn Lys  Arg Ile Thr Val Glu  Gly Gly Met Pro Ser  Gly Cys Ser
    2135                 2140                 2145

Ala Thr  Ser Ile Ile Asn Thr  Ile Leu Asn Asn Ile  Tyr Val Leu
    2150                 2155                 2160
```

```
Tyr Ala  Leu Arg Arg His Tyr  Glu Gly Val Glu Leu  Asp Thr Tyr
    2165                 2170                 2175

Thr Met  Ile Ser Tyr Gly Asp  Asp Ile Val Val Ala  Ser Asp Tyr
    2180                 2185                 2190

Asp Leu  Asp Phe Glu Ala Leu  Lys Pro His Phe Lys  Ser Leu Gly
    2195                 2200                 2205

Gln Thr  Ile Thr Pro Ala Asp  Lys Ser Asp Lys Gly  Phe Val Leu
    2210                 2215                 2220

Gly His  Ser Ile Thr Asp Val  Thr Phe Leu Lys Arg  His Phe His
    2225                 2230                 2235

Met Asp  Tyr Gly Thr Gly Phe  Tyr Lys Pro Val Met  Ala Ser Lys
    2240                 2245                 2250

Thr Leu  Glu Ala Ile Leu Ser  Phe Ala Arg Arg Gly  Thr Ile Gln
    2255                 2260                 2265

Glu Lys  Leu Ile Ser Val Ala  Gly Leu Ala Val His  Ser Gly Pro
    2270                 2275                 2280

Asp Glu  Tyr Arg Arg Leu Phe  Glu Pro Phe Gln Gly  Leu Phe Glu
    2285                 2290                 2295

Ile Pro  Ser Tyr Arg Ser Leu  Tyr Leu Arg Trp Val  Asn Ala Val
    2300                 2305                 2310

Cys Gly  Asp Ala
    2315
```

<210> SEQ ID NO 5
<211> LENGTH: 21
<212> TYPE: DNA
<213> ORGANISM: Artificial Sequence
<220> FEATURE:
<223> OTHER INFORMATION: P2345_For infusion SacII

<400> SEQUENCE: 5
tcccgtacgt atccgccgcg g 21

<210> SEQ ID NO 6
<211> LENGTH: 21
<212> TYPE: DNA
<213> ORGANISM: Artificial Sequence
<220> FEATURE:
<223> OTHER INFORMATION: P2346_Rev infusion nhe

<400> SEQUENCE: 6
gactcaacgt ctccggctag c 21

<210> SEQ ID NO 7
<211> LENGTH: 21
<212> TYPE: DNA
<213> ORGANISM: Artificial Sequence
<220> FEATURE:
<223> OTHER INFORMATION: P2347_Rev infusion mfe

<400> SEQUENCE: 7
tgccctcaaa gaattcaatt g 21

<210> SEQ ID NO 8
<211> LENGTH: 39
<212> TYPE: DNA
<213> ORGANISM: Artificial Sequence
<220> FEATURE:
<223> OTHER INFORMATION: P2289_VP16H-KQ Forward primer

<400> SEQUENCE: 8

-continued caccaccacc accaccacaa gcagcttctg aattttgac 39

<210> SEQ ID NO 9
<211> LENGTH: 40
<212> TYPE: DNA
<213> ORGANISM: Artificial Sequence
<220> FEATURE:
<223> OTHER INFORMATION: P2290_VP16H-KQ Reverse primer

<400> SEQUENCE: 9
gtggtggtgg tggtggtgct gctttgctgg tgcaatgatc 40

<210> SEQ ID NO 10
<211> LENGTH: 57
<212> TYPE: DNA
<213> ORGANISM: Artificial Sequence
<220> FEATURE:
<223> OTHER INFORMATION: P2350_6H insert jun repeat for

<400> SEQUENCE: 10
caccaccacc accaccacat cattgcacca gcaaagcagc ttctgaattt tgacctg 57

<210> SEQ ID NO 11
<211> LENGTH: 37
<212> TYPE: DNA
<213> ORGANISM: Artificial Sequence
<220> FEATURE:
<223> OTHER INFORMATION: P2351_6H insert jun repeat rev

<400> SEQUENCE: 11
gtggtggtgg tggtggtgct ttgctggtgc aatgatc 37

<210> SEQ ID NO 12
<211> LENGTH: 711
<212> TYPE: DNA
<213> ORGANISM: Artificial Sequence
<220> FEATURE:
<223> OTHER INFORMATION: A24FMDV 2A6H

<400> SEQUENCE: 12
accaccgcta ccggggaatc agcagacccg gtcaccacca ccgtggagaa ctacggcggt 60
gagacacaaa tccagagacg tcaccacacg gacattggtt tcatcatgga cagatttgtg 120
aagatccaaa gcttgagccc aacacatgtc attgacctca tgcagactca ccaacacggt 180
ctggtgggtg ccttgctgcg tgcagccacg tactactttt ctgacctgga aattgttgta 240
cggcacgaag gcaatctgac ctgggtgccc aacggcgccc ctgaatcagc cctgttgaac 300
accagcaacc ccactgccta caacaaggca ccattcacga gactcgctct cccctacact 360
gcgccgcacc gtgtgctggc aacagtgtac aacgggacga gtaagtatgc tgtgggtggt 420
tcaggcagaa gaggcgacat ggggtctctc gcggcgcgag tcgtgaaaca gcttcctgct 480
tcatttaact acggtgcaat caaggcggac gccatccacg aacttctcgt gcgcatgaaa 540
cgggccgagc tctactgccc cagaccgctg ttggcaatag aggtgtcttc gcaagacagg 600
cacaagcaaa agatcattgc accagcaaag cagcaccacc accaccacca caagcagctt 660
ctgaattttg acctgcttaa gctagccgga gacgttgagt ccaaccctgg g 711

<210> SEQ ID NO 13
<211> LENGTH: 237
<212> TYPE: PRT
<213> ORGANISM: Artificial Sequence
<220> FEATURE:
<223> OTHER INFORMATION: A24FMDV 2A6H

<400> SEQUENCE: 13

Thr Thr Ala Thr Gly Glu Ser Ala Asp Pro Val Thr Thr Thr Val Glu
1 5 10 15

Asn Tyr Gly Gly Glu Thr Gln Ile Gln Arg Arg His His Thr Asp Ile
20 25 30

Gly Phe Ile Met Asp Arg Phe Val Lys Ile Gln Ser Leu Ser Pro Thr
35 40 45

His Val Ile Asp Leu Met Gln Thr His Gln His Gly Leu Val Gly Ala
50 55 60

Leu Leu Arg Ala Ala Thr Tyr Tyr Phe Ser Asp Leu Glu Ile Val Val
65 70 75 80

Arg His Glu Gly Asn Leu Thr Trp Val Pro Asn Gly Ala Pro Glu Ser
85 90 95

Ala Leu Leu Asn Thr Ser Asn Pro Thr Ala Tyr Asn Lys Ala Pro Phe
100 105 110

Thr Arg Leu Ala Leu Pro Tyr Thr Ala Pro His Arg Val Leu Ala Thr
115 120 125

Val Tyr Asn Gly Thr Ser Lys Tyr Ala Val Gly Gly Ser Gly Arg Arg
130 135 140

Gly Asp Met Gly Ser Leu Ala Ala Arg Val Val Lys Gln Leu Pro Ala
145 150 155 160

Ser Phe Asn Tyr Gly Ala Ile Lys Ala Asp Ala Ile His Glu Leu Leu
165 170 175

Val Arg Met Lys Arg Ala Glu Leu Tyr Cys Pro Arg Pro Leu Leu Ala
180 185 190

Ile Glu Val Ser Ser Gln Asp Arg His Lys Gln Lys Ile Ile Ala Pro
195 200 205

Ala Lys Gln His His His His His His Lys Gln Leu Leu Asn Phe Asp
210 215 220

Leu Leu Lys Leu Ala Gly Asp Val Glu Ser Asn Pro Gly
225 230 235

<210> SEQ ID NO 14
<211> LENGTH: 723
<212> TYPE: DNA
<213> ORGANISM: Artificial Sequence
<220> FEATURE:
<223> OTHER INFORMATION: A24FMDV P16H

<400> SEQUENCE: 14
accaccgcta ccggggaatc agcagacccg gtcaccacca ccgtggagaa ctacggcggt 60
gagacacaaa tccagagacg tcaccacacg gacattggtt tcatcatgga cagatttgtg 120
aagatccaaa gcttgagccc aacacatgtc attgacctca tgcagactca ccaacacggt 180
ctggtgggtg ccttgctgcg tgcagccacg tactactttt ctgacctgga aattgttgta 240
cggcacgaag gcaatctgac ctgggtgccc aacggcgccc ctgaatcagc cctgttgaac 300
accagcaacc ccactgccta caacaaggca ccattcacga gactcgctct cccctacact 360
gcgccgcacc gtgtgctggc aacagtgtac aacgggacga gtaagtatgc tgtgggtggt 420
tcaggcagaa gaggcgacat ggggtctctc gcggcgcgag tcgtgaaaca gcttcctgct 480
tcatttaact acggtgcaat caaggccgac gccatccacg aacttctcgt gcgcatgaaa 540
cgggccgagc tctactgccc cagaccgctg ttggcaatag aggtgtcttc gcaagacagg 600
cacaagcaaa agatcattgc accagcaaag caccaccacc accaccacat cattgcacca 660
gcaaagcagc ttctgaattt tgacctgctt aagctagccg gagacgttga gtccaaccct 720
ggg 723

<210> SEQ ID NO 15
<211> LENGTH: 241
<212> TYPE: PRT
<213> ORGANISM: Artificial Sequence
<220> FEATURE:
<223> OTHER INFORMATION: A24FMDV P16H

<400> SEQUENCE: 15

Thr Thr Ala Thr Gly Glu Ser Ala Asp Pro Val Thr Thr Thr Val Glu
1 5 10 15

Asn Tyr Gly Gly Glu Thr Gln Ile Gln Arg Arg His His Thr Asp Ile
20 25 30

Gly Phe Ile Met Asp Arg Phe Val Lys Ile Gln Ser Leu Ser Pro Thr
35 40 45

His Val Ile Asp Leu Met Gln Thr His Gln His Gly Leu Val Gly Ala
50 55 60

Leu Leu Arg Ala Ala Thr Tyr Tyr Phe Ser Asp Leu Glu Ile Val Val
65 70 75 80

Arg His Glu Gly Asn Leu Thr Trp Val Pro Asn Gly Ala Pro Glu Ser
85 90 95

Ala Leu Leu Asn Thr Ser Asn Pro Thr Ala Tyr Asn Lys Ala Pro Phe
100 105 110

Thr Arg Leu Ala Leu Pro Tyr Thr Ala Pro His Arg Val Leu Ala Thr
115 120 125

Val Tyr Asn Gly Thr Ser Lys Tyr Ala Val Gly Gly Ser Gly Arg Arg
130 135 140

Gly Asp Met Gly Ser Leu Ala Ala Arg Val Val Lys Gln Leu Pro Ala
145 150 155 160

Ser Phe Asn Tyr Gly Ala Ile Lys Ala Asp Ala Ile His Glu Leu Leu
165 170 175

Val Arg Met Lys Arg Ala Glu Leu Tyr Cys Pro Arg Pro Leu Leu Ala
180 185 190

Ile Glu Val Ser Ser Gln Asp Arg His Lys Gln Lys Ile Ile Ala Pro
195 200 205

Ala Lys His His His His His His Ile Ile Ala Pro Ala Lys Gln Leu
210 215 220

Leu Asn Phe Asp Leu Leu Lys Leu Ala Gly Asp Val Glu Ser Asn Pro
225 230 235 240

Gly

<210> SEQ ID NO 16
<211> LENGTH: 8
<212> TYPE: PRT
<213> ORGANISM: Artificial Sequence
<220> FEATURE:
<223> OTHER INFORMATION: His tag

<400> SEQUENCE: 16

His His His His His His Lys Gln
1 5

<210> SEQ ID NO 17
<211> LENGTH: 12
<212> TYPE: PRT

<213> ORGANISM: Artificial Sequence
<220> FEATURE:
<223> OTHER INFORMATION: His tag

<400> SEQUENCE: 17

His His His His His His Ile Ile Ala Pro Ala Lys
1 5 10

<210> SEQ ID NO 18
<211> LENGTH: 15
<212> TYPE: PRT
<213> ORGANISM: Artificial Sequence
<220> FEATURE:
<223> OTHER INFORMATION: AviTag

<400> SEQUENCE: 18

Gly Leu Asn Asp Ile Phe Glu Ala Gln Lys Ile Glu Trp His Glu
1 5 10 15

<210> SEQ ID NO 19
<211> LENGTH: 26
<212> TYPE: PRT
<213> ORGANISM: Artificial Sequence
<220> FEATURE:
<223> OTHER INFORMATION: Calmodulin-tag

<400> SEQUENCE: 19

Lys Arg Arg Trp Lys Lys Asn Phe Ile Ala Val Ser Ala Ala Asn Arg
1 5 10 15

Phe Lys Lys Ile Ser Ser Ser Gly Ala Leu
20 25

<210> SEQ ID NO 20
<211> LENGTH: 6
<212> TYPE: PRT
<213> ORGANISM: Artificial Sequence
<220> FEATURE:
<223> OTHER INFORMATION: polyglutamate tag

<400> SEQUENCE: 20

Glu Glu Glu Glu Glu Glu
1 5

<210> SEQ ID NO 21
<211> LENGTH: 13
<212> TYPE: PRT
<213> ORGANISM: Artificial Sequence
<220> FEATURE:
<223> OTHER INFORMATION: E-tag

<400> SEQUENCE: 21

Gly Ala Pro Val Pro Tyr Pro Asp Pro Leu Glu Pro Arg
1 5 10

<210> SEQ ID NO 22
<211> LENGTH: 8
<212> TYPE: PRT
<213> ORGANISM: Artificial Sequence
<220> FEATURE:
<223> OTHER INFORMATION: FLAG-tag

<400> SEQUENCE: 22

Asp Tyr Lys Asp Asp Asp Asp Lys
1 5

<210> SEQ ID NO 23

<211> LENGTH: 9
<212> TYPE: PRT
<213> ORGANISM: Artificial Sequence
<220> FEATURE:
<223> OTHER INFORMATION: HA-tag

<400> SEQUENCE: 23

Tyr Pro Tyr Asp Val Pro Asp Tyr Ala
1               5

<210> SEQ ID NO 24
<211> LENGTH: 6
<212> TYPE: PRT
<213> ORGANISM: Artificial Sequence
<220> FEATURE:
<223> OTHER INFORMATION: His-tag

<400> SEQUENCE: 24

His His His His His His
1               5

<210> SEQ ID NO 25
<211> LENGTH: 10
<212> TYPE: PRT
<213> ORGANISM: Artificial Sequence
<220> FEATURE:
<223> OTHER INFORMATION: Myc-tag

<400> SEQUENCE: 25

Glu Gln Lys Leu Ile Ser Glu Glu Asp Leu
1               5                   10

<210> SEQ ID NO 26
<211> LENGTH: 18
<212> TYPE: PRT
<213> ORGANISM: Artificial Sequence
<220> FEATURE:
<223> OTHER INFORMATION: NE-tag

<400> SEQUENCE: 26

Thr Lys Glu Asn Pro Arg Ser Asn Gln Glu Glu Ser Tyr Asp Asp Asn
1               5                   10                  15

Glu Ser

<210> SEQ ID NO 27
<211> LENGTH: 15
<212> TYPE: PRT
<213> ORGANISM: Artificial Sequence
<220> FEATURE:
<223> OTHER INFORMATION: S-tag

<400> SEQUENCE: 27

Lys Glu Thr Ala Ala Ala Lys Phe Glu Arg Gln His Met Asp Ser
1               5                   10                  15

<210> SEQ ID NO 28
<211> LENGTH: 38
<212> TYPE: PRT
<213> ORGANISM: Artificial Sequence
<220> FEATURE:
<223> OTHER INFORMATION: SBP-tag

<400> SEQUENCE: 28

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro

```
            20                  25                  30

Gln Gly Gln Arg Glu Pro
        35


<210> SEQ ID NO 29
<211> LENGTH: 13
<212> TYPE: PRT
<213> ORGANISM: Artificial Sequence
<220> FEATURE:
<223> OTHER INFORMATION: Softag 1

<400> SEQUENCE: 29

Ser Leu Ala Glu Leu Leu Asn Ala Gly Leu Gly Gly Ser
1               5                   10


<210> SEQ ID NO 30
<211> LENGTH: 8
<212> TYPE: PRT
<213> ORGANISM: Artificial Sequence
<220> FEATURE:
<223> OTHER INFORMATION: Softag 3

<400> SEQUENCE: 30

Thr Gln Asp Pro Ser Arg Val Gly
1               5


<210> SEQ ID NO 31
<211> LENGTH: 8
<212> TYPE: PRT
<213> ORGANISM: Artificial Sequence
<220> FEATURE:
<223> OTHER INFORMATION: Strep-tag

<400> SEQUENCE: 31

Trp Ser His Pro Gln Phe Glu Lys
1               5


<210> SEQ ID NO 32
<211> LENGTH: 6
<212> TYPE: PRT
<213> ORGANISM: Artificial Sequence
<220> FEATURE:
<223> OTHER INFORMATION: TC tag

<400> SEQUENCE: 32

Cys Cys Pro Gly Cys Cys
1               5


<210> SEQ ID NO 33
<211> LENGTH: 14
<212> TYPE: PRT
<213> ORGANISM: Artificial Sequence
<220> FEATURE:
<223> OTHER INFORMATION: V5 tag

<400> SEQUENCE: 33

Gly Lys Pro Ile Pro Asn Pro Leu Leu Gly Leu Asp Ser Thr
1               5                   10


<210> SEQ ID NO 34
<211> LENGTH: 11
<212> TYPE: PRT
<213> ORGANISM: Artificial Sequence
<220> FEATURE:
<223> OTHER INFORMATION: VSV-tag

<400> SEQUENCE: 34
```

Tyr Thr Asp Ile Glu Met Asn Arg Leu Gly Lys
1 5 10

<210> SEQ ID NO 35
<211> LENGTH: 8
<212> TYPE: PRT
<213> ORGANISM: Artificial Sequence
<220> FEATURE:
<223> OTHER INFORMATION: Xpress tag

<400> SEQUENCE: 35

Asp Leu Tyr Asp Asp Asp Asp Lys
1 5

<210> SEQ ID NO 36
<211> LENGTH: 16
<212> TYPE: PRT
<213> ORGANISM: Artificial Sequence
<220> FEATURE:
<223> OTHER INFORMATION: Isopeptag

<400> SEQUENCE: 36

Thr Asp Lys Asp Met Thr Ile Thr Phe Thr Asn Lys Lys Asp Ala Glu
1 5 10 15

<210> SEQ ID NO 37
<211> LENGTH: 13
<212> TYPE: PRT
<213> ORGANISM: Artificial Sequence
<220> FEATURE:
<223> OTHER INFORMATION: SpyTag

<400> SEQUENCE: 37

Ala His Ile Val Met Val Asp Ala Tyr Lys Pro Thr Lys
1 5 10

<210> SEQ ID NO 38
<211> LENGTH: 12
<212> TYPE: PRT
<213> ORGANISM: Artificial Sequence
<220> FEATURE:
<223> OTHER INFORMATION: SnoopTag

<400> SEQUENCE: 38

Lys Leu Gly Asp Ile Glu Phe Ile Lys Val Asn Lys
1 5 10

<210> SEQ ID NO 39
<211> LENGTH: 7
<212> TYPE: PRT
<213> ORGANISM: Artificial Sequence
<220> FEATURE:
<223> OTHER INFORMATION: Foot-and-mouth disease virus

<400> SEQUENCE: 39

Ile Ile Ala Pro Ala Lys Gln
1 5

<210> SEQ ID NO 40
<211> LENGTH: 10
<212> TYPE: PRT
<213> ORGANISM: Artificial Sequence
<220> FEATURE:
<223> OTHER INFORMATION: Foot-and-mouth disease virus

<400> SEQUENCE: 40

-continued

Pro Ala Lys Gln Leu Leu Asn Phe Asp Leu
1               5                   10

<210> SEQ ID NO 41
<211> LENGTH: 22
<212> TYPE: PRT
<213> ORGANISM: Artificial Sequence
<220> FEATURE:
<223> OTHER INFORMATION: Foot-and-mouth disease virus

<400> SEQUENCE: 41

Leu Leu Ala Ile Glu Val Ser Ser Gln Asp Arg His Lys Gln Lys Ile
1               5                   10                  15

Ile Ala Pro Ala Lys Gln
            20

<210> SEQ ID NO 42
<211> LENGTH: 22
<212> TYPE: PRT
<213> ORGANISM: Artificial Sequence
<220> FEATURE:
<223> OTHER INFORMATION: Foot-and-mouth disease virus

<400> SEQUENCE: 42

Leu Leu Ala Ile Glu Val Ser His His His His His Lys Gln Lys Ile
1               5                   10                  15

Ile Ala Pro Ala Lys Gln
            20

<210> SEQ ID NO 43
<211> LENGTH: 18
<212> TYPE: PRT
<213> ORGANISM: Artificial Sequence
<220> FEATURE:
<223> OTHER INFORMATION: Foot-and-mouth disease virus

<400> SEQUENCE: 43

Glu Val Ser Ser Gln Asp Arg His Lys Gln Lys Ile Ile Ala Pro Ala
1               5                   10                  15

Lys Gln

<210> SEQ ID NO 44
<211> LENGTH: 18
<212> TYPE: PRT
<213> ORGANISM: Artificial Sequence
<220> FEATURE:
<223> OTHER INFORMATION: Foot-and-mouth disease virus

<400> SEQUENCE: 44

Leu Leu Asn Phe Asp Leu Leu Lys Leu Ala Gly Asp Val Glu Ser Asn
1               5                   10                  15

Pro Gly

<210> SEQ ID NO 45
<211> LENGTH: 4
<212> TYPE: PRT
<213> ORGANISM: Artificial Sequence
<220> FEATURE:
<223> OTHER INFORMATION: Foot-and-mouth disease virus

<400> SEQUENCE: 45

Thr Thr Ala Thr
1

<210> SEQ ID NO 46
<211> LENGTH: 25
<212> TYPE: PRT
<213> ORGANISM: Artificial Sequence
<220> FEATURE:
<223> OTHER INFORMATION: Foot-and-mouth disease virus

<400> SEQUENCE: 46

Glu Val Ser Ser Gln Asp Arg His Lys Gln Lys Ile Ile Ala Pro Ala
1 5 10 15

Lys Gln Leu Leu Asn Phe Asp Leu Leu
20 25

<210> SEQ ID NO 47
<211> LENGTH: 29
<212> TYPE: PRT
<213> ORGANISM: Artificial Sequence
<220> FEATURE:
<223> OTHER INFORMATION: Foot-and-mouth disease virus

<400> SEQUENCE: 47

Lys Gln Lys Ile Ile Ala Pro Ala Lys His His His His His His Ile
1 5 10 15

Ile Ala Pro Ala Lys Gln Leu Leu Asn Phe Asp Leu Leu
20 25

<210> SEQ ID NO 48
<211> LENGTH: 23
<212> TYPE: PRT
<213> ORGANISM: Artificial Sequence
<220> FEATURE:
<223> OTHER INFORMATION: Foot-and-mouth disease virus

<400> SEQUENCE: 48

Lys Ile Ile Ala Pro Ala Lys Gln His His His His His His Lys Gln
1 5 10 15

Leu Leu Asn Phe Asp Leu Leu
20

<210> SEQ ID NO 49
<211> LENGTH: 26
<212> TYPE: PRT
<213> ORGANISM: Artificial Sequence
<220> FEATURE:
<223> OTHER INFORMATION: Foot-and-mouth disease virus

<400> SEQUENCE: 49

His His His His His His Lys Gln Leu Leu Asn Phe Asp Leu Leu Lys
1 5 10 15

Leu Ala Gly Asp Val Glu Ser Asn Pro His
20 25

<210> SEQ ID NO 50
<211> LENGTH: 13
<212> TYPE: PRT
<213> ORGANISM: Artificial Sequence
<220> FEATURE:
<223> OTHER INFORMATION: Foot-and-mouth disease virus

<400> SEQUENCE: 50

His His His His His His Ile Ile Ala Pro Ala Lys Gln
1 5 10

GENETICALLY ENGINEERED FOOT AND MOUTH DISEASE VIRUS AND RELATED PROTEINS, POLYNUCLEOTIDES, COMPOSITIONS, METHODS AND SYSTEMS

CROSS-REFERENCE TO RELATED APPLICATIONS

The present application is a continuation application of U.S. patent application Ser. No. 15/590,918 filed on May 9, 2017.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

FIELD

The present disclosure relates to genetically engineered Foot and Mouth Disease Virus (FMDV), and related proteins, polynucleotides, compositions, methods and systems.

BACKGROUND

FMDV is the etiological agent of Foot-and-mouth disease (FMD) a rapidly spreading viral disease of cloven hoofed animals and other mammals.

Various forms of FMD vaccines have been developed. The success of such vaccinations however is directly linked to the level of coverage that the vaccine produces against the virus circulating in a particular geographical location. Additional challenges on FMD control relates to the lack of cross-protection offered by strains of different serotypes and even within the same serotype among different subtypes to another. Often times within a given serotype, protection offered by a given vaccine could be insufficient if there is no antigenic match.

Accordingly, despite the efforts provided in recent years, prevention and treatment of FMD remains challenging.

SUMMARY

Provided herein are genetically engineered FMD viruses and related components, modified by the insertion of protein tags into selected regions of the capsid of the FMD virus which in several embodiments provide tagged FMD viruses suitable to be used in various diagnostic and therapeutic applications as well as in applications wherein production of the FMD virus and/or its components are desired.

According to a first aspect, a genetically modified FMD virus is described. The genetically modified FMD virus has a viral capsid comprising a genetically modified VP1 protein. The genetically modified VP1 protein is a VP1 protein of the FMD virus engineered to fuse at a C-terminus of the VP1 protein, a 2A protein of the FMDV virus, with an N-terminus of the 2A protein fused to the C-terminus of the VP1 protein. The genetically modified VP1 protein, is further engineered to include a protein tag formed by up to 100 amino acids at an insertion position selected from any one of position −1 to position +6 relative to the N-terminus of the 2A protein, or from any one of position −1 to position −7 relative to the C-terminus of the FMD VP1 protein. In the genetically modified FMD virus, the protein tag of the modified VP1 protein is presented on an external surface of the viral capsid.

According to a second aspect, a genetically modified FMD virus is described. The genetically modified FMD virus has a viral capsid comprising a modified VP1 protein. The modified VP1 protein is a VP1 protein of the FMD virus engineered to insert a protein tag formed by up to 100 amino acids in the VP1 protein at an insertion position selected from any one of position −1 to position −7 relative to the C-terminus of the VP1 protein. In the genetically modified FMD virus, the protein tag of the modified VP1 protein is presented on an external surface of the viral capsid. According to a third aspect a genetically modified VP1 protein of a FMD virus is described. The genetically modified VP1 protein is a VP1 protein of the FMD virus genetically engineered to fuse at a C-terminus of the VP1 protein, a 2A protein of the FMDV virus, with an N-terminus of the 2A protein fused to the C-terminus of the VP1 protein. The genetically modified VP1 protein is further engineered to include a protein tag formed by up to 100 amino acids within the VP1 protein or the 2A protein, at an insertion position selected from any one of position −1 to position +6 relative to the N-terminus of the 2A protein, or selected from any one of position −1 to position −7 relative to the C-terminus of the FMD VP1 protein.

According to a fourth aspect, a genetically engineered VP1 protein of an FMD virus is described. The genetically engineered VP1 protein is a VP1 protein of the FMD virus engineered to include a protein tag formed by up to 100 amino acids inserted at an insertion position selected from any one of position −1 to position −7 relative to the C-terminus of the VP1 protein.

According to a fifth aspect, a genetically engineered polynucleotide is described. The genetically engineered polynucleotide is configured to encode one or more of the modified FMD viruses and/or genetically modified VP1 proteins herein described.

According to a sixth aspect, an FMDV functionalized nanolipoprotein particle is described. The FMDV functionalized nanolipoprotein particle comprises a scaffold protein and a functionalized membrane forming lipid presenting a tag substrate. In the nanolipoprotein particle a tag substrate on the functionalized membrane forming lipid is configured to be attached to a corresponding protein tag presented on one or more genetically engineered FMD virus herein described. In some embodiments, the FMDV functionalized nanolipoprotein particle herein described further comprises a one or more genetically engineered FMD virus herein described attached to the FMDV functionalized nanolipoprotein particle through attachment of the protein tag with corresponding functionalized membrane forming lipid of the FMDV functionalized nanolipoprotein particle.

According to a seventh aspect, a composition is described comprising one or more genetically modified FMD virus, one or more genetically modified VP1 and/or one or more FMD functionalized nanolipoprotein particles together with a suitable vehicle. In some embodiments, the composition is a pharmaceutical composition comprising one or more genetically modified FMD virus, and/or one or more FMD functionalized nanolipoprotein particles together with a pharmaceutically acceptable vehicle.

According to an eighth aspect, a vaccine is described, the vaccine comprising one or more genetically modified FMD viruses, one or more nanolipoprotein particle comprising a scaffold protein and a functionalized membrane forming lipid presenting a tag substrate and/or one or more functionalized FMD nanolipoprotein particles herein described together with a pharmaceutically acceptable vehicle.

According to a ninth aspect, a method to treat or prevent FMD in a cloven-hoofed animal, the method comprising administering to the cloven-hoofed animal an effective amount of a pharmaceutical composition vaccine herein described.

According to a tenth aspect, a method and system to provide a tagged FMD virus are described. The method comprises genetically engineering a FMD virus comprising a VP1 protein genetically engineered to fuse an N-terminus of a 2A protein of the FMD virus with a C-terminus of the VP1 protein and further genetically engineering the FMD virus to insert a protein tag formed by up to 100 amino acids located at an insertion position selected from any one of position −1 to position +6 relative to the N-terminus of the 2A protein, or selected from any one of position −1 to position −7 relative to the C-terminus of the FMD VP1 protein, or genetically engineering a FMD virus comprising a VP1 protein to insert a protein tag formed by up to 100 amino acids at an insertion position selected from any one of position −1 to position −7 relative to the C-terminus of the VP1 protein.

The system comprises at least one polynucleotide encoding for at least one protein tag formed by up to 100 amino acids and reagents for the introduction of the at least one polynucleotide in the FMDV virus.

According to an eleventh aspect, an array to is described, the array comprising one or more genetically modified FMD viruses herein described attached to a substrate. In some embodiments, the array can be used for detection of antibody against one or more strains of FMD virus for investigation, research and/or diagnostic purpose.

Genetically modified FMD virus, genetically engineered proteins and polynucleotides, FMDV functionalized nanolipoprotein particle, compositions, vaccines, methods and systems herein described allow in several embodiments to provide rationally designed FMDV vaccines displaying tags that interact with tag substrates, nanolipoprotein particles (NLP) presenting tag substrates and NLPs containing adjuvant molecules.

Genetically modified FMD virus, genetically engineered proteins and polynucleotides, FMDV functionalized nanolipoprotein particle, compositions, vaccines, methods and systems herein described allow in several embodiments to provide a mutant FMDV vaccine that can be used in a chemically-inactivated form is capable of protecting an animal from clinical FMD when challenged with virulent FMDV wherein said vaccine comprises FMDV modified to display tags on surface-exposed regions of the FMD viral capsid, wherein the latter are capable of interacting with adjuvanted NLP nanoconstructs.

Genetically modified FMD virus, genetically engineered proteins and polynucleotides, FMDV functionalized nanolipoprotein particle, compositions, vaccines, methods and systems herein described allow in several embodiments to provide a genetically modified FMDV encoded by the isolated polynucleotide molecule recited above where the modification enables affinity purification of virus via binding on the tag to tag substrates on columns, beads, and plates.

Genetically modified FMD virus, genetically engineered proteins and polynucleotides, FMDV functionalized nanolipoprotein particle, compositions, vaccines, methods and systems herein described allow in several embodiments to provide a genetically modified FMDV encoded by the isolated polynucleotide molecule recited above where the modification enables recognition of tags by antibodies that specifically recognize the tag sequence.

Genetically modified FMD virus, genetically engineered proteins and polynucleotides, FMDV functionalized nanolipoprotein particle, compositions, vaccines, methods and systems herein described allow in several embodiments to provide a FMDV cDNA clone that is further modified to include unique restriction endonuclease sites that facilitate the exchange of DNA cassettes representing relevant capsid coding regions of other FMDV strains/serotypes/and subtypes of FMDV field isolates.

Genetically modified FMD virus, genetically engineered proteins and polynucleotides, FMDV functionalized nanolipoprotein particle, compositions, vaccines, methods and systems herein described allow in several embodiments to provide a marker vaccine which allows a serological distinction between vaccinated animals and animals infected with FMDV.

Genetically modified FMD virus, genetically engineered proteins and polynucleotides, FMDV functionalized nanolipoprotein particle, compositions, vaccines, methods and systems herein described allow in several embodiments to provide a method for protecting an animal against FMD by administering an effective amount of rationally designed and chemically-inactivated marker FMDV vaccine.

Genetically modified FMD virus, genetically engineered proteins and polynucleotides, FMDV functionalized nanolipoprotein particle, compositions, vaccines, methods and systems herein described allow in several embodiments to provide a method for delaying onset or severity of FMD in an animal by administering an effective amount of rationally designed and chemically-inactivated marker FMDV vaccine formulation.

Genetically modified FMD virus, genetically engineered proteins and polynucleotides, FMDV functionalized nanolipoprotein particle, compositions, vaccines, methods and systems herein described allow in several embodiments to provide effective vaccine formulations as well as opportunities for purification through binding to divalent cations and anti-tag antibody recognition protocols.

Genetically modified FMD virus, genetically engineered proteins and polynucleotides, FMDV functionalized nanolipoprotein particle, compositions, vaccines, methods and systems herein described can be used in connection with various applications wherein detectability, purification of FMD virus and/or treatment and/or diagnosis of FMD is desired. For example, genetically modified FMD virus, genetically engineered proteins and polynucleotides, FMDV functionalized nanolipoprotein particle, compositions, vaccines, methods and systems can be used for delivery of a genetically modified FMD virus to a specific target destination, as a platform for immunostimulating agents, vaccine development and use, and/or to contain cell-targeting moieties. Additional exemplary applications include uses of genetically modified FMD virus, genetically engineered proteins and polynucleotides, FMDV functionalized nanolipoprotein particle, compositions, vaccines, methods and systems in several fields including basic biology research, applied biology, bio-engineering, bio-energy, medical research, medical diagnostics, therapeutics, bio-fuels, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 1A shows the 5' and 3' untranslated region (UTR) [1] and the structural and non-structural proteins are shown as open and filled boxes, respectively. The S-fragment (S) poly-C track ($C_{35}$), IRES and polyA are shown. Fourteen protein products are indicated, including $L^{pro}$ (L), VP4 (1A), VP3 (1B), VP2 (1C), VP1 (1D), 2A, 3A, 3B1-3 ($3B_{123}$), $3C^{pro}$ (3C), $3D^{pol}$ (3D) Parental $A_{24}$ Cruzeiro is labeled as $A_{24}$ FMDV WT; whereas two exemplary mutant FMDVs containing 6×-His tag in VP1 and 2A are labeled as $A_{24}$ FMDV $P1_{6H}$ and $A_{24}$ FMDV $2A_{6H}$, respectively. VP1 residues surrounding 6×-His tag and ending at the junction with 2A are shown as well as the first seven residues at the N-terminus of 2A. His residues are shown in grey letters. In the zoomed in view of VP1-2A, the interface, including the location of the 6×His tags (grey circles) and surrounding sequences in the in two mutant viruses are shown, wherein $A_{24}$FMDV WT shows sequences TTAT (SEQ ID NO:45) and EVSSQDRHKQKIIAPAKQLLNFDLL (SEQ ID NO:46), $A_{24}$FMDV $P1_{6H}$ shows sequences TTAT (SEQ ID NO:45) and KQKIIAPAKHHHHHHIIAPAKQLLNFDLL (SEQ ID NO:47), and $A_{24}$FMDV $2A_{6H}$ shows sequences TTAT (SEQ ID NO:45) and KIIAPAKQHHHHHHHKQLLNFDLL (SEQ ID NO:48). The sites of the 6×-His tag insertions on the two mutant viruses are marked with the viral capsid protein VP1 residue number and arrows. The FMDV $3C^{pro}$ cleavage site is marked by an arrow ↓ in the coding sequence at the junction between VP1 and 2A proteins—'↑' crossed out with 'X' reflects that the site is not cleaved by $3C^{pro}$. FIG. 1B depicts the representation of P1 and 2A FMDV proteins and the location of unique restriction sites for cloning of a capsid cassette by those of different serotypes. The two unique restriction sites marked as R1 and R2 are shown, indicated by ↑. R1 refers to a Pf1M1 restriction enzyme recognition site covering nucleotides 1547-1559 of FMDV genome of $pA_{24}$Cru [2, 3] contained in the $L^{pro}$ coding region (L). R2 indicates a NheI restriction enzyme recognition site covering nucleotides 3911-3916 of the FMDV genome in the 2A coding region. The FMDV $3C^{pro}$ cleavage site in the two mutant viruses is marked by ↓ in $A_{24}$ FMDV $P1_{6H}$; X reflects that the site is not cleaved by $3C^{pro}$ in $A_{24}$ FMDV $2A_{6H}$ FIG. 1C shows the amino acid sequence of the C-terminal 18 amino acids of exemplary FMDV $A_{24}$ Cruzeiro VP1 protein (EVSSQDRHKQKIIAPAKQ (SEQ ID NO:43)), showing the C-terminal amino acid of the VP1 (Q, bold underlined). Numbers indicate positions of tag insertion sites (arrows) relative to the C-terminus of FMDV protein VP1. Horizontal lines indicate peptide bonds between adjacent amino acids. FIG. 1D shows the amino acid sequence of the N-terminal 18 amino acids (LLNFDLLKLAGDVESNPG (SEQ ID NO:44)) of exemplary FMDV $A_{24}$ Cruzeiro protein 2A, showing the N-terminal amino acid of 2A (L, italic underlined). Numbers indicate positions of tag insertion sites (arrows) relative to the N-terminus of FMDV protein 2A. Horizontal lines indicate peptide bonds between adjacent amino acids.

FIGS. 2A-2D show the nucleotide and amino acid sequences of exemplary $A_{24}$FMDV $2A_{6H}$ and $A_{24}$FMDV $P1_{6H}$ mutant viruses. FIG. 2A shows the nucleotide sequence (SEQ ID NO:12) and FIG. 2B, the amino acid sequence (SEQ ID NO:13) of $A_{24}$FMDV $2A_{6H}$. The His coding sequences are shown underlined and in bold. 2A coding sequence is displayed in italics. FIGS. 2C and 2D show the nucleotide sequence (SEQ ID NO:14) and the amino acid sequence (SEQ ID NO:15) of $A_{24}$FMDV $P1_{6H}$, respectively. Underlined is the 6×His tag insert. The 18 extra nucleotides that encode the 6 extra encoded amino acids are depicted in lowercase text. The His coding sequences are shown underlined and in bold. 2A coding sequence is displayed in italics.

FIGS. 5A-5C depict the in vitro characterization of marker His-tagged FMDV. FIG. 5A shows a one-step growth curve of $A_{24}$WT and marker His-tagged FMDV viruses. Cell monolayers were mock-infected or infected with $A_{24}$WT, $A_{24}$FMDV $2A_{6H}$, $A_{24}$FMDV $P1_{6H}$, at a MOI of 5 PFU/cells. Procedures used for viral infection are described in Example 3. FIG. 5B compares plaque morphologies of three viruses. Cell monolayers were mock-infected or infected with $A_{24}$WT, $A_{24}$FMDV $2A_{6H}$, $A_{24}$FMDV $P1_{6H}$, at a MOI of 0.01 PFU/cells and overlaid with Gum-tragacanth overlay. 24 hr post infection, the plaques were stained with crystal violet Histochoice fixative and developed. The titers and plaque morphologies for $A_{24}$WT, $A_{24}$FMDV $2A_{6H}$ and $A_{24}$FMDV $P1_{6H}$, respectively, are shown. FIG. 5C depicts a virus neutralization assay conducted for $A_{24}$WT, $A_{24}$FMDV $2A_{6H}$ and $A_{24}$FMDV $P1_{6H}$, respectively, in the presence of hyperimmune serum from a WT FMDV $A_{24}$-infected bovine. The r1 value of each virus was determined.

FIG. 6A shows detection of the 6His-tag by Enzyme linked immunosorbent assay (ELISA). 4.5 to 29.1 μg of FMDV $3D^{pol}$-6×-His were bound to Ni-NTA-coated pre-blocked plates (Qiagen). After overnight incubation of $3D^{pol}$-6×-His, five PBS washes were performed. Rabbit polyclonal anti-His antibody (Novus Biologicals) was added at 1:500 dilutions in 1% BSA-PBS. After 1 hr incubation, five PBS washes were performed and goat anti-rabbit 1:10000 dilution (Sigma Aldrich) was added. After 1 hr the plate was washed 5 times with PBS and the signal was developed using TMB Sure kit [4]. The OD was read at 640 nM. Values on the X-axis represent the concentration of 6×-His-tagged FMDV $3D^{pol}$ and Y-axis values show the OD at 640 nM. FIG. 6B depicts detection of 6×-His tag expression for $A_{24}$FMDV $2A_{6H}$ or $A_{24}$FMDV $P1_{6H}$-infected cell lysates by ELISA. The wells of Ni-NTA-coated pre-blocked plates were incubated with either mock or mutant $A_{24}$FMDV $2A_{6H}$, or $A_{24}$FMDV $P1_{6H}$ infected cell lysates overnight. As described above, 6×-His tag was detected using anti-His antibody (Novus Biologicals). Columns 1, 2 and 3 correspond to $A_{24}$FMDV $2A_{6H}$-, $A_{24}$FMDV $P1_{6H}$- and mock-infected cell lysates, respectively. FIG. 6C shows detection of 6×-His-tagged FMDV VP1 expression by Western Blot analysis. Virus- or mock-infected cell lysates were electrophoresed and transferred onto nitro-cellulose membrane (GE Health Care) using NuPage System (Life Technologies). The membrane was incubated with rabbit polyclonal anti-VP1 (1:2000) for 2 hr followed by 1 hr incubation with Goat anti-rabbit-HRP (1:10,000 Sigma Aldrich). The protein bands were developed using Super Signal West Dura Reagent (Shaw et al., supra). The detection was done using dental x-ray films (Kodak). Lanes 1, 2, 3 and M represent $A_{24}$ FMDV WT-, $A_{24}$FMDV $2A_{6H}$-, $A_{24}$FMDV $P1_{6H}$- and mock-infected cell lysates, respectively. The FMDV VP1-specific protein band is shown by an arrow in FIG. 6C.

FIG. 7 Panel C shows MPLA:NiNLP alone. The Table shown in FIG. 7 Panel D shows the number of MPLA:NiNLP bound to $A_{24}$ FMDV $P1_{6H}$. detected in electron microscopy captured images.

FIG. 8A shows the electrophoretic mobility of mutant $A_{24}$FMDV $P1_{6H}$ virus alone or in the presence of increasing concentrations of NiNLP-MPLA (1:0, 1:1, 1:2.5, 1:5 and 1:7.5) in lanes 1-5 respectively. After 45 min incubation at room temperature, the reactions were loaded on to 1% agarose gel and then transferred to nitrocellulose membrane by a capillary transfer method. The presence of structural proteins was determined by detection using a rabbit polyclonal anti-VP1, followed by goat anti-rabbit treatment and developed on x-ray film. The presence of a reagent in a reaction is indicated by a + sign; absence, by a − sign. The $A_{24}$FMDV $P1_{6H}$- and $A_{24}$FMDV $P1_{6H}$+ NiNLP-specific bands are marked with arrows. FIG. 8B shows electrophoretic mobility of the $A_{24}$FMDV $P1_{6H}$ virus in the presence of increasing concentrations of NiNLP and anti-his tag antibody. $A_{24}$FMDV $P1_{6H}$ was mixed with NiNLP-MPLA at ratios of 1:0, 1:1, 1:2.5, 1:5 and 1:7.5 for lanes 1, 2, 3, 4 and 5, respectively. Lane 6 represents the virus only control. Lane 7 represents virus+anti 6×-His antibody at 1:500 dilution (Novus Biologicals). Lanes 8 and 9 represent virus+anti-6×-His antibody+NiNLP (1:2.5 to virus) and virus+anti 6×-His antibody+NiNLP (1:5 to virus), respectively. $A_{24}$FMDV $P1_{6H}$-, $A_{24}$FMDV $P1_{6H}$+Ni-NLP-, $A_{24}$FMDV $P1_{6H}$+anti 6×-His- and $A_{24}$FMD $P1_{6H}$+anti 6×-His+NiNLP-specific super shifted bands are marked with arrow. Sign + shows the presence of a reagent in a reaction; − sign indicates the absence of a reagent from the reaction.

FIG. 9B. NiNLP mediated displacement of $A_{24}$FMDV $P1_{6H}$ from Ni-NTA coated plate. $A_{24}$FMDV $P1_{6H}$ (1 μg/well) was bound to the Ni-NTA coated, pre-blocked plates (Qiagen) overnight; plates were then washed five times with PBS. NiNLP was added for 1 h (0-100 ng/well) to the wells that had virus bound. Rabbit polyclonal anti-His antibody (Novus Biologicals) was added at 1:500 dilutions in 1% BSA-PBS. 1 hr later five PBS washes were performed and goat anti-rabbit 1:10000 dilution (Sigma Aldrich) was added. After 1 hr the plate was washed 5 times with PBS and the signal was developed using TMB Sure kit [4]. The OD was read at 640 nM. Values on the X-axis represent the concentration of NiNLP-MPLA and Y-axis values show the OD at 640 nM.

FIG. 10A: 200 μl of clarified mock cell lysate or virus-infected cell lysates were mixed with 100 μl of Co-NTA resin and incubated overnight at 4° C. After incubation, the protein bound resin was washed with 50 mM Tris-HCl-500 mM NaCl pH 7.4. The proteins bound to resin were eluted with 300 mM imidazole-50 mM Tris-HCl-500 mM NaCl pH 7.4, resolved on SDS-PAGE and transferred to nitrocellulose membrane. The protein bands were developed with 1:2500 goat-anti rabbit VP1. Lanes 1, 2, 3 and 4 represent the eluates of Mock-, $A_{24}$ FMDV WT-, $A_{24}$ FMDV $2A_{6H}$- and $A_{24}$ FMDV $P1_{6H}$-infected cell lysates, respectively. FIG. 10B depicts purification of FMDV $A_{24}$ 6×-His FMD virus using a Ni (HisTrap™ FF) column. Clarified infected cell lysate of $A_{24}$ FMDV $P1_{6H}$ virus was bound to a HisTrap™ FF crude 1 ml column, eluted with different concentrations of imidazole (100-500 mM). Crude lysates of virus (V) and different fractions from column purification (FT, E1-E4) were analyzed by western blotting for the presence of FMDV capsid proteins, VP1 and VP3. Lane FT denotes flow through fraction, lane V is initial crude virus before dialysis, and E1, E2, E3 and E4 are elution fractions 1, 2, 3 and 4 carried out with 100, 200, 300 and 500 mM imidazole, respectively. The VP1 and VP3 panels represent the protein bands recognized by FMDV $A_{24}$ VP1- and VP3-specific antibodies.

FIG. 11A shows a schematic of an exemplary affinity column method for purification of $A_{24}$FMDV $P1_{6H}$ virus. The $A_{24}$FMDV $P1_{6H}$ virus capsids are shown as spheres, FMDV non-structural proteins are shown as triangles and squares. Cellular proteins are shown as discs. Two alternative buffers were evaluated to elute the virus from the column: imidazole-based (buffer-I) or EDTA-based (buffer-E). Western blot analysis and virus titer were determined for 6×-His-tagged $A_{24}$ FMDV $P1_{6H}$ virus following purification on Co-NTA resin columns. FIG. 11B depicts affinity column purification of FMDV $P1_{6H}$ virus using buffer with imidazole. Crude and clarified lysates (V) from $A_{24}$ FMDV $P1_{6H}$-infected cells were bound to Co-NTA columns in the presence of 25 mM imidazole, then washed (W) with 25 mM imidazole and eluted with increasing concentrations of imidazole (100-500 mM). The initial crude lysates (V) and different fractions eluted from the column (FT, W E1-E4) were analyzed by western blotting using polyclonal antisera against FMDV capsid protein VP1 (Panel VP1) or using a monoclonal antibody against the FMDV non-structural protein $3D^{pol}$ (panel $3D^{pol}$).

FIG. 11C depicts affinity column purification of FMD $P1_{6H}$ virus using buffer with EDTA. In a parallel experiment, the 6×His mutant virus was bound to Co-NTA resin columns using binding and wash buffers without EDTA. Lanes FT and W denote flow through and wash fraction, respectively. Different fractions obtained from column purification (V, FT, W, E1-E4) were analyzed by WB for the presence of FMDV capsid protein VP1 (Panel VP1) and non-structural protein 3D (Panel $3D^{pol}$) as described in FIG. 11B. Elution fractions 1, 2, 3 and 4 were carried out with 10, 25, 50 and 100 mM EDTA in buffer-E, respectively. Virus titers were determined by plaque assays, as described in Example 3.

FIGS. 12A-C show that mice immunized with inactivated parental FMDV $A_{24}$ Cru vaccine are protected from lethal challenge. 6 to 7 weeks old female C57BL/6 mice (n=6/group) were intraperitoneally (i.p.) vaccinated with the indicated amounts of inactivated FMDV $A_{24}$ with or without adjuvant Montanide ISA206. Seven days after vaccination, animals were challenged by subcutaneous (s.c.) injection in the footpad with a lethal dose of parental FMDV $A_{24}$ Cru. Survival rates (FIG. 12A) and viremia expressed as plaque forming units per ml of serum (pfu/ml) (FIG. 12B) were followed for 7 days post challenge. A control naïve group was included (n=5 or 6). FIG. 12C depicts analyses of neutralizing antibodies in serum of mice inoculated with $A_{24}$FMDV $P1_{6H}$ with or without NLPs before challenge with a lethal dose of parental FMDV $A_{24}$ Cru (period indicated between zero days post-vaccination, 0 dpv and 0 days post challenge, 0dpc) and after challenge (indicated as 0dpc-14dpc). Titers are expressed as the inverse dilution of serum yielding a 50% reduction of virus titer (Log 10 $TOD_{50}$/ml). Each data point represents the mean (±SD) of each group. Error bars represent the variation among individual animals within a group.

FIG. 13C depicts analyses of neutralizing antibodies in serum at 7 days post vaccination (=0dpc) and different times post-challenge (dpc). Titers are expressed as the inverse dilution of serum yielding a 50% reduction of virus titer (Log 10 $TOD_{50}$/ml). Each data point represents the mean (±SD) of each group. Error bars represent the variation among individual animals within a group. FIG. 13D shows electron microscopy images of $A_{24}$FMDV $P1_{6H}$ 140 S particles alone (left) and after formulated with MPLA:NiNLP (right) in the vaccine used to immunize animals.

DETAILED DESCRIPTION

Figure 1A:
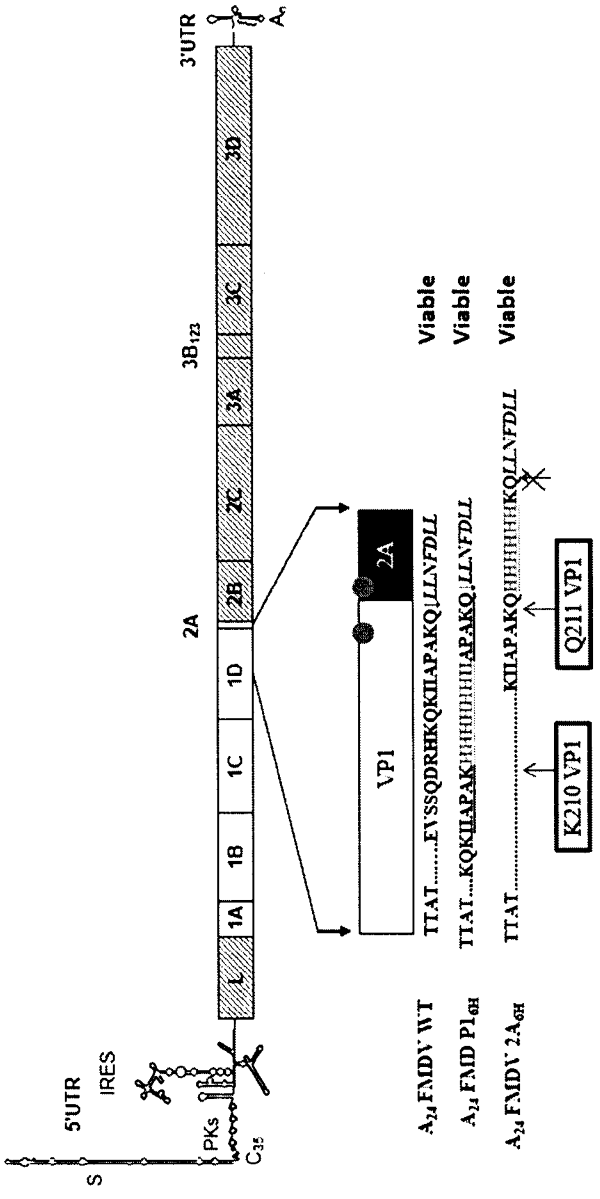
FIGS. 1A and 1B show schematic representations of FMDV genome showing the position of His-tags introduced in the mutant viruses.

Provided herein are genetically engineered FMD viruses that are modified by the insertion of protein tags into selected regions of the capsid of the FMD virus.

As used herein, the term "Foot-and-mouth disease" or "FMD" indicates an infectious and sometimes fatal viral disease that affects mammals and in particular, cloven-hoofed animals, including domestic and wild bovides and swines. "Mammals" include any warm-blooded vertebrates of the Mammalia class, including humans. The terms "porcine" and "swine" are used interchangeably herein and refer to any animal that is a member of the family Suidae such as, for example, a pig. Exemplary susceptible animals include cattle, water buffalo, sheep, goats, pigs, antelope, deer, and bison, hedgehogs and elephants; llamas and alpacas. In laboratory experiments, mice, rats, and chickens have been successfully infected by artificial means, but they are not believed to contract the disease under natural conditions. Humans are very rarely infected. Symptoms of FMD comprise high fever for approximately two to six days, followed by blisters inside the mouth and on the feet that may rupture and cause lameness. FMD has severe implications for animal farming, since it is highly infectious and can be spread by infected animals through aerosols, through contact with contaminated farming equipment, vehicles, clothing, or feed, and by domestic and wild predators. In particular symptoms in cattle and swine caused by a FMDV infection. Containment of the FMD demands considerable efforts in vaccination, strict monitoring, trade restrictions, and quarantines, and occasionally the killing of animals [5-7].

FMD etiological agent is the foot-and-mouth disease virus (FMDV), a picornavirus which is the prototypical member of the Aphthovirus genus.

The term "virus" indicates an infectious agent that replicates only inside the living cells of other organisms. Viruses can infect all types of life forms, from animals and plants to microorganisms, including bacteria and archaea. Viruses display a wide diversity of shapes and sizes, called morphologies. In general, viruses are much smaller than bacteria. Most viruses that have been studied have a diameter between 20 and 300 nm. Most viruses cannot be seen with an optical microscope so scanning and transmission electron microscopes are used to visualize virions.

The term "virion" indicates the complete, infective form of a virus outside a host cell. While not inside an infected cell or in the process of infecting a cell, viruses exist in the form of independent particles. These virions, also known as viral particles, consist of two or three parts: (i) the genetic material made from either DNA or RNA; (ii) a protein coat, called the capsid, which surrounds and protects the genetic material; and in some cases (iii) an envelope of lipids that surrounds the protein coat when they are outside a cell.

A "functional virion" is a virus particle that is able to enter a cell capable of hosting the virus, and express genes of its particular genome (either an unmodified genome or a genetically modified genome as described herein) within the cell. Cells capable of hosting a FMDV include baby hamster kidney, strain 21, cells (BHK-21) and BHK-$\alpha_V\beta_6$ cells expressing bovine $\alpha_V\beta_6$ integrin. Other mammalian cells, especially other bovine and porcine cells, can also serve as suitable host cells for FMDV virions.

A picornavirus is a virus belonging to the family Picornaviridae, a family of viruses in the order Picornavirales. Vertebrates, including humans, serve as natural hosts. Picornaviruses are nonenveloped viruses that represent a large family of small, cytoplasmic, plus-strand RNA (~7.5 kb) viruses with a 30 nm icosahedral capsid.

The term "capsid" refers to the protein shell of a virus. It consists of several oligomeric structural subunits made of protein. The observable 3-dimensional morphological subunits, which may or may not correspond to individual proteins, are called capsomeres. The capsid encloses the genetic material of the virus. Capsids are broadly classified according to their structure. The majority of viruses have capsids with either helical or icosahedral structure. The icosahedral shape, which has 20 equilateral triangular faces, approximates a sphere, while the helical shape resembles the shape of a spring, taking the space of a cylinder but not being a cylinder itself. The capsid faces can consist of one or more proteins. For example, the foot-and-mouth disease virus capsid has faces consisting of three proteins named VP1-3. Some viruses are enveloped, meaning that the capsid is coated with a lipid membrane known as the viral envelope. The envelope is acquired by the capsid from an intracellular membrane in the virus' host; examples include the inner nuclear membrane, the golgi membrane, and the cell's outer membrane. Once the virus has infected a cell and begins replicating itself, new capsid subunits are synthesized according to the genetic material of the virus, using the protein biosynthesis mechanism of the cell. During the assembly process, a portal subunit is assembled at one vertex of the capsid. Through this portal, viral DNA or RNA is transported into the capsid. Structural analyses of major capsid protein (MCP) architectures can been used to categorize viruses into families. For example, the bacteriophage PRD1, Paramecium bursaria *Chlorella* algal virus, and mammalian adenovirus have been placed in the same family. Although the icosahedral structure is extremely common among viruses, size differences and slight variations exist between virions. Given an asymmetric subunit on a triangular face of a regular icosahedron, with three subunits per face 60 such subunits can be placed in an equivalent manner. Most virions, because of their size, have more than 60 subunits. These variations have been classified on the basis of the quasi-equivalence principle proposed by Donald Caspar and Aaron Klug [8].

In particular, FMD viruses possess an icosahedral capsid shell formed by various copies (typically 60) of each viral protein VP1, VP2, VP3 and VP4 which are cleavage products of the P1 capsid polypeptide precursor. The structural proteins, VP1, VP2, and VP3, fold into an eight-stranded wedge-shaped β-barrel to form the outer capsid structure. The VP4 protein is buried within the capsid and is myristoylated at its N-terminus. By electron microscopy, the FMD virion appears to be a round particle with a smooth surface and a diameter of about 25-30 nm. The integrity of the FMDV capsid structure is very relevant in eliciting protective immune responses and in determining serotype and subtype specificities. Previous studies have revealed surface-exposed regions on the FMDV capsid as sites suitable for the insertion or substitution of foreign epitopes [9-11]. Given the flexibility of the hypervariable G-H loop [12], replacing the FMDV G-H loop of VP1 by those of other serotypes is well tolerated by the virus capsid [2, 3, 9, 13].

The synthesis of FMDV capsid VP proteins and other viral proteins typically include 2A 'cleavage' during translation.

The term "cleavage" and "cleaved" as used herein refers to the breaking of a peptide bond between two amino acids within a di-peptide, polypeptide, protein, or polyprotein. In particular, cleavage can refer to the separation of two fused protein segments via breaking a peptide bond. Cleavage of peptide bonds typically occurs via hydrolysis reaction mediated by an enzyme such as a protease. For example, cleavage of the FMD virus polyprotein to separate FMD virus proteins VP1 and 2A occurs via enzymatic cleavage at the N-terminus of the 2A protein, catalyzed by the enzyme 3Cpro in a cleavage during translation process.

Figure 1B:
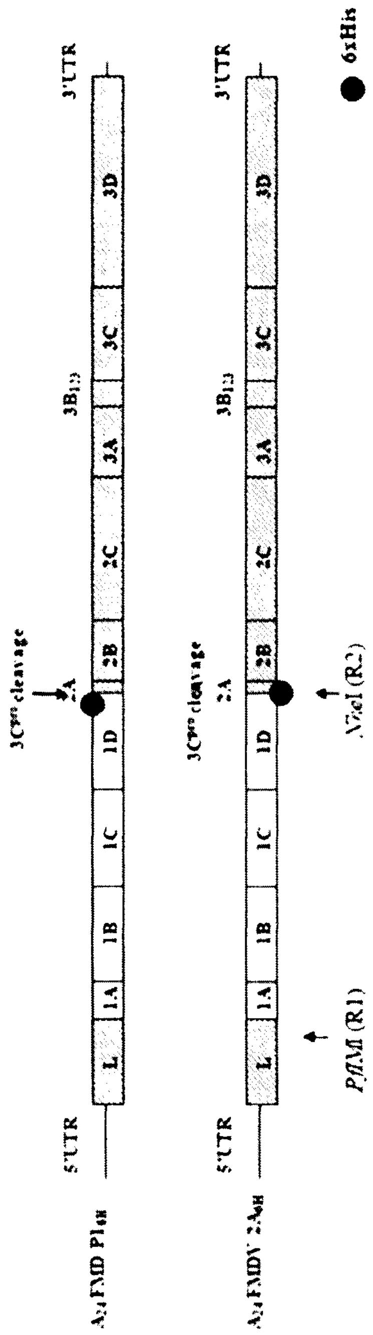

This process involves proteases that inhibit the synthesis of normal cell proteins, and other proteins that interact with components of the host cell. The FMDV genome is an ssRNA molecule of mRNA sense of approximately 8500 nucleotides (FIGS. 1A and 1B). A single long open reading frame of 2332 codons would encode a polyprotein of 259K, but full-length translation products are not observed because the nascent polyprotein undergoes primary (co-translational) cleavages, which produce four products, L, P1-2A, 2BC and P3. The viral non-structural protein 3C mediated this cleavage. In addition leader protease (Lpro) also mediates virus polyprotein cleavage. Analysis of the processing of these polyproteins shows that a 19 amino acid sequence spanning 2A is sufficient to mediate polyprotein cleavage at a site immediately C-terminal to 2A, whereas deletions extending into the 2A region prevent cleavage [14].

In embodiments herein described, genetically engineered FMDV are modified by the strategic insertion of a protein tag into viral capsid proteins in targeted regions predicted to be exposed on the surface of the viral capsid.

The terms "genetically engineered" or "genetically modified", as used herein and unless otherwise indicated, indicates genetically mutated proteins or polynucleotides (e.g. by having one or more nucleotides or amino acids replaced, deleted and/or added). Polynucleotide and protein molecules can be genetically mutated using recombinant techniques known to those of ordinary skill in the art, including by site-directed mutagenesis, or by random mutagenesis such as by exposure to chemical mutagens or to radiation, as known in the art.

As used herein, in relation to proteins, the term "insertion" of a first protein in a second protein refers to the introduction of the second protein in between two adjacent amino acids of the second protein. As a result, an inserted first protein is located in between a first segment of the second protein having one of the adjacent amino acids at its C-terminus and a second segment of the second protein having the other one of the adjacent amino acids at its N-terminus In particular, an insertion of a first protein in a second protein is performed by forming a first covalent bond between the N-terminal amino acid of the first protein with a first amino acid of the two adjacent amino acids the second protein, and a second covalent bond between the C-terminal amino acid of the first protein with a second amino acid of the two adjacent amino acids of the second protein. As would be understood by a skilled person, a covalent bond between two amino acids in a protein is typically a peptide bond, which is a covalent bond between a carboxyl group and an amino group of two molecules or portions thereof, which results in releasing a molecule of water.

Accordingly, an insertion of a second protein in a first protein when performed at a protein level typically results in breaking the peptide bond between the two adjacent amino acids of the first protein and forming two new peptide bonds: one between one of the two adjacent amino acids of the first protein and the N-terminal amino acid of the second protein and the other peptide bond formed between the other one of the two adjacent amino acid of the first protein and the C-terminal amino acid of the second protein.

In embodiments herein described, genetically modified FMD viruses are described comprising a genetically modified VP1 protein comprising a VP1 protein of the FMD virus engineered to insert a protein tag up to 100 amino acids at insertion positions in the VP1 protein of the FMD virus. Having the ability to mark (tag) the FMDV capsid without affecting virus viability or altering its ability to enter susceptible cells, provides opportunities for the mutant viruses to bind to tag-specific antibodies, or other complex molecules, depending on the tag selection.

The term "tag" as used herein means protein tags comprising peptide sequences introduced onto a recombinant protein. Tags can be removable by chemical agents or by enzymatic means, such as proteolysis or splicing. Tags can be attached to proteins for various purposes: Affinity tags are appended to proteins so that they can be purified from their crude biological source using an affinity technique. These include chitin binding protein (CBP), and the poly(His) tag. The poly(His) tag is a widely-used protein tag; it binds to metal matrices. Chromatography tags can be used to alter chromatographic properties of the protein to afford different resolution across a particular separation technique. Often, these consist of polyanionic amino acids, such as FLAG-tag. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Protein tags can allow specific enzymatic modification (such as biotinylation by biotin ligase) or chemical modification (such as reaction with FlAsH-EDT2 for fluorescence imaging). Tags can be combined, in order to connect proteins to multiple other components. However, with the addition of each tag comes the risk that the native function of the protein may be abolished or compromised by interactions with the tag. Therefore, after purification, tags are sometimes removed by specific proteolysis (e.g. by TEV protease, Thrombin, Factor Xa or Enteropeptidase).

Exemplary tags comprise the following, among others known to persons skilled in the art: Peptide tags, such as: AviTag, a peptide allowing biotinylation by the enzyme BirA and so the protein can be isolated by streptavidin (GLNDIFEAQKIEWHE (SEQ ID NO:18)); Calmodulin-tag, a peptide that can be bound by the protein calmodulin (KRRWKKNFIAVSAANRFKKISSSGAL (SEQ ID NO:19)); polyglutamate tag, a peptide binding efficiently to anion-exchange resin such as Mono-Q (EEEEEE (SEQ ID NO:20)); E-tag, a peptide recognized by an antibody (GAPVPYPDPLEPR (SEQ ID NO:21)); FLAG-tag, a peptide recognized by an antibody (DYKDDDDK (SEQ ID NO:22)); HA-tag, a peptide from hemagglutinin recognized by an antibody (YPYDVPDYA (SEQ ID NO:23)); His-tag, typically 5-10 histidines that can be bound by a nickel or cobalt chelate (HHHHHH (SEQ ID NO:24)); Myc-tag, a peptide derived from c-myc recognized by an antibody (EQKLISEEDL (SEQ ID NO:25)); NE-tag, a novel 18-amino-acid synthetic peptide (TKENPRSNQEESYDDNES (SEQ ID NO:26)) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS (SEQ ID NO:27)); SBP-tag, a peptide which binds to streptavidin (MDEKTTGWRGGHVVEGLAGELEQLRARLEHHPQGQREP (SEQ ID NO:28)); Softag 1, for mammalian expression (SLAELLNAGLGGS (SEQ ID NO:29)); Softag 3, for prokaryotic expression (TQDPSRVG (SEQ ID NO:30)); Strep-tag, a peptide which binds to streptavidin or the modified streptavidin called streptactin (Strep-tag II: WSHPQFEK (SEQ ID NO:31)); TC tag, a tetracysteine tag that is recognized by FlAsH and ReAsH biarsenical compounds (CCPGCC (SEQ ID NO:32)); V5 tag, a peptide recognized by an antibody (GKPIPNPLLGLDST (SEQ ID NO:33)); VSV-tag, a peptide recognized by an antibody (YTDIEMNRLGK (SEQ ID NO:34)); Xpress tag (DLYDDDDK (SEQ ID NO:35)); Covalent peptide tags such as: Isopeptag, a peptide which binds covalently to pilin-C protein (TDKDMTITFTNKKDAE (SEQ ID NO:36)); SpyTag, a peptide which binds covalently to SpyCatcher protein (AHIVMVDAYKPTK (SEQ ID NO:37)); SnoopTag, a peptide which binds covalently to SnoopCatcher protein (KLGDIEFIKVNK (SEQ ID NO:38)). In embodiments described herein, any of the tags of SEQ ID NO:18-38, and other tags known to those skilled in the art, can comprise one or more amino acid substitutions, insertions, or deletions that do not alter the function of the tag, and can further comprise one or more additional amino acids, up to a maximum tag length of 100 amino acids. In preferred embodiments, the tag comprises up to a maximum of 20 amino acids in length.

In some embodiments, the protein tag can be a polyhistidine tag. A polyhistidine-tag is an amino acid motif in proteins that typically consists of six histidine (His) residues typically, often at the N- or C-terminus of the protein. It is also known as hexahistidine-tag, 6×His-tag, His6 tag and by the trademarked name His-tag (registered by EMD Biosciences). The total number of histidine residues can vary in the tag. N- or C-terminal his-tags can also be followed or preceded, respectively, by a suitable amino acid sequence that facilitates a removal of the polyhistidine-tag using endopeptidases. This extra sequence is not necessary if exopeptidases are used to remove N-terminal His-tags (e.g., Qiagen TAGZyme). Polyhistidine-tagging can be used to detect protein-protein interactions in the same way as a pull-down assay. Fluorescent hexahistidine CyDye tags are also available. These use Nickel covalent coordination to EDTA groups attached to fluorophores in order to create dyes that attach to the polyhistidine tag. This technique has been shown to be effective for following protein migration and trafficking. This technique may also be effective in order to measure distance via Fluorescent Resonance Energy Transfer.

In embodiments herein described, insertion of a protein tag into a FMD virus VP1 capsid protein results in the formation of a peptide bond between the N-terminal amino acid of the protein tag and a first amino acid of a protein of the FMD virus VP1 capsid protein or 2A protein fused thereto, as well as a peptide bond between the C-terminal amino acid of the tag and a second amino acid of the FMD virus VP1 capsid protein or 2A protein fused thereto, the second amino acid of the FMDV VP1 capsid protein or 2A protein fused thereto adjacent to the first amino acid of the FMDV VP1 capsid protein or 2A protein fused thereto.

As would be understood by those skilled in the art, an insertion as described above can be obtained through different approaches identifiable by a skilled person.

For example, in some embodiments, an insertion of a protein tag into a VP1 protein or 2A protein fused thereto can be performed at a protein level by first providing the VP1 protein or 2A protein fused thereto and the protein tag and then performing the insertion by breaking a peptide bond between two adjacent amino acids of the VP1 protein or 2A protein fused thereto and then forming new peptide bonds between the VP1 protein or 2A protein fused thereto and the protein tag, as described above. For example, the VP1 protein or 2A protein fused thereto can be digested with a protease to break a peptide bond between two adjacent amino acids in the VP1 protein or 2A protein fused thereto, followed by insertion of the protein tag between the previously adjacent amino acids of the VP1 protein or 2A protein fused thereto, for example using native chemical ligation methods known to those skilled in the art [15].

In some embodiments, a protein comprising the VP1 protein or 2A protein fused thereto with the protein tag inserted can be synthesized as single protein by design. Proteins can be synthesized using biosynthetic methods, such as cell-based methods or cell-free methods known to those skilled in the art. Protein biosynthesis can be performed by translation of DNA or RNA polynucleotides encoding the protein. Thus, protein biosynthesis can be performed by providing cell-based or cell-free protein translation systems with DNA or RNA polynucleotides encoding the protein. For example, protein biosynthesis can be performed in cells transfected with in vitro transcribed RNA encoding the protein (Example 2). Proteins can also be produced by liquid-phase or solid-phase chemical protein synthetic methods known to those skilled in the art [16].

In some embodiments, insertion of a protein tag into a VP1 protein can also be performed by fusion of the tag with two VP1 protein segments, for example where one protein, comprising a VP1 protein segment already having a protein tag at the N-terminal or C-terminal end, is "fused" to a second VP1 protein segment, with the result that the protein tag is covalently joined between the first and second VP1 protein segments.

In some embodiments, insertion of a protein tag in a VP1 protein or 2A protein fused thereto to obtain a genetically engineered VP1 protein can be performed at a polynucleotide level through to an in-frame insertion of a protein tag-coding polynucleotide in between two codons of a VP1 protein-coding polynucleotide, or in between two codons of a 2A protein fused thereto. An in-frame insertion can be performed in several steps, by first providing the VP1 coding and the protein tag-coding polynucleotides and performing the insertion by breaking a bond (typically a phosphodiester bond) between two adjacent nucleotide bases of the first polynucleotide and then forming new bonds between the VP1-coding polynucleotide and the protein tag-coding polynucleotide. For example, the VP1 coding polynucleotide can be digested with one or more restriction endonucleases and then the protein tag-coding polynucleotide inserted by ligation (e.g., using T7 DNA ligase) into compatible site(s) allowing formation of phosphodiester bonds between the first and second polynucleotide bases. Compatible DNA ligation sites can be "sticky" ends, digested with restriction endonuclease producing an overhang (e.g. EcoRI), or can be "blunt ends" with no overhang, as would be understood by those skilled in the art.

In some embodiments, the VP1-coding and the protein tag-coding polynucleotides can be provided within a single polynucleotide by design. For example, a tag can be added by inserting the polynucleotide encoding a protein of interest in a vector that has the tag ready to fuse at the N-terminus or C-terminus. The tag can be added using PCR primers encoding the tag; using PCR the tag can be fused to the N-terminus or C-terminus of the protein-coding polynucleotide, or can be inserted at an internal location, using internal epitope tagging [17], among other methods known to those skilled in the art. Other methods such as overlap extension PCR and infusion HD cloning can be used to insert a tag at a site between the N-terminus and C-terminus of a protein-coding polynucleotide (see Example 2). Optionally, a polynucleotide encoding a 'linker' (such as a sequence encoding a short polypeptide or protein sequence, e.g., gly-gly-gly or gly-ser-gly can be placed between the protein of interest and the tag; this can be useful to prevent the tag from affecting the activity of the protein being tagged.

Accordingly, in several embodiments, a protein can be tagged using standard molecular biology techniques suitable to be use for an insertion in the sense of the disclosure as would be understood by those skilled in the art. For example, a His-tag or other protein tag can be inserted in a protein of interest by cloning a polynucleotide encoding a protein of interest in a vector that has the tag ready to fuse at the N-terminus or C-terminus. The His-tag or other protein tags can be added using primers containing the tag; using PCR the tag can be fused to the N-terminus or C-terminus of the gene. Alternatively, methods such as overlap extension PCR and infusion HD cloning can be used to insert a tag at a site between the N-terminus and C-terminus of a protein-coding polynucleotide (see Example 2). Optionally, a linker (such as gly-gly-gly or gly-ser-gly) can be placed between the protein of interest and the 6 His tag. This can be used to prevent the polyhistidine tag from affecting the activity of the protein being tagged.

The choice of the location where a tag is added to a protein sequence depends mainly on the structural and functional features of a protein and the intended downstream methods employing the use of the tag.

In embodiments herein described, the insertion location of a protein tag in a genetically engineered VP1 protein of an FMDV virus is performed at insertion position selected to have the tag presented on the external surface-exposed position of the FMDV without compromising the integrity of the FDMV capsid.

The term "insertion point", "insertion site" or "insertion position" as used herein refers to the position into which a second protein is inserted into a first protein, and can be described relative to a reference amino acid in the first protein's amino acid sequence. In particular, an insertion point in engineered VP1 can be described as upstream (towards the N-terminus) or downstream (towards the C-terminus) with respect to the reference amino acid.

For example, in a protein sequence, a position adjacently upstream of the reference amino acid (removed 1 residue from the reference amino acid towards the N terminus) can be referred to as "−1", whereas a position adjacently downstream of the reference amino acid (removed 1 residue from the reference amino acid towards the C-terminus) can be referred to as "+1".

Examples of reference amino acids in a protein sequence are the N-terminus of a protein sequence or the C-terminus of a protein sequence. The term "N-terminus" of a protein sequence as used herein refers to an amino acid that is not covalently linked via its amino group to another amino acid of the same protein or of a same segment thereof. The term "C-terminus" of a protein sequence as used herein refers to an amino acid that is not covalently linked via its carboxyl group to another amino acid of the same protein or of a same segment thereof.

In embodiments described herein, the protein tag formed by up to 100 amino acids can be inserted at an insertion position selected from any one of position −1 to position +6 relative to the N-terminus of the 2A protein segment of the FMD virus, or from any one of position −1 to position −7 relative to the C-terminus of the VP1 protein segment of the FMD virus. The inserted protein tag residues will be presented on the viral capsid surface. Tag insertion site is a disordered (flexible) loop structure formed by the C-terminus of VP1 or 2A protein fused thereto, therefore by a protein tag insertion the length of an existing loop is extended and the conformation of tag-loop allows its surface exposure.

Figure 1C:
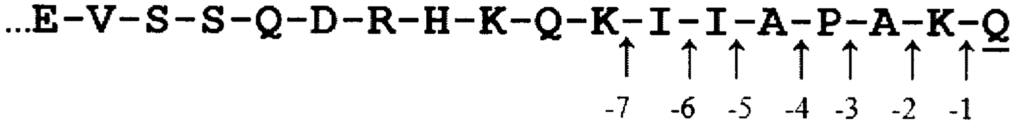
FIGS. 1C and 1D show positions of protein tag insertion sites relative to (FIG. 1C) C-terminus of protein VP1 and (FIG. 1D) N-terminus of FMDV protein 2A in exemplary FMDV $A_{24}$ Cruzeiro.
Figure 1D:
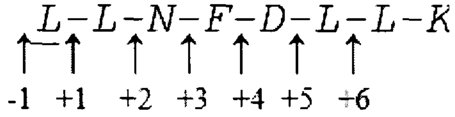

Diagrams of insertion points of some embodiments herein described are shown in FIGS. 1C and 1D, showing positions of protein tag insertion points relative to C-terminus of protein VP1 (FIG. 1C) and N-terminus of FMDV protein 2A (FIG. 1D) in exemplary FMDV $A_{24}$ Cruzeiro. In particular, FIGS. 1C and 1D shows examples of insertion sites relative to the C-terminus of protein VP1 and the N-terminus of FMDV protein 2A in exemplary FMDV $A_{24}$ Cruzeiro. For example, in the first exemplary genetically engineered FMDV, $A_{24}$ FMD $2A_{6H}$, insertion of the sequence HHHHHHKQ (SEQ ID NO:16) is at position −1 relative to the N-terminus of FMDV protein 2A. In this exemplary genetically engineered FMDV, the insertion of the tag results in the N-terminus of the tag forming a peptide bond with the carboxyl group of the C-terminal amino acid Q (underlined in FIG. 1C) of the VP1 segment, and the C-terminus of the tag forming a peptide bond with the amino group of the L (underlined in FIG. 1D) at the N-terminus of the 2A protein segment. In the second exemplary genetically engineered FMDV, $A_{24}$ FMDV $P1_{6H}$, the sequence HHHHHHIIAPAK (SEQ ID NO:17) was inserted at position −1 relative to the C-terminus of VP1 (position 210 of VP1). In this exemplary genetically engineered FMDV, the insertion of the tag results in the N-terminus of the tag forming a peptide bond with the carboxyl group of the K adjacently upstream of the C-terminal Q (underlined in FIG. 1C) of the VP1 protein segment, and the C-terminus of the tag forming a peptide bond with the amino group of the C-terminal Q (underlined in FIG. 1C) of the VP1 protein segment.

In some embodiments, the genetically modified VP1 protein is engineered to include a protein tag formed by up to 100 amino acids at an insertion position selected from any one of position −1 to position −7 relative to the C-terminus of the FMD VP1 protein.

In some embodiments, the genetically modified VP1 protein can be engineered to fuse the N-terminus of the 2A protein to the C-terminus of the VP1 protein and to include a protein tag formed by up to 100 amino acids at an insertion position selected from any one of position −1 to position +6 relative to the N-terminus of the 2A protein, or at an insertion position selected from any one of position −1 to position −7 relative to the C-terminus of the VP1 protein.

The term "fused" as used herein in relation to two proteins or related segments refers to a state of being covalently linked via a peptide bond, or two polynucleotides being covalently linked, typically via a phosphodiester bond. In particular, as used herein in some embodiments, FMD virus protein VP1 is said to be fused to FMD virus protein 2A, wherein the C-terminus of protein VP1 is covalently linked to the N-terminus of protein 2A via a peptide bond.

In some embodiments, the tag is comprised in a genetically modified VP1 protein of the FMD virus engineered so that the N-terminus of the 2A protein is fused to the C-terminus of the VP1 protein, wherein a 3Cpro cleavage site is absent, and wherein the tag is inserted at an insertion position selected from any one of position −1 to position +6 relative to the N-terminus of the 2A protein segment of the FMD virus, or from any one of position −1 to position −7 relative to the C-terminus of the VP1 protein segment of the FMD virus. In these embodiments, the sequence of the inserted protein tag eliminates the 3Cpro cleavage site, abolishing 3Cpro-mediated cleavage of the 2A protein from the VP1 protein, resulting in a non-cleaved VP1-2A fusion protein. An exemplary tagged VP1-2A fusion protein described herein comprises the genetically modified VP1 protein comprised in the exemplary genetically engineered FMDV, $A_{24}$ FMD $2A_{6H}$, where insertion of the sequence HHHHHHKQ (SEQ ID NO:16) at position −1 relative to the N-terminus of FMDV protein 2A abolished the 3Cpro cleavage site. In embodiments wherein the tag is inserted into the 2A protein sequence, a 3Cpro cleavage site is absent to prevent cleavage of the 2A protein segment comprising the tag from the VP1 protein In embodiments described herein, a 3Cpro cleavage site means a cleavage site between the C-terminal amino acid of FMDV protein VP1 and the N-terminal amino acid of FMDV protein 2A. An exemplary 3Cpro cleavage site in exemplary FMDV $A_{24}$ Cruzeiro is PAKQLLNFDL (SEQ ID NO:40), wherein 3Cpro-mediated cleavage occurs at the site "↓" shown in FIG. 1A.

In some embodiments, the tag is comprised in a genetically modified VP1 protein of the FMD virus engineered with an insertion of a protein tag located at an insertion position selected from any one of position −1 to position −7 relative to the C-terminus of the VP1 protein. In these embodiments, the sequence of the inserted protein tag preserves the $3C^{pro}$ cleavage site, enabling $3C^{pro}$-mediated cleavage of the 2A protein from the VP1 protein, resulting in a VP1 protein that lacks protein 2A. An exemplary tagged VP1 protein described herein comprises the genetically modified VP1 protein comprised in the exemplary genetically engineered FMDV, $A_{24}$ FMDV $P1_{6H}$, wherein the insertion of the sequence HHHHHHIIAPAK (SEQ ID NO:17) at position −1 relative to the C-terminus of VP1 preserves the $3C^{pro}$ cleavage site. In this example, the sequence IIAPAKQ (SEQ ID NO:39) follows the 6×His residues to preserve $3C^{pro}$ cleavage at the VP1-2A junction. However, as shown in the exemplary genetically engineered FMDV, $A_{24}$ FMD $2A_{6H}$, a $3C^{pro}$ cleavage site is not necessary as $3C^{pro}$ cleavage is not required for FMD virus viability.

Tags such as 6 consecutive histidine residues (6×-His) and other protein tags can be used for affinity purification and concentration of recombinant proteins using ion affinity chromatography supports, e.g. $Ni^{2+}$ or $Co^{2+}$ beads or affinity columns, and also can be used for binding to other substrates such as nanolipoproteins particles presenting chelated $Ni^{2+}$ ions (NiNLP) enabling new strategies for enhancing immunogenicity, among other applications known to those skilled in the art and disclosed herein. Primary protein sequence information and structural modeling can be used to predict the three-dimensional location of an inserted tag. For example, protein crystal structure can be visualized using software such as Pymol Viewer, among others known to those skilled in the art.

In some embodiments, a genetically modified FMD virus is provided comprising a genetically engineered VP1 protein according to an embodiment herein described. In some embodiments, the genetically modified FMDV comprises a 6×-His tag-bearing mutant FMD virus.

In particular, in some embodiments, the genetically modified FMD virus has a viral capsid comprising a genetically modified VP1 protein, wherein the VP1 protein of the FMD virus is engineered to fuse at a C-terminus of the VP1 protein, a His tag formed by a HIS segment of sequence HHHHHHKQ (SEQ ID NO: 16) or another protein tag, and a 2A protein of the FMDV virus. In the HIS-tag of the genetically modified VP1 protein, the 2A protein is fused to the C-terminus of the HIS segment. In the genetically modified FMD virus, the HIS-tag or the another protein tag, of the modified VP1 protein is presented on an external surface of the viral capsid. An exemplary embodiment of this modified FMDV is referred to herein as $A_{24}$ FMD $2A_{6H}$. In other embodiments, the genetically modified FMD virus has a viral capsid comprising a modified VP1 protein, wherein the VP1 protein of the FMD virus is engineered to insert a HIS tag having sequence HHHHHHIIAPAK (SEQ ID No: 17) at position 210 of the VP1 protein. In the genetically modified FMD virus, the HIS-tag of the modified VP1 protein is presented on an external surface of the viral capsid. An exemplary embodiment of this modified FMDV is referred to herein as $A_{24}$ FMDV $P1_{6H}$. The two mutant 6×His FMDV are designed to express 60 copies of 6×His tags decorating the viral capsid, but the location of the His tag differs in the two mutants. To design the mutant constructs, the structural model of the FMDV A24 capsid was generated by homology modeling using the crystal structure of FMDV O1 BFS serotype (PDB, 1FOD) [18]. The structure was visualized on Pymol Molecular Viewer and analyzed for surface-exposed residues/stretches. The structural analysis revealed that the C-terminus of VP1 is largely surface-exposed and composed of variable residues indicating that insertions placed in this region are unlikely to negatively impact the capsid structure. An insertion was preferred in the design of these viruses, rather than substitutions in the VP1 C-term residues, in order to minimize alteration of the actual viral sequences in this region.

Tolerance for insertion of short tags in the conformationally flexible. FMDV VP1 G-H loop, such as FLAG, HA and 6×His tags has previously been reported [9, 10, 19, 20]. In particular, histidine tag insertions at amino acid position 9 downstream the VP1 RGD (RGD+9) and FLAG at position 8 downstream of (RGD+8) rendered viable viruses [1.0, 19, 20]. Although the aforementioned studies reported the preservation of virus infectivity and detection of tag expression, the appearance of two alternate forms of FLAG tag in the FLAG tagged FMDVs and a threonine to arginine (T to R) mutations at 158 of VP1 in HA tagged FMDVs have been also documented.

In some embodiments, to generate the first exemplary genetically engineered FMDV, $A_{24}$ FMD $2A_{6H}$, insertion of the sequence HHHHHHKQ (SEQ ID NO:16) in 2A in this infectious cDNA clone results in a mutant FMDV genome in which the mutated 2A protein is fused at C-terminus of VP1 on the capsid exposed surface. This modification produced a mutant virus capsid wherein 2A contains the HHHHHHKQ (SEQ ID NO:16) tag. There is precedent in the literature [21] for the tolerance of FMDV to contain a modified 2A protein as part of the capsid structure and still be able to infect cell lines and give productive infections in the natural host [21]. A major difference in the construct design described herein is that the FMDV 2A is modified with the 6×-His tag insertion toward the N-terminus. The FMDV capsid is composed of 60 copies of VP1; therefore, the capsid of the mutant $A_{24}$ FMD $2A_{6H}$ virus is decorated with 60 6×-His sequences. $A_{24}$ FMDV $P1_{6H}$, the second exemplary mutant virus, carries the 6×His tag insertion within the C-terminus sequence of VP1; the amino acid sequence HHHHHHIIAPAK (SEQ ID NO:17) was inserted at position 210 of VP1. This mutant was engineered to maintain the cleavage site amino acid sequence at the VP1-2A junction which is hydrolyzed by viral proteinase $3C^{pro}$. The mutant virus carries 60 copies of 6×-His tag within the VP1 and has no 2A protein fused to the capsid; it more closely resembles the natural capsid form having no 2A attached but with the 6×His insertion in VP1 C-terminus.

As will be apparent from the present disclosure, the exemplary $A_{24}$ FMD $2A_{6H}$ and $A_{24}$ FMDV $P1_{6H}$ FMDV virus constructs display the following characteristics: (1) a fully viable virus presenting a 6×-His tag fused to either VP1 or 2A ($A_{24}$ FMDV $P1_{6H}$ or FMDV $2A_{6H}$, respectively); (2) both 6×-His tagged viruses capable of binding divalent cations such as $Ni^{2+}$ and $Co^{2+}$ thus allowing for one step purification using an ion affinity chromatography (IAC); (3) both 6×-His tagged viruses recognized by anti-His antibody and capable of binding to $Ni^{2+}$-coated plates with potential for use as a diagnostic; (4) other 6×-His-tagged FMDV serotypes are easily made using conveniently located unique restriction sites that are engineered into the viral genome and that flank the capsid coding region in the $A_{24}$Cru backbone (cassette design); (5) 6×-His tagged viruses capable of binding NiNLP/MPLA nanoconstructs [22] and possibly improving FMDV vaccine efficacy 6) more specifically, bromo ethyleneimine (BEI)-inactivated mutant $A_{24}$ FMDV $P1_{6H}$-NiNLP-MPLA formulation might be effective as a vaccine formulation in FMDV animal model challenge studies compared to/with parental (wild type, WT) $A_{24}$ FMDV. In a mouse model of FMDV described herein, it is shown that percentage of survival after lethal challenge with FMDV $A_{24}$Cru improves in animals vaccinated with low doses (0.025 ug/animal) BEI-inactivated mutant $A_{24}$ FMDV $P1_{6H}$ formulated with NiNLP-MPLA as compared with animals vaccinated with the same dose of BEI-inactivated $A_{24}$ FMDV $P1_{6H}$ virus alone. These results indicate that exemplary formulation of FMDV $P1_{6H}$-Ni-NLP-MPLA has potential as an improved vaccine against FMD.

The exemplary 6×-His tagged FMDVs display growth characteristics similar to the parental WT-$A_{24}$ FMDV and are able to bind to complex molecules such as nickel (Ni) substrate-containing nanolipoprotein particles (NLP) further comprising adjuvants such as MLPA (NiNLP-MPLA) that are visualized by electron microscopy (EM) and detected by His-specific antibodies. These mutant viruses can be purified in one step by using a $Co^{2+}$-charged affinity supports (e.g. Co-beads or Co-affinity columns) with up to 95% recovery of infectious viral particles. Remarkably a BEI-inactivated 6×His mutant $A_{24}$ FMDV $P1_{6H}$ formulated with nanolipoproteins conjugated with an MPLA adjuvant (Ni-NLP-MPLA) was shown to be an effective vaccine using a validated FMD mouse model. In particular, animals vaccinated with the mutant virus conjugated with NiNLP-MPLA developed significant levels of neutralizing antibodies at 7 dpv and showed a boost after challenge. Similar vaccine potency study is expected with the $A_{24}$ FMDV $P1_{6H}$ formulated with either Ni-NLP-MPLA or a commercially available adjuvant (Sepic ISA-206) in cattle, a FMDV natural host.

The presence of multiple copies of 6×-His decorating the FMDV capsid surface allows the mutant viruses to attach to nickel-coated ELISA plates. As described herein, binding of 6×His $A_{24}$ viruses to these plates could be disrupted in a concentration-dependent manner suggesting that addition of Ni-NLP was competitive. Similarly, 6×His mutant virus attachment to Ni and Co complex particles (NiNLP-MPLA, Co-beads and Co-columns) is also described herein.

In some embodiments, a genetically modified VP1 protein of a FMD virus is provided. In a particular embodiment, the genetically modified VP1 protein is a VP1 protein of the FMD virus genetically engineered to fuse at a C-terminus of the VP1 protein a HIS tag at formed by a HIS segment of sequence HHHHHHKQ (SEQ ID NO: 16) and a 2A protein of the FMDV virus fused at a C-terminus of the HIS segment; an exemplary genetically modified VP1 protein comprises the VP1 of FMDV $2A_{6H}$. In another particular embodiment, the genetically engineered VP1 protein is a VP1 protein of the FMD virus engineered to insert a HIS tag having sequence HHHHHHIIAPAK (SEQ ID No: 17) at position 210 of the VP1 protein; an exemplary genetically modified VP1 protein comprises the VP1 of FMDV $P1_{6H}$. According to these embodiments, it is expected that a genetically engineered FMDV VP1 comprising a tag can be produced using recombinant viral protein production techniques. For example, a polynucleotide encoding a genetically engineered VP1 can be used to express an isolated sequence encoding an engineered FMDV VP1 protein, for example in cell culture, or in a cell-free expression system.

The approaches, configurations and methods described with reference to the exemplary HIS tag and related insertion points can be applied to other protein tags in accordance with the guidance provided by the instant disclosure as will be understood by a skilled person.

In some embodiments, a genetically engineered polynucleotide is provided encoding one or more of the engineered FMD viruses and/or genetically modified VP1 protein herein described.

The term "polynucleotide" or "polynucleotide molecule" as used herein indicates an organic polymer composed of two or more monomers including nucleotides, or analogs thereof. The isoelectric point of a polynucleotide in the sense of the disclosure is less than 7 as will be understood by a skilled person. The term "nucleotide" refers to any of several compounds that consist of a ribose or deoxyribose sugar joined to a purine or pyrimidine base and to a phosphate group and that is the basic structural unit of nucleic acids. The term "nucleotide analog" refers respectively to a nucleotide in which one or more individual atoms have been replaced with a different atom or with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide.". In particular, polynucleotides in the sense of the disclosure comprise biological molecules comprising a plurality of nucleotides. Exemplary nucleic acids include deoxyribonucleic acids, ribonucleic acids, and synthetic analogues thereof, including peptide nucleic acids. Polynucleotides can typically be provided in single-stranded form or double-stranded form and in liner or circular form as will be understood by a person of ordinary skill in the art.

In some embodiments herein described, the polynucleotide is a DNA molecule that can be in a linear or circular form, and encodes the desired polypeptide under the control of a promoter specific to an enzyme such as an RNA polymerase, that is capable of transcribing the encoded portion of the DNA.

The isolated polynucleotide molecules of the present disclosure encode FMD viruses or VP1 proteins that can be used to prepare chemically inactivated vaccines using art-recognized methods for protecting cattle and swine from infection by a FMDV, as described in further detail below. Furthermore, these isolated polynucleotide molecules are useful because they can be mutated using molecular biology techniques to encode genetically-modified FMD viruses useful, inter alia, as vaccines for protecting cattle and swine from FMD infection. Such genetically-modified FMD viruses, as well as vaccines comprising them, are described in further detail below. In addition to targeted mutagenesis by recombinant techniques random approaches such as chemical treatment or use of error prone DNA polymerases can also be used for virus attenuation, or antigenic modification.

Accordingly, the present disclosure further provides a method for making a genetically modified FMDV, which method comprises mutating the DNA sequence encoding an infectious RNA molecule which encoding a genetically modified FMDV in accordance with the present disclosure, and expressing the genetically modified FMDV using a suitable expression system. A FMDV, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro. Furthermore, FMD virus like particle production in plants, insect cells, yeast and virus vectors such as adenovirus are other alternatives that can provide additional flexibility of producing high quantity recombinant preparations that can be explored further.

In several embodiments, one or more tagged FMD viruses can be provided by methods and/or systems herein described. In particular, in some embodiments, a method is described that comprises genetically engineering a FMD virus comprising a VP1 protein to fuse a HIS tag formed by a HIS segment of sequence HHHHHHKQ (SEQ ID NO: 16), or another protein tag, at a C-terminus of the VP1 protein and to fuse a 2A protein of the FMDV virus at a C-terminus of the HIS segment, or genetically engineering a FMD virus comprising a VP1 protein to insert a HIS segment having sequence HHHHHHIIAPAK (SEQ ID No: 17) or another protein tag, at position 210 of the VP1 protein or at another insertion position of the present disclosure.

The system comprises at least one polynucleotide encoding for at least one of HIS tag formed by a HIS segment of sequence HHHHHHKQ (SEQ ID NO: 16) and HIS tag having sequence HHHHHHIIAPAK (SEQ ID No: 17) and/or another protein tag in accordance with the present disclosure, and reagents for the introduction of the at least one polynucleotide in the FMDV virus. Site directed mutagenesis and overlap-extension PCR can be utilized to introduce or delete sequences amenably in FMDV and in many other viruses.

Production and manipulation of the isolated polynucleotide molecules described herein are within the skill in the art and can be carried out according to recombinant techniques described, inter alia, in Sambrook et al. 1989. *Molecular Cloning: A Laboratory Manual,* 2d ed., Cold Spring Harbor Laboratory Press, Cold Spring Harbor, N.Y. [23] and ref: Innis et al. (eds). 1995. *PCR Strategies*, Academic Press, Inc., San Diego, [24] which are incorporated herein by reference.

The present disclosure provides vectors comprising genetically modified nucleic acid sequences that encode genetically modified infectious RNA molecules that encode genetically modified Foot and Mouth Disease (FMD) Viruses. Viral vectors such as adenovirus or ms2-phage, VSV, NDV can be utilized to express tagged capsids, virus like particles and sub unit vaccines as suitable.

In particular, the instant disclosure provides isolated polynucleotide molecules encoding genetically modified infectious RNA molecules that encode genetically modified FMD viruses; for example, the vaccine candidate viruses $A_{24}$ FMDV $P1_{6H}$ and $A_{24}$ FMDV $2A_{6H}$.

It is understood that terms herein referring to nucleic acid molecules such as "isolated polynucleotide molecule" and "nucleotide sequence" include any polynucleotides such as DNA and RNA molecules and include both single-stranded and double-stranded molecules whether it is natural or synthetic origin.

For example, SEQ ID NO:1 is a DNA sequence corresponding to the genetically modified RNA genome of a genetically modified FMDV. Thus, a DNA sequence complementary to the DNA sequence set forth in SEQ ID NO:1 is a template for, is complementary to or "encodes", the RNA genome of the FMD virus (RNA that encodes the FMDV) and in particular, an infectious RNA molecule.

An "infectious RNA molecule", for purposes of the present disclosure, is an RNA molecule that encodes the necessary elements for viral replication, transcription, and translation into a functional virion in a suitable host cell.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present disclosure can be transformed or transfected. "Suitable host cells" for transfection with such RNA molecules, isolated polynucleotide molecules, or viral vectors, comprise mammalian, particularly bovine, hamster (e.g. BHK-21 cell line) and porcine cells, and are described in further detail below.

In some embodiments, the polynucleotide of the FMDV can be a homolog of SEQ ID NO: 1. For purposes of the present disclosure, two nucleotide (RNA or DNA) sequences are substantially homologous when at least 80% (preferably at least 85% and most preferably at least 90%) of the nucleotides match over the defined length of the sequence using algorithms such as CLUSTAL or PHILIP. Sequences that are substantially homologous can be identified in a Northern hybridization experiment under stringent conditions as is known in the art. See, for example, Sambrook et al. [23]. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant disclosure such as deletion or insertion of nucleotides that do not substantially affect the functional properties of the resulting transcript. It is therefore understood that the disclosure encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, can be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) can comprise the steps of: constructing an isolated polynucleotide of the present disclosure or an isolated chimeric gene of the present disclosure; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

High-resolution crystal structures for several FMDV strains, such as FMDV O1 BFS serotype (PDB, 1FOD) [18]

are available in databases such as Protein Databank, and others known to those skilled in the art. Thus, polynucleotides encoding homologs of FMDV described herein that are capable of properly folding and maintaining an icosahedral virion structure can be determined by visualizing the crystal structure of FMDV homologs using programs such as Pymol Molecular Viewer and others, as would be understood by persons skilled in the art. The structure of FMDV is also described in published articles such as Fry et al., 1990 [25].

Moreover, substantially similar nucleic acid fragments can also be characterized by their ability to hybridize. Estimates of such homology are provided by DNA-DNA, DNA-RNA, or RNA-RNA hybridization under conditions of stringency as is well understood by those skilled in the art [26]. Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a modified FMDV, for example, $A_{24}$ FMDV $2A_{6H}$ (SEQ ID NO:1) and $A_{24}$ FMDV $P1_{6H}$ (SEQ ID NO:3) and which hybridize under stringent conditions, as described herein, to the exemplary modified FMDVs, $A_{24}$ FMDV $2A_{6H}$ and $A_{24}$ FMDV $P1_{6H}$ sequences disclosed herein, (SEQ ID NO:1, SEQ ID NO:3), or to fragments thereof, are encompassed by the present disclosure.

Substantially similar nucleic acid fragments of the instant disclosure can also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller [27], the local homology algorithm of Smith et al. [28]; the homology alignment algorithm of Needleman and Wunsch [29]; the search-for-similarity-method of Pearson and Lipman [30]; the algorithm of Karlin and Altschul [31], modified as in Karlin and Altschul [32].

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or sub-genomic sequence, or the complete cDNA or gene sequence. A reference sequence can comprise, for example, a sequence identifiable a database such as GenBank and others known to those skilled in the art.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970) [29].

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

By "variants" substantially similar sequences are intended. For nucleotide sequences, conservative variants include those sequences that, because of the degeneracy of the genetic code, can encode the exemplary $A_{24}$ FMDV $2A_{6H}$ and $A_{24}$ FMDV $P1_{6H}$ sequences, the amino acid sequences of the disclosure. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the disclosure will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present disclosure are biologically active, that is they possess the desired biological activity, that is, a modified $A_{24}$ FMDV $2A_{6H}$ and/or $A_{24}$ FMDV $P1_{6H}$ activity. Such variants may result from, for example, genetic polymorphism or from human manipulation. Biologically active variants of modified $A_{24}$ FMDV $2A_{6H}$ and $A_{24}$ FMDV $P1_{6H}$ activities of the disclosure will have at least about 90%, preferably at least about 95%, and more preferably at least about 98% sequence identity to the amino acid sequence for the native protein as determined by sequence alignment programs described elsewhere herein. A biologically active variant of a protein of the disclosure may differ from that protein by as few as 1-15 amino acid residues, or even 1 amino acid residue.

The polypeptides of the disclosure can be altered in various ways including amino acid substitutions, deletions, truncations, and insertions. Novel proteins having properties of interest can be created by combining elements and fragments of proteins of the present disclosure, as well as with other proteins. Methods for such manipulations are generally known in the art. Thus, the genes and nucleotide sequences of the disclosure include both the naturally occurring sequences as well as mutant forms. Likewise, the proteins of the disclosure encompass naturally occurring proteins as well as variations and modified forms thereof. Such variants will continue to possess the desired modified $A_{24}$ FMDV $2A_{6H}$ and/or $A_{24}$ FMDV $P1_{6H}$ activities. The mutations that will be made in the DNA encoding the variant does not place the sequence out of reading frame and preferably will not disrupt secondary mRNA structure with potential involvement as cis-actin elements of the viral genome.

In particular, variants of FMDV described herein can include those comprising mutations in regions of the FMDV genome that do not encode highly conserved mRNA structure, thus indicating that the RNA structure of these regions is not predicted to have any role in other viral biological functions. RNA structure can be predicted from primary RNA sequence using programs such as Mfold web server v.2.3 [33] among others known to those skilled in the art.

The term "open reading frame", or "ORF", as used herein, means the minimal nucleotide sequence required to encode a particular FMDV protein without an intervening stop codon.

Accordingly, the instant disclosure relates to any nucleic acid fragment comprising a nucleotide sequence that encodes all or a substantial portion of the amino acid sequences set forth herein considering codon degeneracy. "Codon degeneracy" refers to divergence in the genetic code permitting variation of the nucleotide sequence without affecting the amino acid sequence of an encoded polypeptide.

As used herein, unless otherwise indicated, "coding regions" refer to those sequences of RNA from which FMDV proteins are expressed, and also refer to cDNA that encodes such RNA sequences. Likewise, "ORFs" refer both to RNA sequences that encode FMDV proteins and to cDNA sequences encoding such RNA sequences.

It is furthermore to be understood that the isolated polynucleotide molecules and the isolated RNA molecules of the present disclosure include both synthetic molecules and molecules obtained through recombinant techniques, such as by in vitro cloning and transcription.

In some embodiments, a polynucleotide is provided encoding one or more FMDV cDNA clones that further comprise unique restriction endonuclease sites that facilitate the exchange of DNA cassettes representing relevant capsid coding regions of other FMDV strains/serotypes and subtypes of FMDV field isolates. Other FMDV strains/serotypes and subtypes of FMDV field isolates are identifiable by those skilled in the art, such as those described in Rieder et al. (1993) and Uddowla et al. (2012) [34, 35]. For example, exemplary unique restriction sites R1 and R2 in FIG. 1B corresponding to unique PflMI and NheI restriction endonuclease sites can be used for the exchange of polynucleotide sequences encoding capsids by those of other serotypes for development of novel vaccines comprising tagged FMDV of other strains/serotypes and subtypes. In these embodiments, restriction endonuclease digest reactions comprising the appropriate restriction enzymes (for example PflMI and NheI) can be used to excise the region of a polynucleotide encoding a genetically engineered tagged FMDV VP1 flanked by the restriction sites, and this region can be thereafter ligated into a similarly restriction-digested polynucleotide encoding a different FMDV strain/serotype or subtype, thereby generating a new polynucleotide encoding an engineered FMDV strain/serotype or subtype comprising the tagged VP1. Techniques for performing such restriction digests and ligation of polynucleotides are known to those skilled in the art.

In some embodiments, an FMDV functionalized nanolipoprotein particle is provided. The term "nanolipoprotein particle" "nanodisc" "rHDL" or "NLP" as used herein indicates a supramolecular complex formed by a membrane forming lipid arranged in a lipid bilayer stabilized by a scaffold protein. The membrane forming lipids and scaffold protein are components of the NLP. In particular, the membrane forming lipid component is part of a total lipid component, (herein also membrane lipid component or lipid component) of the NLP together with additional lipids such as functionalized lipids and/or lysolipids, that can further be included in the NLPs as will be understood by a skilled person upon reading of the present disclosure. The scaffold protein component is part of a protein component of the NLP together with additional proteins such as membrane proteins, target proteins and other proteins that can be further included as components of the NLPs as will be understood by a skilled person upon reading of the present disclosure. Additional components can be provided as part of the NLP herein described as will be understood by a skilled person. In particular, the membrane lipid bilayer can attach membrane proteins or other amphipathic compounds through interaction of respective hydrophobic regions with the membrane lipid bilayer. The membrane lipid bilayer can also attach proteins or other molecule through anchor compounds or functionalized lipids as will be understood by a skilled person upon reading of the disclosure. In a nanolipoprotein particle, the membrane lipid bilayer can be confined in a discoidal configuration by the scaffold protein. Predominately discoidal in shape, nanolipoprotein particles typically have diameters between 5 to 25 nm, share uniform heights between 3 to 6 nm and can be produced in yields ranging between 30 to 90%.

In particular, in embodiments herein described the nanolipoprotein particle can be formed by a lipid bilayer confined in a discoidal configuration by a scaffold protein. In this configuration, the lipid bilayer confined by the scaffold protein can be 3-6 nanometers in thickness, the nanolipoprotein particle can have an overall diameter of 5-25 nanometers, and the scaffold protein on the particle can have a thickness of 1-2 nanometers. In some embodiments, an entire NLP structure can be up to 600 kilodaltons in weight.

The particular membrane forming lipid, scaffold protein, the lipid to protein ratio, and the assembly parameters determine the size and homogeneity of nanolipoprotein particles as will be understood by a skilled person. In the nanolipoprotein particle the membrane forming lipid are typically arranged in a membrane lipid bilayer confined by the scaffold protein in a discoidal configuration as will be understood by a skilled person.

The term "membrane forming lipid" or "amphipathic lipid" as used herein indicates a lipid possessing both hydrophilic and hydrophobic moieties that in an aqueous environment assembles into a lipid bilayer structure that consists of two opposing layers of amphipathic molecules know as polar lipids. Each polar lipid has a hydrophilic moiety, such a polar group such as, a derivatized phosphate or a saccharide group, and a hydrophobic moiety, such as a long hydrocarbon chain. Exemplary polar lipids include phospholipids, sphingolipids, glycolipids, ether lipids, sterols, alkylphosphocholines and the like. Amphipathic lipids include but are not limited to membrane lipids, such as amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC).

The term "scaffold protein" as used herein indicates any amphipathic protein that is capable of self-assembly with amphipathic lipids in an aqueous environment, organizing the amphipathic lipids into a bilayer disc, and comprise apolipoproteins, lipophorins, derivatives thereof (such as truncated and tandemly arrayed sequences) and fragments thereof (e.g. peptides) which maintains the amphipathic nature and capability of self-assembly, such as apolipoprotein E4 (22Kd fragment), lipophorin III, apolipoprotein A-1 and the like. In general, scaffold proteins have an alpha helical secondary structure in which a plurality of hydrophobic amino acids form a hydrophobic face and a plurality of hydrophilic amino acids form an opposing hydrophilic face. In some embodiments, rationally designed amphipathic peptides and synthetic apolipoproteins which maintain an amphipathic structure and capability of self-assembly can serve as a scaffold protein of the NLP.

The term "apolipoprotein" as used herein indicates an amphipathic protein that binds lipids to form lipoproteins. The term "amphipathic" pertains to a molecule containing both hydrophilic and hydrophobic properties. Exemplary amphipathic molecules comprise molecules having hydrophobic and hydrophilic regions/portions in its structure. Examples of biomolecules which are amphipathic include but not limited to phospholipids, cholesterol, glycolipids, fatty acids, bile acids, saponins, and additional lipids identifiable by a skilled person. A "lipoprotein" as used herein indicates a biomolecule assembly that contains both proteins and lipids. In particular, in lipoproteins, the protein component surrounds or solubilizes the lipid molecules enabling particle formation. Exemplary lipoproteins include the plasma lipoprotein particles classified under high-density (HDL) and low-density (LDL) lipoproteins, which enable fats and cholesterol to be carried in the blood stream, the transmembrane proteins of the mitochondrion and the chloroplast, and bacterial lipoproteins. In particular, the lipid components of lipoproteins are insoluble in water, but because of their amphipathic properties, apolipoproteins such as certain Apolipoproteins A and Apolipoproteins B and other amphipathic protein molecules can organize the lipids in a bilayer orientation with exposed hydrophilic moieties, creating the lipoprotein particle that is itself water-soluble, and can thus be carried through water-based circulation (e.g. blood, lymph in vivo or in vitro). Apolipoproteins known to provide the protein components of the lipoproteins can be divided into six classes and several sub-classes, based on the different structures and functions. Exemplary apolipoprotein known to be able to form lipoproteins comprise Apolipoproteins A (apo A-I, apo A-II, apo A-IV, and apo A-V), Apolipoproteins B (apo B48 and apo B100), Apolipoproteins C (apo C-I, apo C-II, apo and apo C-IV), Apolipoproteins D, Apolipoproteins E, and Apolipoproteins H. For example, apolipoproteins B can form low-density lipoprotein particles, and have mostly beta-sheet structure and associate with lipid droplets irreversibly, while Apolipoprotein A1 comprise alpha helices and can associate with lipid droplets reversibly forming high-density lipoprotein particles.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In embodiments herein described, NLPs comprise different types of scaffold protein and a lipid component membrane forming lipids and possibly other lipids, in ratios and proportions that would be identifiable by a skilled person upon reading of the present disclosure.

In some embodiments, the membrane forming lipids component of the lipid component lipids such as phospholipids, preferably including at least one phospholipid, typically soy phosphatidylcholine, egg phosphatidylcholine, soy phosphatidylglycerol, egg phosphatidylglycerol, palmitoyl-oleoyl-phosphatidylcholine distearoylphosphatidylcholine, or distearoylphosphatidylglycerol. Other useful phospholipids include, e.g., phosphatidylcholine, phosphatidylglycerol, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, stearoyl-palmitoyl-phosphatidylcholine, di-palmitoyl-phosphatidyl ethanolamine, distearoyl-phosphatidylethanolamine, di-myrstoyl-phosphatidylserine, and dioleyl-phosphatidylcholine.

Additionally exemplary membrane forming lipids that can be comprised in various combinations together with one or more lysolipids comprise 1,2-dipalmitoyl-sn-glycero-3-phosphocholine, 1,2-dimyristoyl-sn-glycero-3-phosphocholine, 1,2-dilauroyl-sn-glycero-3-phosphocholine, 1,2-didecanoyl-sn-glycero-3-phosphocholine, 1,2-di erucoyl-sn-glycero-3-phosphocholine, 1,2-dioleoyl-sn-glycero-3-phosphocholine, 1,2-dipalmitoleoyl-sn-glycero-3-phosphocholine, 1,2-dimyristoleoyl-sn-glycero-3-phosphocholine, 1-stearoyl-2-oleoyl-sn-glycero-3-phosphocholine, 1-stearoyl-2-myristoyl-sn-glycero-3-phosphocholine, 1-palmitoyl-2-oleoyl-sn-glycero-3-phosphocholine, egg phosphatidylcholine extracts, soy phosphatidylcholine extracts, heart phosphatidylcholine extracts, brain phosphatidylcholine extracts, liver phosphatidylcholine extracts, 1,2-distearoyl-sn-glycero-3-phosphate, 1,2-dipalmitoyl-sn-glycero-3-phosphate, 1,2-dimyristoyl-sn-glycero-3-phosphate, 1,2-dilauroyl-sn-glycero-3-phosphate, 1-palmitoyl-2-oleoyl-sn-glycero-3-phosphate, 1-stearoyl-2-oleoyl-sn-glycero-3-phosphate, 1,2-dipalmitoyl-sn-glycero-3-phosphoethanolamine, 1,2-dimyristoyl-sn-glycero-3-phosphoethanolamine, 1,2-dilauroyl-sn-glycero-3-phosphoethanolamine, 1,2-dioleoyl-sn-glycero-3-phosphoethanolamine, 1,2-dipalmitoleoyl-sn-glycero-3-phosphoethanolamine, Egg phosphatidylethanolamine extract, soy phosphatidylethanolamine extract, heart phosphatidylethanolamine extract, brain phosphatidylethanolamine extract, 1,2-distearoyl-sn-glycero-3-phospho-(1'-rac-glycerol), 1,2-dioleoyl-sn-glycero-3-phospho-(1'-rac-glycerol), 1,2-dipalmitoyl-sn-glycero-3-phospho-(1'-rac-glycerol), 1,2-dimyristoyl-sn-glycero-3-phospho-(1'-rac-glycerol), 1,2-dilauroyl-sn-glycero-3-phospho-(1'-rac-glycerol), 1-palmitoyl-2-oleoyl-sn-glycero-3-phospho-(1'-rac-glycerol), egg phosphatidylglycerol extract, soy phosphatidylglycerol extract, 1,2-distearoyl-sn-glycero-3-phospho-L-serine, 1,2-dioleoyl-sn-glycero-3-phospho-L-serine, 1,2-dipalmitoyl-sn-glycero-3-phospho-L-serine, 1,2-dimyristoyl-sn-glycero-3-phospho-L-serine, 1,2-dilauroyl-sn-glycero-3-phospho-L-serine, 1-palmitoyl-2-oleoyl-sn-glycero-3-phospho-L-serine, soy phosphatidylserine extract, brain phosphatidylserine extract, 2-((2,3-bis(oleoyloxy)propyl)dimethylammonio)ethyl hydrogen phosphate, cholesterol, ergosterol, sphingolipids, ceramides, sphingomyelin, gangliosides, glycosphingolipids, 1,2-dioleoyl-3-trimethylammonium-propane, 1,2-di-O-octadecenyl-3-trimethylammonium propane.

Additional membrane forming lipids suitable for use in providing NLPs are well known to persons of ordinary skill in the art and are cited in a variety of well-known sources, e.g., McCutcheon's Detergents and Emulsifiers and McCutcheon's Functional Materials, Allured Publishing Co., Ridgewood, N.J., both of which are incorporated herein by reference.

In some embodiments, FMDV-NLPs herein described can comprise scaffold proteins such as human derived apoE4, truncated versions of human derived apoE4 (e.g. apoE4, 22k), human derived apoE3, truncated versions of human derived apoE3 (e.g. apoE3, 22k), human derived apoE2, truncated versions of human derived apoE2 (e.g. apoE2, 22k), human derived apoA1, truncated versions of human derived apoA1 (e.g. Δ49ApoA1, MSP1, MSP1T2, MSP1E3D1), mouse derived apoE4, truncated versions of mouse derived apoE4 (e.g. apoE4, 22k), mouse derived apoE3, truncated versions of mouse derived apoE3 (e.g. apoE3, 22k), mouse derived apoE2, truncated versions of mouse derived apoE2 (e.g. apoE2, 22k), mouse derived apoA1, truncated versions of mouse derived apoA1 (e.g. Δ49ApoA1, MSP1, MSP1T2, MSP1E3D1), rat derived apoE4, truncated versions of rat derived apoE4 (e.g. apoE4, 22k), rat derived apoE3, truncated versions of rat derived apoE3 (e.g. apoE3, 22k), rat derived apoE2, truncated versions of rat derived apoE2 (e.g. apoE2, 22k), rat derived apoA1, truncated versions of rat derived apoA1 (e.g. Δ49ApoA1, MSP1, MSP1T2, MSP1E3D1), lipophorins (e.g. *B. mori, M. sexta*), synthetic cyclic peptides that mimic the function of apolipoproteins. Other apolipoproteins, as will be understood for a skilled person, can be used to form NLP, including but not limited to apoB and apoC.

In some embodiments, the scaffold proteins can contain amino acid additions, deletions, or substitutions. In other embodiments, the scaffold proteins can be derived from various species and more particularly derived from human, mouse, rat, guinea pig, rabbit, cow, horse, pig, dog, and non-human primates.

As would be understood by those skilled in the art, in general, NLPs form with a molar ratio of scaffold protein to lipid in the 1:150-1:300 range. NLP assembly can be assessed experimentally using methods described herein and other methods known to those skilled in the art to determine optimal NLP assembly conditions for NLPs described herein to form complexes with engineered FMDV described herein.

In several embodiments herein described, genetically engineered FMDV-NLPs show different size, compositions, and homogeneity. Composition of a NLP can be detected by various techniques known in the art, such as high performance liquid chromatography (HPLC), reverse phase high performance liquid chromatography (RP-HPLC), mass spectrometry, thin layer chromatography, NMR spectroscopy and additional techniques identifiable by a skilled person.

Size and compositions of the genetically engineered FMDV-NLPs herein described can be characterized by SEC (size exclusion chromatography) traces which are used to separate out molecules in solution by their size and in some cases their molecular weights as will be understood by a skilled person.

Any measuring technique available in the art can be used to determine properties of the NLPs herein described. For example, techniques such as dynamic light scattering, x-ray photoelectron microscopy, powder x-ray diffraction, scanning electron microscopy (SEM), transmission electron microscopy (TEM), and atomic force microscopy (AFM) can be used to determine average size and dispersity of the NLPs.

In embodiments, genetically herein described engineered FMDV-NLPs herein described further include functionalized amphipathic compounds that can be added during the assembly of the NLP herein described.

The term "functionalized amphipathic compounds" in the sense of the disclosure indicates compounds having a hydrophobic portion and a hydrophilic portion in a configuration where the hydrophobic portion anchor is able to anchor the compound to the lipid bilayer of the NLP and the hydrophilic portion is presented on the NLP bilayer face following NLP assembly. In the functionalized amphipathic compounds in the sense of the disclosure the hydrophilic portion of typically essentially consists or comprises a hydrophilic functional group.

The term "functional group" as used herein indicates specific groups of atoms within a molecular structure that are responsible for a characteristic chemical reaction of that structure. Exemplary functional groups include hydrocarbons, groups containing double or triple bonds, groups containing halogen, groups containing oxygen, groups containing nitrogen and groups containing phosphorus and sulfur all identifiable by a skilled person.

The term "present" as used herein with reference to a compound or functional group indicates attachment performed to maintain the chemical reactivity of the compound or functional group as attached. Accordingly, a functional group presented on an amphipathic compound, is able to perform under the appropriate conditions the one or more chemical reactions that chemically characterize the functional group.

In NLPs, the use of functionalized amphipathic compounds enables attachment of various peptides or other biologics to the surfaces of the lipid of the NLP that allows some desired target features to be obtained, such as stability, affinity for a target molecule, and the like as will be understood by a skilled person (see U.S. Pat. Nos. 8,889,623 and 8,883,729 each incorporated herein by reference in its entirety).

The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material.

In the FMDV functionalized nanolipoprotein particle herein described, the NLP comprises a scaffold protein and a functionalized membrane forming lipid presenting a functional group that can attach one or more protein tags presented in the genetically engineered VP1 protein and in the genetically engineered FMD virus herein described (herein also protein tag substrate).

Non-limiting examples of functional groups presented on functionalized lipids include: chelated Ni atoms, azide, anhydride, alkynes, thiols, halogens, carboxy, amino, hydroxyl, and phosphate groups, and additional groups identifiable by a skilled person upon reading of the present disclosure.

In some embodiments, the functional group on the functionalized amphipathic compound can be a reactive chemical groups (e.g. azide, chelated nickel, alkyne, and additional reactive chemical group identifiable by a skilled person), a biologically active compound (e.g. DNA, peptide, carbohydrate, and additional biologically active group identifiable by a skilled person) or a small molecule (e.g. cellular targeting compound, adjuvant, drug, and additional small molecules identifiable by a skilled person). In some embodiments, the functionalized amphipathic compound is a functionalized lipid compound. Functional groups that enhance the lipid solubility are referred to as hydrophobic or lipophilic functional groups. Functional groups that lack the ability to either ionize or form hydrogen bonds tend to impart a measure of lipid solubility to a drug molecule. The functional group can be attached to the lipid polar head through covalent or ionic bonds and "weak bonds" such as dipole-dipole interactions, the London dispersion force and hydrogen bonding, preferably covalent. Moreover, functionalization of the lipid can involve hydrophobic quantum dots embedded into the lipid bilayer. The following article is incorporated by reference in its entirety: R. A. Sperling, and W. J. Parak. "Surface modification, functionalization and bioconjugation of colloidal inorganic nanoparticles". Phil. Trans. R. Soc. A 28 Mar. 2010 vol. 368 no. 1915 1333-1383.

In some embodiments, functionalized amphipathic compounds can comprise one or more of 1,2-dipalmitoyl-sn-glycero-3-phosphoethanolamine-N-(6-((folate)amino) hexanoyl), 1,2-dipalmitoyl-sn-glycero-3-phosphoethanolamine-N-(6-azidohexanoyl), 1,2-dipalmitoyl-sn-glycero-3-phosphoethanolamine-N-(succinyl), 1,2-dioleoyl-sn-glycero-3-phosphoethanolamine-N-(succinyl), 1,2-dipalmitoyl-sn-glycero-3-phosphoethanolamine-N-(glutaryl), 1,2-dioleoyl-sn-glycero-3-phosphoethanolamine-N-(glutaryl), 1,2-dioleoyl-sn-glycero-3-phosphoethanolamine-N-(dodecanyl), 1,2-Dipalmitoyl-sn-Glycero-3-Phosphoethanolamine-N-(hexanoylamine), 1,2-dipalmitoyl-sn-glycero-3-phosphoethanolamine-N-(dodecanylamine), 1,2-Dipalmitoyl-sn-Glycero-3-Phosphothioethanol, 1,2-dioleoyl-sn-glycero-3-phosphoethanolamine-N-[4-(p-maleimidomethyl)cyclohexane-carboxamide], 1,2-dioleoyl-sn-glycero-3-phosphoethanolamine-N-[4-(p-maleimidophenyl) butyramide], 1,2-dioleoyl-sn-glycero-3-phosphoethanolamine-N-[3-(2-pyridyldithio)propionate], 1,2-dioleoyl-sn-glycero-3-phosphoethanolamine-N-(biotinyl), 1,2-Dioleoyl-sn-Glycero-3-Phospho(Ethylene Glycol), 1,2-dioleoyl-sn-glycero-3-phosphoethanolamine-N-lactosyl, 1,2-distearoyl-sn-glycero-3-phosphoethanolamine-N-[dibenzocyclooctyl(polyethylene glycol)-2000], 1,2-distearoyl-sn-glycero-3-phosphoethanolamine-N-[succinyl (polyethylene glycol)-2000], 1,2-distearoyl-sn-glycero-3-phosphoethanolamine-N-[carboxy(polyethylene glycol)-2000], 1,2-distearoyl-sn-glycero-3-phosphoethanolamine-N-[maleimide(polyethylene glycol)-2000], 1,2-distearoyl-sn-glycero-3-phosphoethanolamine-N-[PDP(polyethylene glycol)-2000], 1,2-distearoyl-sn-glycero-3-phosphoethanolamine-N-[amino(polyethylene glycol)-2000], 1,2-distearoyl-sn-glycero-3-phosphoethanolamine-N-[biotinyl (polyethylene glycol)-2000], 1,2-distearoyl-sn-glycero-3-phosphoethanolamine-N-[cyanur(polyethylene glycol)-2000], 1,2-distearoyl-sn-glycero-3-phosphoethanolamine-N-[folate(polyethylene glycol)-2000], cholesterol modified oligonucleotides, cholesterol-PEG2000-azide, cholesterol-PEG2000-Dibenzocyclooctyl, cholesterol-PEG2000-maleimide, cholesterol-PEG2000-N-hydroxysuccinimide esters, cholesterol-PEG2000-thiol, cholesterol-azide, cholesterol-Dibenzocyclooctyl, cholesterol-maleimide, cholesterol-N-hydroxysuccinimide esters, cholesterol-thiol, C18 modified oligonucleotides, C18-PEG2000-azide, C18-PEG2000-Dibenzocyclooctyl, C18-PEG2000-maleimide, C18-PEG2000-N-hydroxysuccinimide esters, C18-PEG2000-thiol, C18-azide, C18-Dibenzocyclooctyl, C18-maleimide, C18-N-hydroxysuccinimide esters, C18-thiol.

In some embodiments, the functional group presented on the NLP is selected to bind and in particular to specifically bind one or more protein tags presented on one or more VP1 and/or one or more genetically engineered FMDV herein described.

The term "bind", "binding", "conjugation" as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure includes both non-covalent binding and, covalent binding. Non-covalent binding as used herein indicates a type of chemical bond, such as protein-protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities. An example of an electrostatic interaction includes using a charged lipid as the functional membrane lipid and binding an oppositely charged target molecule through electrostatic interactions Protein tag substrates and corresponding protein tag capable of binding through non-covalent binding include but are not limited to those listed in Table 1 below.

TABLE 1

| Non-Covalent Interactions | |
|---|---|
| Protein tag (or portion thereof) On FMDV | Protein tag substrate (on functionalized lipid within NLP bilayer) |
| Poly-histidine (2-10 residues) | Chelated metal cations |
| 2-10 residue polypeptide | $Ni^{2+}$, $Co^{2+}$, $Cu^{2+}$, $Zn^{2+}$ chelated on NTA, IDA |
| Poly-arginine (5-6 residues) | Negatively charged surface |
| 5-6 residue polypeptide | e.g. carboxylates, phosphates, sulfonates |
| SBP tag | Streptavidin |
| Strep-tag II | Streptactin |

A covalent bond is instead a form of chemical bonding that is characterized by the sharing of pairs of electrons between atoms, or between atoms and other covalent bonds. In short, attraction-to-repulsion stability that forms between atoms when they share electrons is known as covalent bonding. Covalent bonding includes many kinds of interaction, including σ-bonding, π-bonding, metal to non-metal bonding, agostic interactions, and three-center two-electron bonds.

Protein tag substrates and corresponding functional groups on protein tags capable of binding through covalent binding include but are not limited to those listed in Table 2 below.

TABLE 2

| Covalent Interactions | |
|---|---|
| Protein tag (or protein tag substrate) | Protein tag substrate (or Protein tag) |
| Amine-reactive moieties | Amines |
| Active esters (e.g. succinimidyl, tetrafluorophenyl) | |
| Carbodiimide (+/− NHS)-Carboxylic acids | |
| Isothiocyanates | |
| Sulfonyl chlorides | |
| Dichlorotriazines | |
| Aryl halides | |
| Acyl azides | |
| Thiol-reactive reagents | Sulfhydryls |
| Maleimides (and derivatives) | |
| Haloacetamides (e.g. iodoacetamide) | |
| Pyridyldithio-propionate | |
| Thiosulfates | |
| Azides | Acetylenes |
| ("Click Chemistry"-formation of 1,2,3-triazol groups, ref. 7) | |
| Hydrazines/ hydroxylamines/aromatic amines | Aldehydes and ketones |

In some embodiments, the tag substrate can be a molecule chelating a bivalent metal ion and the protein tag can be a polyhistidine molecule. In some of those embodiments, the bivalent metal ion can be selected from the group consisting of $Ni^{2+}$, $Zn^{2+-}$, $Co^{2+}$, and $Cu^{2}$.

In some embodiments, the tag substrate can be a negatively charged moiety and the protein tag is a poly-arginine molecule.

In some embodiments, the tag substrate can be avidin or a derivative thereof and the protein tag is selected from the group consisting of Avi-Tag, SBP-tag and Strep-tag In some embodiments, the tag substrate can be a thiol and the protein tag is selected from the group consisting of maleimide derivatives, haloacetamides, pyridyldithio-propionate and thiosulfates.

In some embodiments, the tag substrate can be selected from the group consisting of maleimide derivatives, haloacetamides, pyridyldithio-propionate and thiosulfates, and wherein the protein tag is a thiol presenting protein tag.

In some embodiments, the tag substrate can be an amine and the protein tag is selected from the group consisting of protein presenting active esters, activated carboxylic acids, isothiocyanates, sulfonyl chlorides, dichlorotriazines, aryl halides and acyl azides.

In some embodiments, the tag substrate can be selected from the group consisting of active esters, activated carboxylic acids, isothiocyanates, sulfonyl chlorides, dichlorotriazines, aryl halides and acyl azides, and wherein the protein tag is a protein presenting an amine group.

In some embodiments, the tag substrate can be an azide molecule and the protein tag is a protein presenting an acetylene group.

In some embodiments, the tag substrate can be an acetylene molecule and the protein tag is a protein presenting an azide molecule.

In some embodiments, the tag substrate can be is selected from the group consisting of hydrazines, hydroxylamines or aromatic amines and protein tag is a protein presenting an aldehyde or ketone group.

In some embodiments, the tag substrate can be an aldehyde or ketone molecule and the protein tag is selected from the group consisting of proteins presenting hydrazines, hydroxylamines and aromatic amines.

In some embodiments, the functional group presented on the NLP is selected to specifically bind one or more protein tags presented on one or more genetically engineered VP1 and/or one or more genetically engineered FMDV herein described.

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred.

In some embodiments one or more functionalized amphipathic compounds are comprised together with non-functionalized membrane forming lipids in the lipid component of the NLP. In some embodiments functionalized amphipathic compounds can be functionalized membrane forming lipid. In some embodiments, one or more functionalized membrane forming lipids are added or replace the membrane forming lipids in the lipid component of the NLP herein described also comprising one or more cross-linking lipids. For example, cross-linking lipids comprise commercially available lipids (e.g., Avanti Lipids) that are known to those skilled in the art, as described in Bader et al. 1985 [36], such as diyne- or diacetylene-containing lipids.

In particular, the ratio between functionalized membrane forming lipid and membrane forming lipids is dependent on the identity of the functionalized membrane forming lipid, and it can be as low as 1% or even lower and as high as 100% as NLPs have been successfully formed with 100% functionalized membrane forming lipid such as DOGS-NTA-Ni (1,2-di-(9Z-octadecenoyl)-sn-glycero-3-[(N-(5-amino-1-carboxypentyl)iminodiacetic acid)succinyl] (nickel salt)). This suggests that NLPs can be formed with any percentage of functionalized membrane forming lipid (from 0 to 100%), depending on the specific functionalized membrane forming lipid used.

In some embodiments, the ratio of functionalized amphipathic compounds can vary from 0.1 mol % to 95 mol % (relative to polymerizable lipid) depending on the functionalized amphipathic compounds. Functionalized amphipathic compounds that are lipids themselves, such as DOGS-NTA-Ni (1,2-di-(9Z-octadecenoyl)-sn-glycero-3-[(N-(5-amino-1-carboxypentyl)iminodiacetic acid)succinyl] (nickel salt)) can be used at 95 mol %, with cross-linking lipid comprising at least 5 mol %. A preferred molar ratio of DOGS-NTA-Ni:polymerizable lipid:membrane forming lipid is 35:20:45. In contrast, functional amphipathic compounds that are less lipid like, such as cholesterol modified oligonucleotides, a lower mol % (0.1-10 mol %) is needed for successful NLP assembly.

In some embodiments, the nanolipoprotein particles herein described can further comprise other functional molecules embedded in the membrane lipid bilayer (e.g. interacting with the membrane lipid bilayer components through van der Waals forces), conjugated to a lipophilic anchor compound inserted into the membrane lipid bilayer (e.g. through hydrophobic-hydrophilic interactions) or conjugated through binding of a functional group with a corresponding functional group presented on functionalized membrane forming lipid of the membrane lipid bilayer. In some of those embodiments, the other functional molecules comprise small molecules and in particular cyclic or non-cyclic peptides and can be comprised in the NLP here described in an amount that varies from case to case, and that in general can range from 0.1-10 mol %. inorganic nanoparticles". Phil. Trans. R. Soc. A 28 Mar. 2010 vol. 368 no. 1915 1333-1383.

In some embodiments herein described, the ratio of functionalized NLP to engineered FMDV is from 1:1 to 60:1. In some embodiments, the ratio of functionalized NLP to engineered FMDV is from 12:1 to 60:1. Exemplary data shown in the Table of FIG. 7 Panel D is based on measurements of NLP and virus particles based on two-dimensional electron microscopy images. However, in the context of the full virus particle the ratios shown in Table of FIG. 7 Panel D represent higher ratios (in three dimensions). Thus, as persons skilled in the art would understand, the number of FMD virion bound to NLP is in the range of 1:1 to 60:1.

Methods and systems for production of FMDV functionalized nanolipoprotein particles are known to those skilled in the art. The membrane forming lipid and the protein components of the FMDV functionalized NLP are generally able to self-assemble in a biological (largely aqueous) environment according to the thermodynamics associated with water exclusion (increasing entropy) during hydrophobic association. For instance, exemplary FMDV functionalized nanolipoprotein particles disclosed herein can be made following the methods described in Blanchette et al. 2010 [37] and Blanchette et al. 2009 [38].

Alternatively, the amphipathic lipid and the protein components of the NLP can be provided and allowed to assembly in cell free expression systems known to those skilled in the art.

As used herein, the wording "cell free expression" refers to at least one compound or reagent that, when combined with a polynucleotide encoding a polypeptide of interest, allows in vitro translation of said polypeptide/protein of interest.

In some embodiments, one or more genetically modified FMD viruses herein described is attached to a substrate to provide an array.

The term "array" as described herein, alternatively known as a "lab-on-a-chip" or "microarray", is a device configured for high-throughput screening and detection of biological molecular interactions, typically comprising a solid phase wherein a first molecule is attached to a substrate, and a liquid phase wherein a biological sample material is applied under suitable time and conditions to allow binding of a second molecule in the liquid phase to the first molecule attached to the solid phase. The solid phase can be comprised, for example of a glass slide, with immobilized molecules "spotted" onto the surface, or can comprise multi-well plates made of glass, plastic, or other materials known to those skilled in the art, with molecules attached to the inside surface of the well. As would be understood by those skilled in the art, different types of arrays can be used to detect a wide range of biological molecular interactions, such as DNA microarrays, RNA arrays, protein microarrays, peptide microarrays, tissue microarrays, chemical compound microarrays, and antibody microarrays, among others. Other arrays can comprise multi-well plates such as those used for ELISA, as described herein.

In some embodiments described herein, the engineered tagged FMDV can attach to an array or a plate via tag-substrate binding, wherein the substrate is coated onto the surface of the solid phase of the array or plate. For example, the mutant FMDV $2A_{6H}$ and FMDV $P1_{6H}$ described herein can bind directly to Ni-coated plates, such as those used for ELISA as described in the Example 8. As would be understood by those skilled in the art, this eliminates the need for virus-capturing biological molecules to attach the FMDV to the solid phase, such as FMDV strain-specific monoclonal antibodies or integrin receptor molecules.

In some embodiments, the array can be used for detection of antibody against one or more strains of FMD virus for investigation, research and/or diagnostic purposes. For example, an array can be used for the differentiation of animals vaccinated with a tagged FMDV from FMDV-infected animals, as described in Example 8. In addition, the ability to introduce a polynucleotide comprising a tagged VP1 protein into different FMDV strains by cloning into unique restriction sites as described herein (see FIG. 1B) enables detection of antibodies against additional strains and serotypes of FMDV.

In some embodiments, a composition comprising one or more genetically modified FMD virus, one or more genetically modified VP1 and/or one or more FMD functionalized nanolipoprotein particles together with a suitable vehicle is provided. In some embodiments, the composition is a pharmaceutical composition comprising one or more genetically modified FMD virus, and/or one or more FMD functionalized nanolipoprotein particles together with a pharmaceutically acceptable vehicle.

The term "vehicle" as used herein indicates any of various media acting usually as solvents, carriers, binders or diluents of a one or more genetically modified FMD virus, and/or one or more FMD functionalized nanolipoprotein particles comprised in the composition as an active ingredient.

In some embodiments, one or more genetically modified FMD virus, and/or one or more FMD functionalized nanolipoprotein particles can be comprised in pharmaceutical compositions (e.g. a vaccine) together with an excipient or diluent. In particular, in some embodiments, pharmaceutical compositions are described which contain one or more genetically modified FMD virus, and/or one or more FMD functionalized nanolipoprotein particles, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the FMD functionalized nanolipoprotein particles. Suitable excipients also include any substance that can be used to bulk up formulations with NLP to allow for convenient and accurate dosage. In addition to their use in the single-dosage quantity, excipients can be used in the manufacturing process to aid in the handling of NLP. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents comprise any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration. In some embodiments, compositions and, in particular, pharmaceutical compositions can be formulated for non-parenteral administration and more particularly intranasal, intratracheal, vaginal, oral, and sublingual administration.

Exemplary compositions for parenteral administration include but are not limited to sterile aqueous solutions, injectable solutions or suspensions including FMD functionalized nanolipoprotein particles. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

In some embodiments, compositions herein described comprise His-tagged FMDV capsid expressed as virus-like particle (VLP) for FMD vaccine developments produced in various biological systems such as *E. coli*, insect cells infected with recombinant baculoviruses or in mammalian cells with adenovirus vectors, or employing less virulent marker FMDV (FMDVLL3B3D) vaccine platforms with DIVA capabilities (allowing differentiation of infected from vaccinated animals) [35, 39, 40].

In one embodiment, a vaccine is provided, the vaccine comprising one or more genetically modified FMD virus, one or more nanolipoprotein particle comprising a scaffold protein and a functionalized membrane forming lipid presenting a protein tag substrate and/or one or more functionalized FMDV nanolipoprotein particles herein described together with a pharmaceutically acceptable vehicle.

The term "vaccine" as used herein indicates a composition, and in particular a biological preparation, that establishes or improves immunity to a particular external pathogenic assault in an animal. Vaccines in the sense of the present description can be prophylactic, or therapeutic. In vaccine herein described a modified FMDV alone or presented on an FMDV NLPS can be used as an antigen to immunize a mammal against FMD.

The term "antigen" or "immunogen" as used herein indicates a substance that prompts the generation of antibodies and/or can cause an immune response. In particular, antigens in the sense of the present disclosure encompass all substances that can be recognized by an adaptive immune system. Exemplary antigens include exogenous antigens and endogenous antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells ($CD4^+$) by the use of class II histocompatibility molecules on their surface. Some T cells are specific for the peptide: MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic $CD8^+$ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. Antigens are also generated between normal cells.

Vaccines of the present disclosure can further comprise one or more additional immunomodulatory components such as, e.g., an adjuvant or cytokine, among others. Non-limiting examples of adjuvants that can be used in the vaccine of the present disclosure include MPLA, Montanide ISA206, the RIBI adjuvant system (Ribi Inc., Hamilton, Mont.), polyICLC (Oncovir Inc, DC), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the disclosure include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween® 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

In particular embodiments, rationally designed FMDV vaccines are provided displaying 6×-His tags or other protein tags that interact with cations such as $Ni^{2+}$, $Co^{2+}$, nanolipoprotein particles (NLP) presenting chelated nickel (NiNLP) and NiNLPs preferably further containing adjuvant molecules.

Examples of other ions capable of binding to histidine tags comprise Cu, Zn, Ca, Mg, Fe, Ga, Sc, Y, In, and Tc. In particular, binding of metal ions to the surface of the His-tagged FMDV capsid can facilitate detection by in vivo tomographic imaging or other detection methods known to those skilled in the art. Metal ions can comprise diagnostic radioisotopes of ions such as Y, In, Tc, Cu, or Ga.

In some embodiments, a mutant FMDV vaccine is provided, when used in a chemically-inactivated form is capable of protecting an animal from clinical FMD when challenged with virulent FMDV wherein said vaccine comprises FMDV modified to display 6×-His tags on surface-exposed regions of the FMD viral capsid, wherein the latter are capable of interacting with adjuvanted NiNLP nanolipoprotein particles.

The term "chemically-inactivated" as used herein refers to an inactivated vaccine comprising of a genetically modified FMDV that has been chemically treated to 'kill' the virion so that it cannot divide, but the virus capsid proteins maintain some of their integrity to be recognized by the immune system and evoke an adaptive immune response.

Chemicals that can be used to inactivate virions comprise paraformaldehyde (PFA), binary ethylenimine (BEI), and others known to persons skilled in the art. Other methods to inactivate virions comprising vaccines comprise treating with heat, radiation, and others identifiable by a skilled person.

In particular, in some embodiments, genetically modified FMDV-NLP herein described present MPLA alone or in combination with additional adjuvants. MLPA is a well-established adjuvant that has been shown to induce both cellular and humoral immune responses. MPLA is a low toxicity derivative of a bacterial cell wall component, lipopolysaccharide (LPS).

In any of the above embodiments, one or more additional same or different adjuvant and/or antigen can be attached to the genetically modified FMDV-NLP through binding the anchor compound-anchor substrate compound and/or through incorporation of an amphipathic adjuvant into the nanoparticle during self-assembly.

In some embodiments, binding or conjugation of the adjuvant or other immunological agent can be performed by chelation of the immunological agent to a functional group presented by one or more functionalized lipids in the genetically modified FMDV-NLP herein described. The term "chelation" as used herein indicates the binding or complexation of a bi- or multidentate ligand with a single metal ion. In particular, in some embodiments, the bi- or multidentate ligand is part of the lipid and is capable of binding a metal ion. The ligands, which are often organic compounds, are called chelants, chelators, chelating agents, or sequestering agents. Chelating agents form multiple bonds with a single metal ion. The term "chelants" as used herein indicates a molecule that forms a stable complex with certain metal ions. Examples of chelating moieties include, but are not limited to, nitrilotriaceticacid (NTA), iminodiacetic acid (IDA), and diethylenetriamine penta-acetic acid (DTPA).

In some embodiments, an adjuvanted NiNLP nanoconstruct can be provided in combination and/or directly attached to the FMDV virus particle via the 6×-His sequence (or other tag) that has been introduced/engineered into the viral particle coat proteins. The adjuvanted NiNLPs bind directly to the viral capsid structure, (see the exemplary construct shown in FIG. 7 Panel B, center and right images where the tag is a 6xHIS). The presence of exposed 6×-His sequences on the surface of the mutant $A_{24}$FMDV $2A_{6H}$, or $A_{24}$FMDV $P1_{6H}$ FMD viruses enables the conjugation of adjuvanted NiNLP (MPLA-NiNLP) nanoconstructs to the surface of the viral capsid and the related combination has improved survival by 2-5 times in animal testing.

Successful binding of an immunological agent to the NLP can be readily verified and quantified through a range of techniques that include but are not limited to centrifugal filtration, size exclusion chromatography, fluorescence correlation spectroscopy, cantilever-based sensing, force spectroscopy, Fourier transform infrared spectroscopy, surface plasmon resonance, total internal reflection fluorescence, Raman spectroscopy and additional techniques identifiable by a skilled person. In addition, binding specifically to the surface can be verified using atomic force microscopy and transmission electron microscopy and additional techniques identifiable by a skilled person.

In some embodiments, the formation of genetically modified FMDV-NLP herein described is amenable to the incorporation of multiple adjuvants, including compounds directed to enhance immune response e.g. non-human lipoproteins, bacterial peptides, DNA (e.g. CpG motifs), chemokines, cytokines, pattern-recognition receptors (PRR), lipids, polysaccharides, lipopolysaccharides, and the like; in general, agonists and immune stimulatory molecules, synthetic or natural, (known or unknown at this time) can be assembled in or on NLPs, providing for enhanced, specific, rapid immune stimulation at the site of NLP/antigen inoculation and spreading systemically.

The genetically modified FMDV-NLP or the vaccines or compositions herein described can also be administered to an animal alone or in combination with additional immunostimulatory agents to immunize the animal.

In particular, in some embodiments, genetically modified FMDV-NLPs herein described can be used in combination with NLPs comprising an adjuvant such as microbial derivatives (e.g. CpG derivatives, MPLA), muramyl dipeptide derivatives (e.g. muroctasin), and any peptide or protein adjuvants (e.g. flagellin) can be incorporated into NLP directly to create an adjuvant NLP that can be used as an adjuvant or as a platform for subunit vaccine development with enhanced potency.

In particular, an adjuvant NLP according to the present disclosure can comprise single or multiple adjuvants, such as CpGs, MPLA, and cytokines. In some embodiments, an adjuvant NLP can be customized by including selected adjuvants in view of the desired effect based on the ability of different adjuvants to target different toll-like receptors (TLR) for immunostimulation (e.g. MPLA targets TLR 4, CpGs target TLR9, and flagellin targets TLR5). In some of these embodiments, the customization is performed in view of a specific vaccine formulation to be used in combination with the adjuvant NLP. The customization can be made to combine in the NLP only the adjuvants that are effective for the vaccine formulation of choice, since in some vaccine formulations only certain adjuvants are successful at enhancing the efficacy of the vaccine.

Immunization can be effected by simple injection, for example intramuscular injection in either the shoulder area or in the gluteus maximus hind muscular region. Genetically modified FMDV vaccines can be delivered following solubilization in sterile normal saline solution, for example.

In some embodiments, the genetically modified FMDV-NLP is significantly more immunogenic than the antigen alone, and can be used as a vaccine to protect against FMDV infection when injected into an animal, with or without the aid or use of an adjuvant.

The term "immune response" for purposes of this disclosure means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present disclosure, mean an immune response that is directed against one or more antigenic epitopes of a pathogen so as to protect against infection by the pathogen in a vaccinated animal. For purposes of the present disclosure, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, such as polypeptide sequences, optionally comprising non-protein groups such as carbohydrate moieties and/or lipid moieties.

The genetically modified FMD viruses encoded by the above-described isolated polynucleotide molecules are, in one embodiment, able to elicit an effective immunoprotective response against infection by a FMDV. Such genetically modified FMD viruses are preferably able to elicit an effective immunoprotective response against any strain of FMD viruses.

Determining suitable locations for a mutation or mutations that will encode a FMDV that remains able to elicit an effective immunoprotective response against infection by a FMDV and which can differentiate a naturally infected animal from a vaccinated animal can be made based on SEQ ID NO:1 and/or SEQ ID NO:3 provided herein. One of ordinary skill can refer to the sequence of the infectious cDNA clone of FMDV provided by this disclosure, make sequence changes which will result in a mutation inserting residues comprising protein tags displayed on the surface of the FMDV capsid and test the viruses encoded thereby for their abilities to produce FMD in cattle and swine, to elicit an effective immunoprotective response against infection by a FMDV, and to make possible the differentiation of infected vs. vaccinated animals. In so doing, one of ordinary skill can refer to techniques known in the art and also those described and/or exemplified herein.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present disclosure can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

Vaccines of the present disclosure can be formulated following accepted convention to include acceptable carriers for animals, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., *Remington's Pharmaceutical Science,* 18th ed., 1990, Mack Publishing, which is incorporated herein by reference.

Vaccines of the present disclosure can optionally be formulated for sustained release of the FMDV-NLPs, and/or a combination of engineered FMDV and NLPs herein described. Examples of such sustained release formulations include FMDV-NLPs, and/or a combination of engineered FMDV and NLPs in combination with composites of biocompatible polymers, such as, e.g., poly(lactic acid), poly (lactic-co-glycolic acid), methylcellulose, hyaluronic acid, collagen and the like. The structure, selection and use of degradable polymers in drug delivery vehicles have been reviewed in several publications, including Domb et al. 1992 [41], which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences*, Vol. 45, M. Dekker, NY, [42] which is also incorporated herein by reference. Alternatively, or additionally, the FMDV-NLPs, and/or a combination of engineered FMDV and NLPs can be microencapsulated to improve administration and efficacy. Methods for microencapsulating antigens are well-known in the art.

Liposomes can also be used to provide for the sustained release of FMDV-NLPs, and/or a combination of engineered FMDV and NLPs herein described. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

In one embodiment, a method of purification of genetically modified FMDV is provided, wherein the modification enables affinity purification of the genetically modified FMDV via binding on the 6×-His tag to divalent cations on columns, beads, and plates.

Polyhistidine-tags are often used for affinity purification of genetically modified proteins. Polyhistidine-tags can be used for affinity purification of polyhistidine-tagged recombinant proteins expressed in suitable host cells. For example, cells can be harvested via centrifugation and the resulting cell pellet lysed either by physical means or by means of detergents and enzymes such as lysozyme or any combination of these. At this stage, raw lysate contains the recombinant protein among many other proteins originating from the host cell. This mixture is incubated with an affinity resin containing bound bivalent nickel or cobalt ions, which are available commercially in different varieties. Nickel and cobalt have similar properties and as they are adjacent period 4 transition metals. These resins are generally sepharose/agarose functionalized with a chelator, such as iminodiacetic acid (Ni-IDA) and nitrilotriacetic acid (Ni-NTA) for nickel and carboxylmethylaspartate (Co-CMA) for cobalt, which the polyhistidine-tag binds with micromolar affinity. The resin is then washed with phosphate buffer to remove proteins that do not specifically interact with the cobalt or nickel ion. With Ni-based methods, washing efficiency can be improved by the addition of 20 mM imidazole (proteins are usually eluted with 150-300 mM imidazole). Generally, nickel-based resins have higher binding capacity, while cobalt-based resins offer the highest purity. The purity and amount of protein can be assessed by SDS-PAGE and Western blotting, among others known to those skilled in the art. Various purification kits for histidine-tagged proteins are available from commercial vendors such as Qiagen, Sigma, Thermo Scientific, GE Healthcare, Macherey-Nagel, Clontech, Bio-Rad, and others.

In one embodiment, a method of detecting genetically modified FMDV is provided, wherein the modification enables recognition of 6×-His tags by antibodies that specifically recognize the 6×-His sequence. For example, the polyhistidine-tag can be used to detect the protein via anti-polyhistidine-tag antibodies or alternatively by in-gel staining (SDS-PAGE) with fluorescent probes bearing metal ions. This can be useful in subcellular localization, ELISA, western blotting or other immuno-analytical methods known to those skilled in the art. The polyhistidine-tag can also be successfully used for the immobilization of proteins on a surface such as on a nickel- or cobalt-coated microtiter plate or on a protein array.

In one embodiment, a marker vaccine is provided, which allows a serological distinction between vaccinated animals and animals infected with FMDV.

A marker vaccine allows for immunological differentiation (or segregation) of infected from vaccinated animals, and is also referred to as a DIVA (or SIVA) vaccine [Differentiation (or Segregation) of infected from vaccinated animals] in veterinary medicine. In practical terms, this is most often achieved by omitting an immunogenic antigen present in the pathogen being vaccinated against, thus creating a negative marker of vaccination. In contrast, vaccination with traditional vaccines containing the complete pathogen, either attenuated or inactivated, precludes the use of serology (e.g. analysis of specific antibodies in body fluids) in epidemiological surveys in vaccinated populations. Apart from the advantage of allowing continued serological monitoring of vaccinated individuals, cohorts or populations; the serological difference between vaccinated individuals and individuals that were exposed to the pathogen, and were contagious, can be used to continuously monitor the efficacy and safety of the vaccine.

An exemplary marker vaccine provided herein comprises a 6×His tagged FMDV, which elicits an immune response specific to the tag, enabling the detection of vaccinated animal, for example by ELISA, and also detection of the vaccine virus. Exemplary methods for serological detection of an animal vaccinated with a marker vaccine are disclosed herein. For example, a serum sample can be obtained from an animal, which can then be applied to an indirect sandwich ELISA performed with modifications to the protocol specified by World Health Organization for Animal Health (2012) Chapter 2.1.5 Foot and mouth disease. In: Manual of diagnostic tests and vaccines for terrestrial animals 2012. OLE, Paris, France, which is herein incorporated in its entirety.

In some embodiments, genetically modified FMD viruses and related nanolipoprotein and compositions, and in particular vaccine compositions, can be used in a method to treat or prevent FMD in a cloven-hoofed animal. The method comprises administering to the cloven-hoofed animal an effective amount of a pharmaceutical composition and/or vaccine herein described by direct intramuscular, subcutaneous, intradermal and transdermal routes using needle injection or needle-free devices or automated devices such as gene guns, patches or any available vaccine delivery system.

In a particular embodiment, a method is provided for delaying onset or severity of FMD in an animal by administering an effective amount of chemically-inactivated genetically engineered marker FMDV vaccine formulation. In one embodiment, a method for protecting an animal against FMD by administering an effective amount of chemically-inactivated genetically engineered marker FMDV vaccine is provided.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above, such as seroconversion data.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies. For example, a titer of 1.5 log of serum neutralizing antibodies measured against a homologous vaccine strain or related heterologous strains can be indicative of protection.

The effective dose amount of virus, infectious RNA molecule, plasmid, or viral vector, of the present disclosure can be determined using known techniques, taking into account factors that can be determined by one of ordinary skill in the art such as the weight of the animal to be vaccinated. The dose amount of virus of the present disclosure in a vaccine of the present disclosure preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present disclosure in a vaccine of the present disclosure preferably ranges from about 0.1 g to about 100 mg, more preferably from about 1 μg to about 10 mg, even more preferably from about 10 μg to about 1 mg. The dose amount of an infectious RNA molecule of the present disclosure in a vaccine of the present disclosure preferably ranges from about 0.1 μg to about 100 mg, more preferably from about 1 μg to about 10 mg, even more preferably from about 10 μg to about 1 mg. The dose amount of a viral vector of the present disclosure in a vaccine of the present disclosure preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

In certain embodiments, one or more tags, one or more FMD virus and/or reagents to genetically modify an FMD virus can also be comprised in a system to provide a genetically modified FMDV according to methods herein described. In some embodiments, one or more genetically modified FMD virus, scaffold proteins and/or membrane forming lipids can be comprised in a system to provide an FMDV-NLP according to methods herein described In some embodiments, genetically modified FMDV, genetically modified VP1 proteins, polynucleotide, FMDV-NLPs and related compositions, can also be comprised in a system to treat or prevent FMD in a cloven-hoofed animal according to methods herein described. In those embodiments, the system can also comprise the immunostimulatory particle herein described and an adjuvant, the immunostimulatory particle and the adjuvant to be administered to the animal to immunize the animal against FMDV.

The systems herein disclosed can be provided in the form of kits of parts. In kit of parts, the tags, the one or more FMD virus and/or reagents to genetically modify an FMD virus can be included in the kit as a protein alone or in the presence of lipids/detergents for transition into nano-particles. The FMDV and/or the scaffold protein can be included as a plasmid or PCR DNA product for transcription/translation. The indicator protein may be included as encoded RNA for translation. In kit of parts for the immunization of an individual the immunostimulatory FDMV-NLP can be comprised together with adjuvant and/or adjuvant NLPs and additional components identifiable by a skilled person.

In a kit of parts, a polynucleotide, amphipathic lipid, target protein and/or scaffold protein, FMDV-NLPs, adjuvants, adjuvant NLPs and additional reagents are comprised in the kit independently possibly included in a composition together with suitable vehicle carrier or auxiliary agents. For example, a polynucleotide can be included in one or more compositions alone and/or included in a suitable vector, and each polynucleotide—is in a composition together with a suitable vehicle carrier or auxiliary agent.

Additional components can include labeled polynucleotides, labeled antibodies, labels, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (e.g. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

Having now generally described this disclosure, the same will be better understood by reference to certain specific examples, which are included herein only to further illustrate the disclosure and are not intended to limit the scope of the disclosure as defined by the claims.

Two 6×-His-tagged mutant viruses exemplify the modified viral capsids. The particular placement of the 6×-His insertions enables new effective vaccine formulations, purification protocols through histidine binding of divalent cations and anti-histidine antibody recognition protocols. The design of these 6×-His-mutant viruses carrying unique restriction sites flanking the capsid coding regions allows for exchange of cassettes representing relevant capsid coding regions of other FMDV strains/serotypes/and subtypes of FMDV field isolates.

Example 1: Viruses and Cell Cultures

FMDV type $A_{24}$ Cruzeiro was derived from the infectious cDNA clone, $pA_{24}$Cru [denoted herein as $A_{24}$ FMDV WT [3]. Baby hamster kidney strain 21, clone 13, cell line (BHK-21) was maintained in Eagle basal medium (BME; Life Technologies, Gaithersburg, Md.) supplemented with 10% calf serum (HyClone, South Logan, Utah), 10% tryptose phosphate broth, and antibiotic/antimycotic. Cells were grown at 37° C. with 5% $CO_2$ in a humidified atmosphere.

Example 2: Derivation of $A_{24}$ FMDV $2A_{6H}$ and $A_{24}$ FMDV $P1_{6H}$ The structural model of FMDV $A_{24}$Cru capsid was generated by homology modeling using the crystal structure of FMDV O1 BFS serotype (PDB, 1FOD) (Logan et al., supra). The structure was visualized on Pymol Molecular Viewer and analyzed for surface exposed residues/stretches. The 6×-His tag was inserted in $pA_{24}$Cru parental cDNA clone by overlap extension PCR in combination with infusion HD cloning. Primer pairs P2289 and P2290, for $A_{24}$ FMDV $2A_{6H}$, and primer pairs P2350 and P2351 for $A_{24}$ FMDV $P1_{6H}$, were used to insert 6×-His tag in $A_{24}$ FMDV (FIG. 1A-B). The 6×-His-containing fragments were generated by overlap PCR fusion, created by mixing PCR-amplified fragments, and re-amplifying through the product of the fusion of these two fragments. This was accomplished by using the primer pairs P2345 and P2346 (Table 3). The generated plasmids $A_{24}$ FMDV $2A_{6H}$ and $A_{24}$ FMDV $P1_{6H}$ contain a T7 promoter sequence in front of a hammerhead ribozyme at the 5' terminus of the S fragment of the FMDV genome, terminate with a poly(A) tract of 15 residues, and possess a unique restriction site PflMI and NheI that can be used for cassette exchange of different FMDV serotype capsids for vaccine development. Full-length genomic clones were linearized with SwaI and were in vitro-transcribed using the T7 Megascript system (Ambion, Austin, Tex.). Transcript RNAs were transfected into BHK-21 cells by electroporation as previously described [34]. The transfected cells were seeded in six-well plates and incubated for 24 to 48 h at 37° C. The viruses were passaged up to four times in BHK-21 cells, and complete viral genomes were verified by sequence analysis. Virus stocks at passage 4 were stored at −70° C. Passage 4 virus stocks were used in animal experiments and for the production of inactivated vaccines. Virus titers were determined by plaque assays as described below.

cleavage site is indicated with ↓. For $A_{24}$ FMDV $P1_{6H}$, the primers P2350_6H insert jun repeat for and P2351_6H insert jun repeat rev were used in combination with P2345_For infusion SacII P2346_Rev infusion NheI (Table 3) keeping the rest of cloning condition unchanged. In this clone, the FMDV $3C^{pro}$ cleavage site is disrupted/inactivated and shown with an arrow. The successful cloning of the 6×-His tag inserts in FMDV $A_{24}$ Cruzeiro backbone was confirmed by sequencing of the resulting plasmid DNA. Following are the partial (nucleotide and amino acid) sequences of the 6×-His tag-containing plasmids spanning the insert region for the 6×-His tag.

The nucleotide sequence of the $A_{24}$FMDV $2A_{6H}$ mutant virus spans VP1 and mutated 2A and encodes 8 extra amino acids (total amino acid residues 26) (SEQ ID NO:12, FIG. 2A). The amino acid sequence of $A_{24}$FMDV $2A_{6H}$ mutant virus spans VP1 and mutated 2A carries 8 extra amino acids inserted into 2A for a total of 26 amino acid residues (SEQ ID NO:13; FIG. 2B). The nucleotide sequence of $A_{24}$ FMDV $P1_{6H}$ mutant virus spans VP1 to 2A (SEQ ID NO:14; FIG. 2C). The amino acid sequence (SEQ ID NO:15) of $A_{24}$ FMDV $P1_{6H}$ mutant virus spans VP1 to 2A (FIG. 2D).

Figure 3:
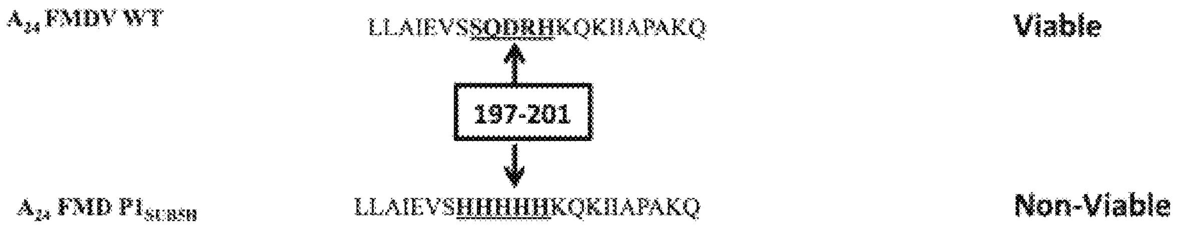
FIG. 3 depicts part of the amino acid sequence of an exemplary non-viable construct ($A_{24}$FMDV $P1_{SUB5H}$) where a 5×His tag was placed as a substitution rather than insertion. The substitution of 5 residues within FMDV C-terminus sequence LLAIEVSSQDRHKQKIIAPAKQ (SEQ ID NO:41) at amino acid 197-201 (position −15 to −8 from the C-terminus of FMDV VP1) for 5×His to give sequence LLAIEVSHHHHHKQKIIAPAKQ (SEQ ID NO:42) did not yield a viable virus after electroporation of mutant RNA and following five blind passages.

Thus, the mutant viruses $A_{24}$ FMDV $2A_{6H}$ and $A_{24}$ FMDV $P1_{6H}$ are derived by adding extra nucleotides encoding extra amino acids, (they are derived via insertions). Alternative locations were attempted to place a His-tag in the form of substitutions on the FMDV capsid and resulted in non-viable viruses. One example is presented in FIG. 3 where substitutions (rather than an insertion) were introduced on a surface region of the $A_{24}$ Cruzeiro FMDV capsid protein VP1 toward the C-terminus. In this His-tagged

TABLE 3

Description of PCR Primers used for generation of infectious cDNA clones for $A_{24}$ FMDV $2A_{6H}$ and $A_{24}$ FMDV $P1_{6H}$ viruses.

| Primer Name | Sequence | SEQ ID NO: |
|---|---|---|
| P2345_For infusion SacII | TCCCGTACGTATCCGCCGCGG | 5 |
| P2346_Rev infusion nhe | GACTCAACGTCTCCGGCTAGC | 6 |
| P2347_Rev infusion mfe | TGCCCTCAAAGAATTCAATTG | 7 |
| P2289_VP16H-KQ Forward primer | CACCACCACCACCACCACAAGCAGCTTCT GAATTTTGAC | 8 |
| P2290_VP16H-KQ Reverse primer | GTGGTGGTGGTGGTGGTGCTGCTTTGCTG GTGCAATGATC | 9 |
| P2350_6H insert jun repeat for | CACCACCACCACCACCACATCATTGCACC AGCAAAGCAGCTTCTGAATTTTGACCTG | 10 |
| P2351_6H insert jun repeat rev | GTGGTGGTGGTGGTGGTGCTTTGCTGGTG CAATGATC | 11 |

Full length infectious clone of FMDV $A_{24}$ Cruzeiro [3] was used as a template to PCR amplify various His-tagged FMDV VP1 or 2A fragments that were used for overlap extension PCR amplification of $A_{24}$ FMDV 6×-His-tag amplicons. For $A_{24}$ FMDV $2A_{6H}$, PCR primer P2289 VP16H-KQ Forward primer, P2290 VP16H-KQ Reverse primer, & P2345. For infusion, Sac II, P2346_Rev infusion Nhe I (Table 3) were used to generate the insert containing SacII and Nhe I infusion cloning sites. The parental FMDV $A_{24}$ Cruz clone digested with Sac II and Nhe I was used as a vector to clone the insert in the vector using infusion HD cloning kit (Clontech® Laboratories, Inc.) to create the mutant virus plasmid DNA containing 6H insert in the VP1 region at the VP1-2A junctions (FIG. 1A). The FMDV $3C^{pro}$ mutant full length cDNA clone construct, five amino acids near the C-terminus of VP1 were replaced by 5×His residues. Viral RNA transcribed from this mutant RNA produced non-viable virus progeny following electroporation. Moreover, following up to 8 blind passages after electroporation, this His-tagged substitution mutant RNA produced no signs of cytopathic effect (CPE). Thus, the data suggested that either the location of His tag or the replacement of viral residues by 5×His were deleterious for RNA infectivity at certain locations of the capsid.

A pair of unique restriction enzyme recognition sites were identified herein (FIG. 1B) that can be exploited for cassette exchange of the capsid coding region of other virus serotypes containing the 6×-His tag insert with FMDV $A_{24}$ 6×-His virus. The restriction sites used are indicated as R1 and R2 (FIG. 1B). R1 is a PflMI enzyme site that spans nucleotide 1547-1559 of FMDV genome in the $L^{pro}$ coding region. R2 is a Nhe I enzyme site that spans nucleotide 3911-3916 of FMDV genome in the 2A coding region. The two clones $A_{24}$ FMDV $P1_{6H}$ and $A_{24}$ FMDV $2A_{6H}$ are shown with the position of 6×-His indicated (FIG. 1B).

Figure 4A:
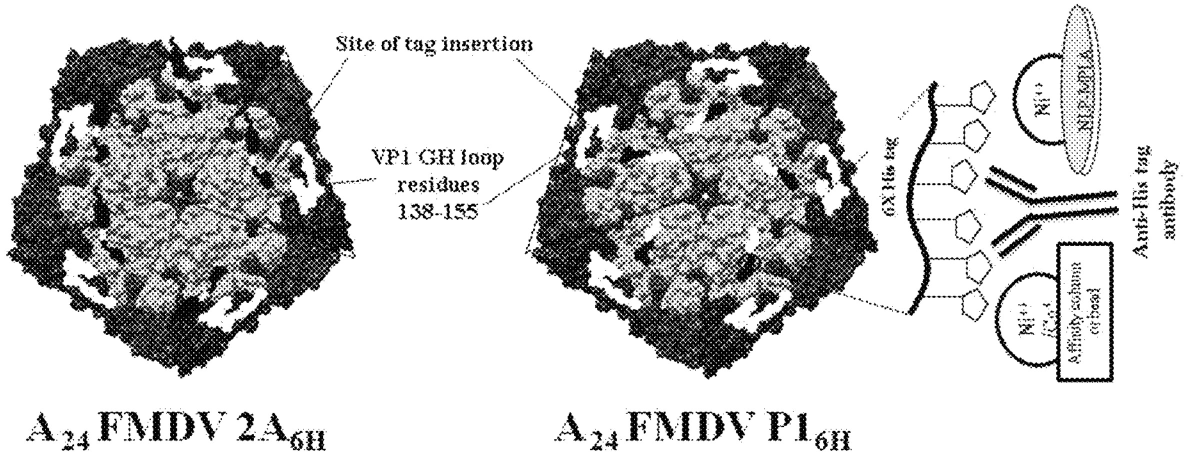
FIG. 4A depicts the pentameric structure of the FMDV $A_{24}$Cru capsid and shows the major immunodominant (GH) loop on the capsid and the positioning of the 6×-His insertion. The modeled structure of the pentameric unit of FMDV A24 was created by homology modeling of FMDV $A_{24}$ on FMDV type 0 virus structure (PDB: 1FOD). The resultant FMDV $A_{24}$ capsid pentamer is shown in surface representation with VP1 shown in light gray, VP2 shown in black and VP3 shown in dark gray (FIG. 4A). GH loop residues 138-155 are shown as white colored loops. Tags are positioned on the insertion site in $A_{24}$ FMDV $2A_{6H}$ and $A_{24}$ FMDV $P1_{6H}$. Monomeric unit of the capsid is marked by triangle. 6×His tag is zoomed in the inset and tag binding reagents $Ni^{++}$/$Co^{++}$ bead/affinity column; anti-his antibody and MPLA:NiNLP are shown. The anti-GH loop antibody binding site was deduced from FMDV type C complexed with monoclonal antibody (PDB: 1QGC).
Figure 4B:
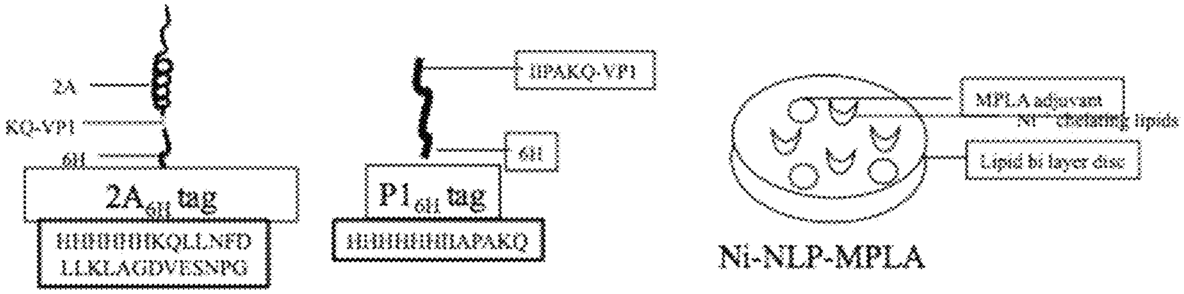
FIG. 4B shows a schematic diagram showing 6×His tags and MPLA:NiNLP. On the left there are two cartoon diagrams representing the secondary structure of the respective exemplary $2A_{6H}$ and $P1_{6H}$ tags. 6H and 2A peptide structures were drawn on the basis of by JPred software prediction. The orientation of individual peptides such as 6H, KQ residues of FMDV VP1, 2A or IIAPAKQ (SEQ ID NO:39) was deduced from crystal structure of FMDV type 0 virus structure (PDB: 1FOD). The sequence shown under the diagram of the $2A_{6H}$ tag is HHHHHHKQLLNFDLLKLAGDVESNPH (SEQ ID NO: 49), and the sequence shown under the diagram of the $P1_{6H}$ tag is HHHHHHIIIAPAKQ (SEQ ID NO:50). On the right panel, the NLP bilayer is represented as a disc with embedded MPLA and $Ni^{++}$ shown as circle or half circle, respectively.

In order to show the location of 6×-His tag on the surface of mutant FMD viruses a homology model of FMDV $A_{24}$Cru was constructed. Using this monomeric model, a pentameric model was constructed. As shown in FIG. 4, the site of 6×-His insertion is surface exposed and displayed as bright yellow spheres (indicated by residue number as well as antibody cartoon). The G-H loop is major immunodominant epitope on the surface of mutant FMDV. The virus utilizes the RGD tri-peptide motif in the G-H loop to bind specifically with the integrin receptors on the cellular surface. As evident from FIG. 4, the 6×-His insertion site is distant from the G-H loop; therefore, the 6×-His insertions designed herein is not obscure the integrin receptor affinity of the mutant virus.

Example 3: Rescue of Parental and Mutant Viruses, Viral Growth, and Plaque Assays; In Vitro Characterization of A24 FMDV 2A611 and A24 FMDV P1611

After sequence verification of the full genome cDNA construct shown above (FIG. 1), plasmid DNAs containing the genome length cDNA clones of $A_{24}$ FMDV $2A_{6H}$ and $A_{24}$ FMDV $P1_{6H}$ were linearized with SwaI enzyme and transcribed using the Megascript T7 kit (Ambion) following the manufacturer's instruction. The transcript RNAs were then evaluated for the recovery of virus progeny in BHK-21 cells following electroporation. About 10 μg RNA of each mutant virus was used to electroporate $2\times10^7$ BMK cells. The medium was changed 3 h post electroporation. The cells were incubated overnight at 37° C. and 5% $CO_2$ and were then frozen at −80° C. The flasks containing the frozen cells were thawed and the next passage was initiated using 1/10th vol. of this material as inoculum. Three passages were conducted for each virus and passage 3 was used to produce a large batch of virus to be used in future experiments.

The mutant viruses $A_{24}$ FMDV $2A_{6H}$ and $A_{24}$ FMDV $P1_{6H}$ produced a cytopathic effect (CPE) in the transfected cells. Sequence analysis confirmed that the mutant viruses maintained the 6×His-tags following 4-5 passages. Full genome sequence of the progeny virus indicated that no additional mutations were fixed in the virus following passages in tissue culture. Stocks of these viruses were titrated and their plaque morphologies were compared with the parental virus (FIG. 5).

For virus growth curves, BHK-21 monolayers were infected with $A_{24}$ FMDV WT, $A_{24}$ FMDV $2A_{6H}$ and $A_{24}$ FMDV $P1_{6H}$ at a multiplicity of infection (MOI) of 5 PFU/cell. After 1 h of adsorption at 37° C., the monolayers were rinsed once with MES buffer (morpholine ethanesulfonic acid [25 mM], 145 mM NaCl [pH 5.5]) followed by the addition of virus growth medium (BME, 1× anti-anti, 1%). At various times post infection, virus titers were determined by fifty percent tissue culture infectious dose $TCID_{50}$ assays. Plates were fixed and then stained with crystal violet (0.3% in Histochoice; Amresco, Solon, Ohio), and the plaques were counted. Titers were expressed as $TCID_{50}$/ml and determined in quadruplicates.

Figure 5A:
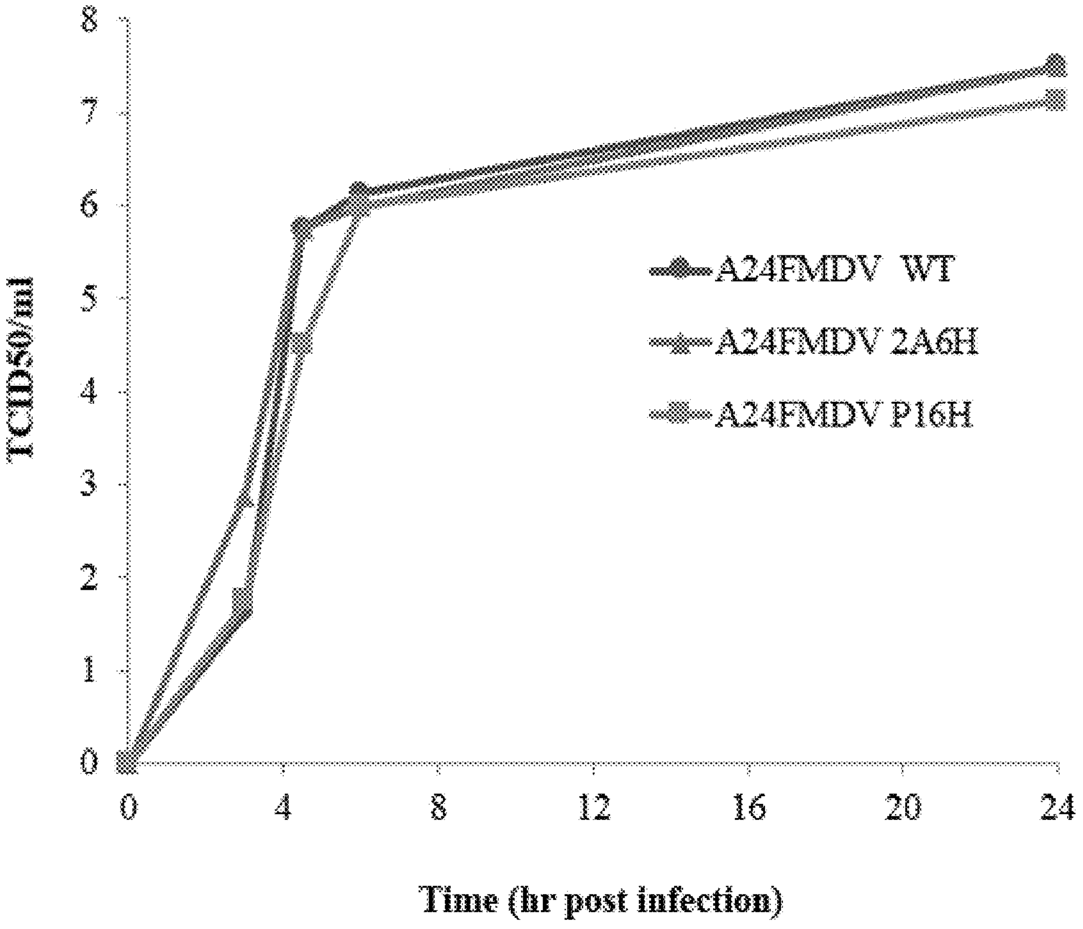
Figure 5B:
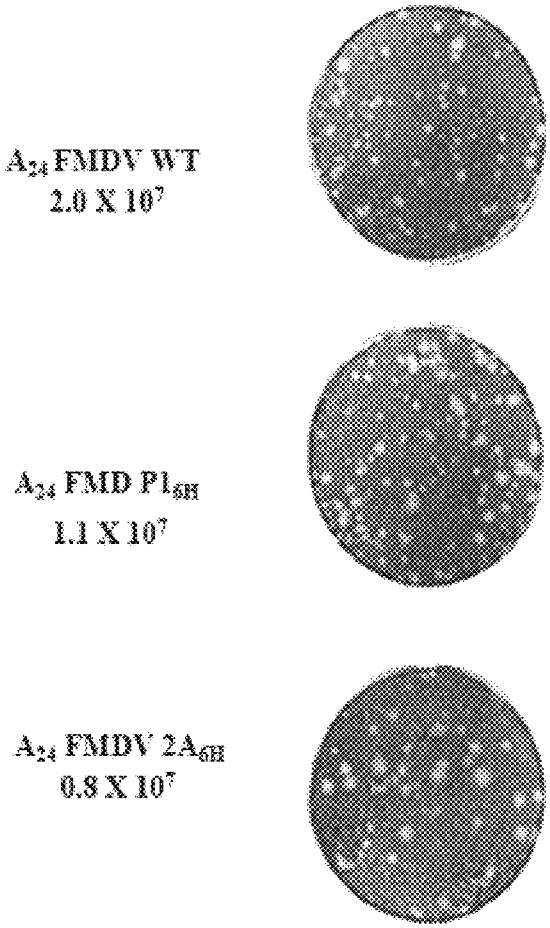

From the results shown in FIG. 5, it is evident that the mutant viruses grew to same kinetics and reach similar titers as the WT $A_{24}$Cru virus (FIG. 5A). Moreover, both $A_{24}$ FMDV $2A_{6H}$ and $A_{24}$ FMDV $P1_{6H}$ viruses produced plaques with similar morphology and size as the parental WT counterpart (FIG. 5B).

Next the antigenic properties were examined of parental and mutant viruses against hyperimmune sera generated in cattle infected with the parental $A_{24}$ virus. As shown in FIG. 5C, $A_{24}$ FMDV $2A_{6H}$ and $A_{24}$ FMDV $P1_{6H}$ viruses were neutralized very similarly as the WT $A_{24}$ FMDV. As evident from the r1 values, both mutant viruses $A_{24}$ FMDV $2A_{6H}$ and $A_{24}$ FMDV $P1_{6H}$ have r1 values above 0.3 (1.99 and 0.7 respectively), suggesting that they are antigenically related to WT FMDV $A_{24}$ Cruzeiro.

6×-His tag expression in the mutant 6×-His tagged FMDVs was detected by ELISA assay that utilized a pre-blocked nickel-coated plate (Ni-NTA HisSorb Strips, Qiagen, Catalog No. 35023) for determination of the specificity of binding of 6×-his tagged FMDV $A_{24}$ virus. The optimal concentrations of 6×-his tagged FMDV $A_{24}$ was determined for binding to the plate. For this purpose, a serial dilution of 6×-His tagged FMDV $A_{24}$ ($A_{24}$ FMDV $2A_{6H}$ and $A_{24}$ FMD $P1_{6H}$) in total of 200 uL of PBS were bound to pre-blocked nickel-coated wells of a 96 well plate overnight at 4° C. After incubation, the plate was washed three times with PBS and primary antibody (Anti-His tag pAb, Abnova, Catalog No. PAB0862) was added at a 1:500 dilution in 1% BSA in PBS for 90 minutes at 37° C. Post-antibody incubation, plates were washed with PBS three times. Secondary antibody (Goat anti-rabbit IgG h+1 HRP conjugated, Bethyl Laboratories, Catalog No. A120-101P) was added at a 1:2000 dilution in 1% BSA in PBS and incubated for one hour at 37° C. Plates were washed four times in PBS. Substrate (SureBlue Reserve TMB Microwell Peroxidase Substrate (1-Component), KPL, Catalog No. 53-00-00) was added in a volume of 100 uL and incubated at room temperature until color development was noted (approximately 10 minutes). Stop solution (TMB BlueSTOP solution, KPL, Catalog No. 50-85-31) was added to inhibit continued substrate reaction in a volume of 100 uL and plates were read at 630 nM with brief 5 second shaking via a colorimetric plate reader. On the basis of this experiment, FMDV $A_{24}$-6×-his amount corresponding to OD=1.0 at 630 nM was found to be optimal for coating FMDV $A_{24}$ 6×-his virus on Ni-NTA HisSorb Strips.

Figure 6A:
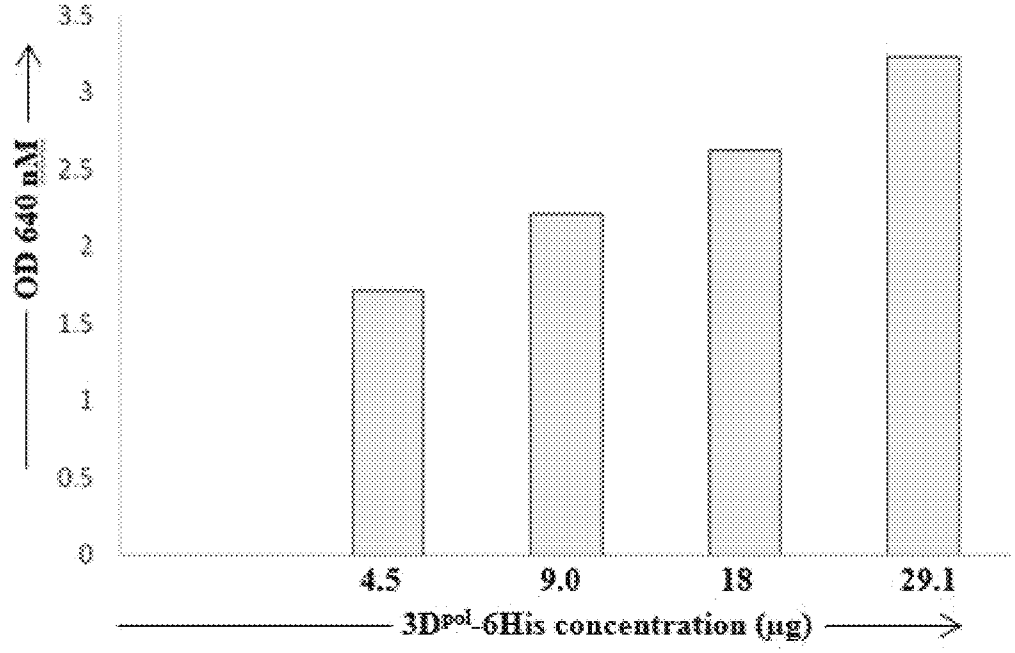
FIGS. 6A-6C depict the dose-dependent detection of the 6×-His-tag.

The specificity of the binding of His-tag proteins to the Ni-NTA plate was examined. For this purpose, FMDV $3D^{pol}$-6×His was bound to the Ni-NTA-coated pre-blocked plates (Qiagen). The binding of $3D^{pol}$-$_{6x}$His was detected with anti-His antibody (Novus Biologicals) at 1:500 dilution using TMB Sure kit [4]. As shown in FIG. 6A the $OD_{630}$ increased in a dose dependent manner with increasing concentration of $3D^{pol}$-6×His. The $3D^{pol}$-$_{6x}$His dose-dependent increase in $OD_{630}$ validates that the Ni-NTA plate and the reaction conditions used herein can specifically detect the presence of 6×-His tagged proteins.

Figure 6B:
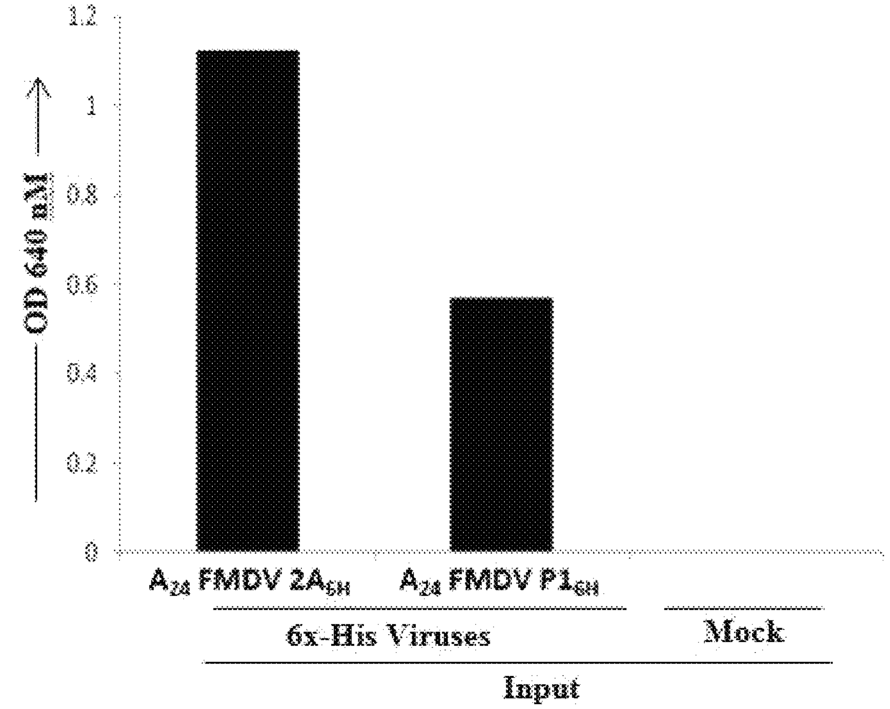

Next the lysates from mutant $A_{24}$ FMDV $2A_{6H}$- and $A_{24}$ FMDV $P1_{6H}$-infected cells were applied to Ni-NTA-coated pre-blocked plates (Qiagen) and the detection of 6×-His tag was performed under identical condition as described in FIG. 6A. As evident from the data in FIG. 6B showing high $OD_{630}$ in the range of 0.6-1.2, $A_{24}$ FMDV $2A_{6H}$ and $A_{24}$ FMDV $P1_{6x}$ bound efficiently to the Ni-NTA plate. The binding of mutant $A_{24}$ FMDV $2A_{6H}$ and $A_{24}$ FMDV $P1_{6H}$ viruses to the Ni-NTA plate confirmed the expression of functional 6×-His tag on surface-exposed capsid residues. In contrast, no binding of the mock-infected cell lysates was evident in the ELISA assay. The data from FIGS. 6A and 6B demonstrate a specific assay condition for detection of 6x-His tagged proteins and confirm the expression of the surface-exposed 6x-His tag in the two mutant viruses.

Figure 6C:
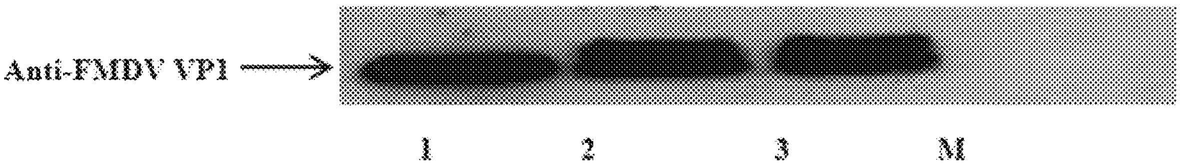

Next, the mutant viruses $A_{24}$ FMDV $2A_{6H}$ and $A_{24}$ FMDV $P1_{6H}$ were characterized for expression of intact VP1 capsid protein by western blot assay (FIG. 6C). BHK-21 cells were either mock infected or infected with $A_{24}$WT, $A_{24}$ FMDV $2A_{6H}$ or $A_{24}$ FMDV $P1_{6H}$ at a multiplicity of infection (MOI) of 0.01 PFU/cell. The following day, cells were lysed with radio-immunoprecipitation assay buffer (PBS supplemented with 1% NP-40, 0.5% sodium deoxycholate, 0.1% sodium dodecyl sulfate [SDS], and protease inhibitors). Equal protein (50 μg) of cell lysates from FMDV $A_{24}$ WT-(lane 1), $A_{24}$ FMDV $2A_{6H}$- (lane 2), $A_{24}$ FMDV $P1_{6H}$-(lane 3) (FIG. 6C) infected and mock-infected (M) were electrophoresed under denaturing conditions in a SDS-12% PAGE gel (Invitrogen) and transferred onto Hybond Nylon membrane using an XCell II transfer system (Invitrogen). The blots were blocked with 5% skim milk in PBS-Tween (PBS-T) for 1 h at room temperature, followed by an additional incubation of 1 h with rabbit polyclonal anti-VP1 (1:2,000). The two mutant viruses $A_{24}$ FMDV $2A_{6H}$ and $A_{24}$ FMDV $P1_{6H}$ shown in lane 2 and 3 respectively, expressed VP1 protein to similar concentrations as their WT counterpart (lane 1). As expected, there are no VP1-specific protein bands detected in mock-infected cell lysates.

Example 4: Determination of Complex Formation Between NiNLP-MPLA and Marker 6xHis-Tagged Mutant FMDVs Four distinctive methodologies were utilized to demonstrate the formation of a complex between mutant viruses and NiNLP-MPLA nanoconstructs, as following: (1) electron microscopic examination of virus alone or in complexes, (2) binding of 6x-His mutant FMDV $A_{24}$ $2A_{6H}$ to NiNLP-MPLA as determined by Agaraose Gel Electrophoresis (AGE), (3) binding of NiNLP to mutant $A_{24}$-FMDV$2A_{6H}$ as determined by competitive ELISA, and (4) binding of mutant FMDV $A_{24}$ 6x-His-tagged viruses to Co-NTA beads.

For electron microscopic (EM) analysis, $A_{24}$ FMDV WT or 6x-His-tagged mutant FMDVs ($A_{24}$ FMDV $2A_{6H}$ or $A_{24}$ FMDV $P1_{6H}$) chemically-inactivated with BEI were conjugated with NiNLP-MPLA in the presence of Tris-buffered-saline (TBS) pH=7.4 for 45 min at room temperature. Virus alone or complexes of NLP-MPLA mixed with Foot-and-Mouth Disease Viruses ($A_{24}$ FMDV WT, $A_{24}$ FMDV $2A_{6H}$ and $A_{24}$ FMDV $P1_{6H}$), NiNLP-MPLA alone, were adsorbed to 1% Alcian Blue-treated, formvar-carbon coated nickel grids (electron Microscopy Sciences (EMS), Hatfield, Pa.), stained with 2% uranyl acetate and imaged with a Hitachi T-7600 electron microscope operated at 80 KV. The dimensions of free NiNLP-MPLA and the diameters of FMDV particles and the FMDV-NiNLP-MPLA complexes were measured at 70,000x using Hitachi software that had been calibrated with a diffraction grating replica (EMS). The number of NiNLP-MPLA linked to FMDV particles was determined on micrographs at a magnification of 340,000x.

Figure 7:
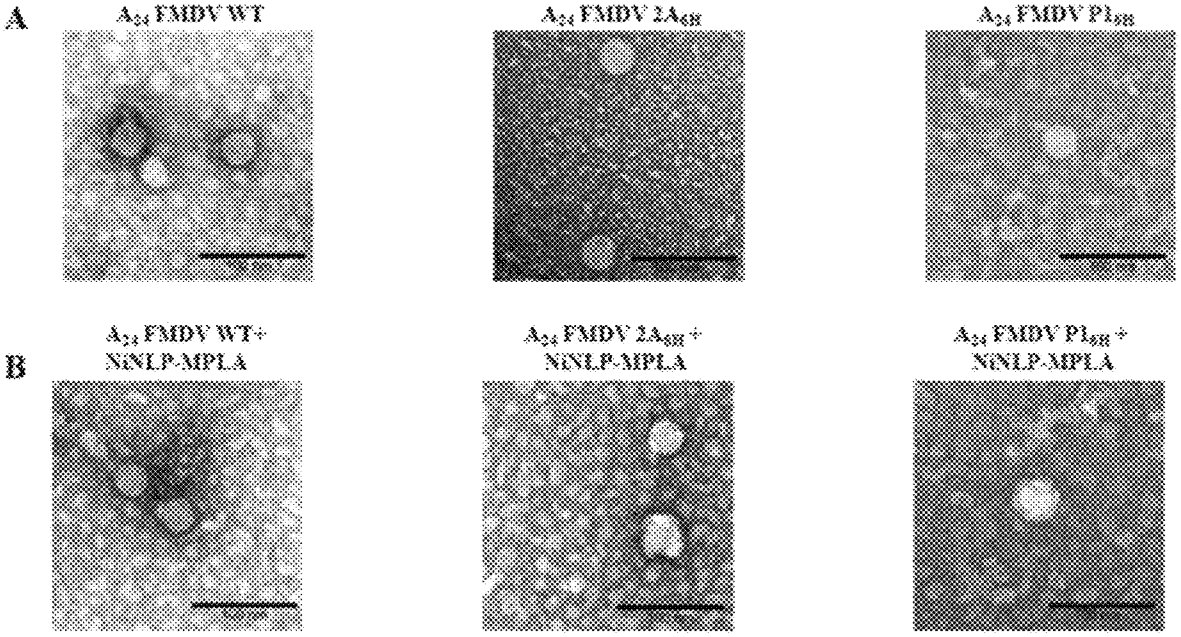
FIG. 7 shows results of electron microscopic detection of 6×-His mutant FMDV alone or bound to Nickel nanolipoprotein conjugated to adjuvant MPLA (NiNLP-MPLA). The three images in FIG. 7 Panel A show $A_{24}$ FMDV WT alone (left), $A_{24}$ FMDV $2A_{6H}$ alone (middle) and $A_{24}$ FMDV $P1_{6H}$ alone (right). The three images in FIG. 7 Panel B show $A_{24}$ FMDV WT mixed with MPLA:NiNLP (left), $A_{24}$ FMDV $2A_{6H}$ mixed with MPLA:NiNLP (middle) and $A_{24}$ FMDV $P1_{6H}$ mixed with MPLA:NiNLP (right).
Figure 7:
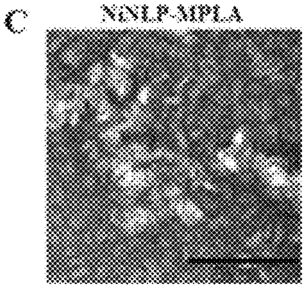

FIG. 7 Panels A-D depict electron microscopic detection of 6x-His mutant FMDV alone or bound to Nickel nanolipoprotein conjugated to adjuvant MPLA (NiNLP-MPLA). The three images in FIG. 7 Panel A show $A_{24}$ FMDV WT alone (left panel), $A_{24}$ FMDV $2A_{6H}$ alone (middle panel) and $A_{24}$ FMDV $P1_{6H}$ alone (right panel). The three panels in FIG. 7 Panel B show $A_{24}$ FMDV WT mixed with MPLA:NiNLP (left image), $A_{24}$ FMDV $2A_{6H}$ mixed with MPLA:NiNLP (middle panel) and $A_{24}$ FMDV $P1_{6H}$ mixed with MPLA:NiNLP (right panel). FIG. 7 Panel C shows MPLA:NiNLP alone. The Table in FIG. 7 Panel D shows the number of MPLA:NiNLP bound to $A_{24}$ FMDV $P1_{6H}$. detected in electron microscopy captured images.

As seen in FIG. 7 Panel B (middle and right images) representing the mixture of mutants $A_{24}$ FMDV $2A_{6H}$+NiNLP-MPLA or $A_{24}$ FMDV $P1_{6H}$+NiNLP-MPLA, the virus particles were coated with NiNLP-MPLA. In contrast, in FIG. 7 Panel B (left image) consisting of $A_{24}$ FMDV WT+NiNLP-MPLA mix, $A_{24}$ FMDV WT virus does not show any coating of the virus with NiNLP-MPLA. NiNLP-MPLA alone is shown in FIG. 7 Panel C at the same dimensions as those seen in FIG. 7 Panel B. This experiment demonstrated the presence of the virus bound to NiNLP-MPLA. Note that the virus capsid consists of 60 copies of VP1 arranged in an icosahedral shell structure; and therefore, at saturation levels, a maximum of 60 copies of NiNLP-MPLA per virus are expected to be present in FMDV-NiNLP-MPLA complexes.

Figure 8A:
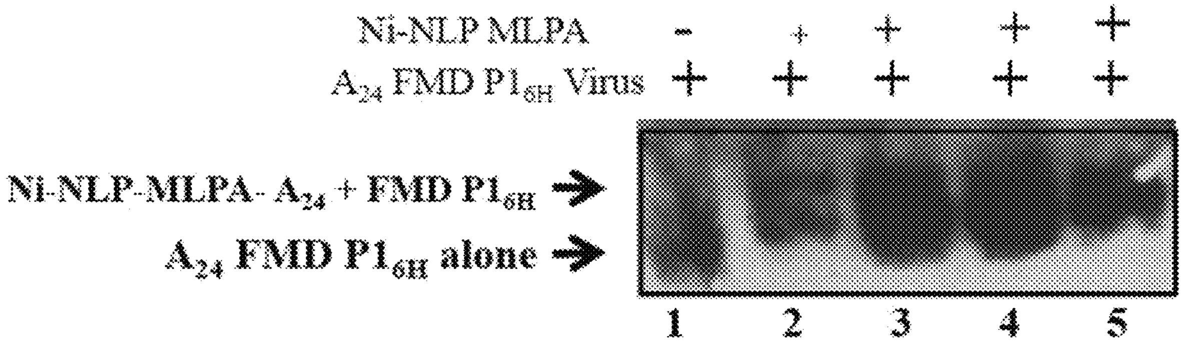
FIGS. 8A-8B depict the electrophoretic mobility shift assays of mutant 6×-His FMDV complexed with NiNLP-MPLA.
Figure 8B:
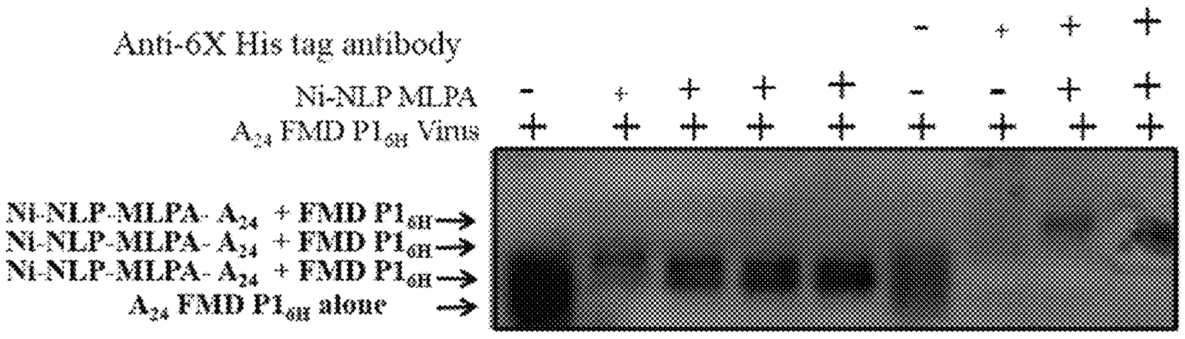

The binding of 6x-His mutant $A_{24}$ FMDV $P1_{6H}$ to NiNLP-MPLA was determined by agarose gel electrophoresis. Native gel electrophoresis is a method of choice in the biochemical determination of protein-protein interaction; however, it is quite challenging when full virus particles are involved. Both the electrophoretic migration and the protein-protein interactions are affected by a number of parameters, such as: pH, ionic strength and buffering agent. Optimizing an agarose gel electrophoresis protocol as well as a passive protein transfer protocol enabled us to study the effect of NiNLP-MPLA on the electrophoretic migration of FMDV particles that contained 6x-His tag in their VP1 capsid protein. The mutant $A_{24}$ FMDV $P1_{6H}$ virus (1.5 ug-5 ug) was either mixed with increasing concentrations of antibodies: anti-FMDV $A_{24}$ VP1 at 1:2000 dilution or anti-6xHis at 1:500 dilution or with mixed, increasing concentrations of NiNLP-MPLA. The binding of virus with NiNLP-MPLA or antibodies was carried out in the presence of phosphate buffered saline pH=7.4 at room temperature for 45 min. After incubation, the reactions were mixed with 10% glycerol and 0.025% Bromophenol blue and loaded on 1% agarose gel. The gel was pre-run at 60 V for 4 hr @ 4° C. before electrophoresis of NiNLP-MPLA+virus reactions. The electrophoresis was carried out at 60 V for 2 hrs. After electrophoresis, the passive transfer of protein was carried out overnight. The protein bands were developed with 1:2000 dilution of rabbit anti-FMDV VP1 followed by 1:10,000 Goat anti-rabbit-HRP. FIG. 8 shows the result of agarose gel electrophoretic analysis of the binding of mutant FMDV $A_{24}$ $P1_{6H}$ to NiNLP-MPLA and Anti-6xHis antibody (Abnova). In order to detect the effect of the NiNLP-MPLA reaction, mixtures containing mutant virus $A_{24}$ FMDV $P1_{6H}$ alone or complexes involving virus $A_{24}$ FMDV $P1_{6H}$+NiNLP-MPLA were electrophoresed for 4 h at 60V and detected by anti-VP1 (guinea pig polyclonal 1:2000) antibody. The results demonstrated the shift of intact FMDV particles bound to NiNLP-MPLA at ratios 1:1, 1:2.5, 1:5 and 1:7.5 (lanes 2, 3, 4 and 5) in comparison to virus alone (lane 1, FIG. 8A). In a separate experiment, purified mutant virus $A_{24}$ FMDV $P1_{6H}$ was mixed with increasing concentration of NiNLP-MPLA (1:1 to 1:7.5). As evident from FIG. 8B (lanes 2-5) at increasing ratios of virus to NiNLP (1:1 to 1:7.5) showed retarded electrophoretic mobility complexes being formed in comparison to virus alone (lane 1). Lane 7 consists of mutant 6xHis bound to NiNLP-MPLA after addition of an anti-6x-His antibody. A marked shift in the mobility of virus was observed that caused a retardation of electrophoretic mobility complex (lanes 8-9) that was distinct from virus alone (lane 1), virus+NiNLP-MPLA (lanes 2-5) and virus+anti-6×His antibody (lane 7). Lane 6 shows another mutant virus alone control, mutant $A_{24}$ FMDV $P1_{6H}$ alone. Together, data from FIG. 8 provides evidence for the binding of NiNLP-MPLA to $A_{24}$ FMDV $P1_{6H}$ and for the supershift when additional anti-6×-his antibody are added to the virus: NiNLP-MPLA complexes.

Figure 9A:
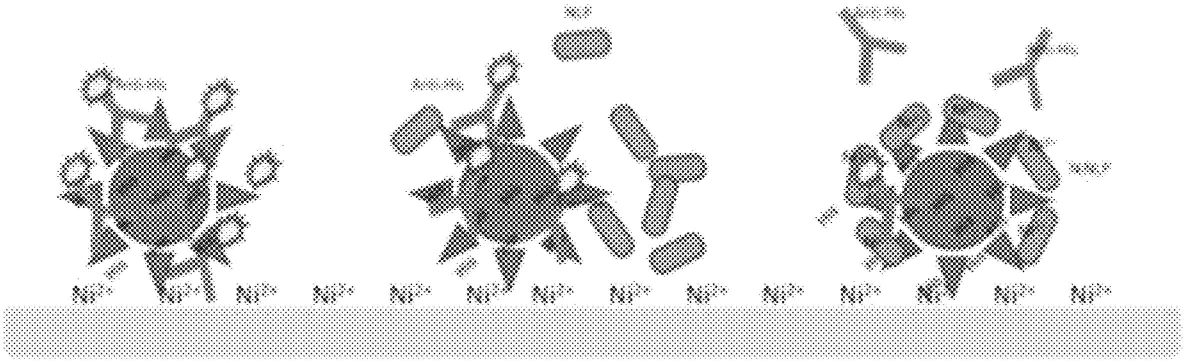
FIGS. 9A-9B depict a schematic diagram showing the inhibitory effect of Ni-NLP in an ELISA wherein Ni-NLP blocks the binding of anti-His antibody to $A_{24}$FMDV $P1_{6H}$. The gray platform with $Ni^{++}$ shows the plate surface coated with Ni-NTA. $A_{24}$FMDV $P1_{6H}$ is shown by a circular form. Anti His-antibody is shown as Y shapes and NiNLP as oval shape forms.
Figure 9B:
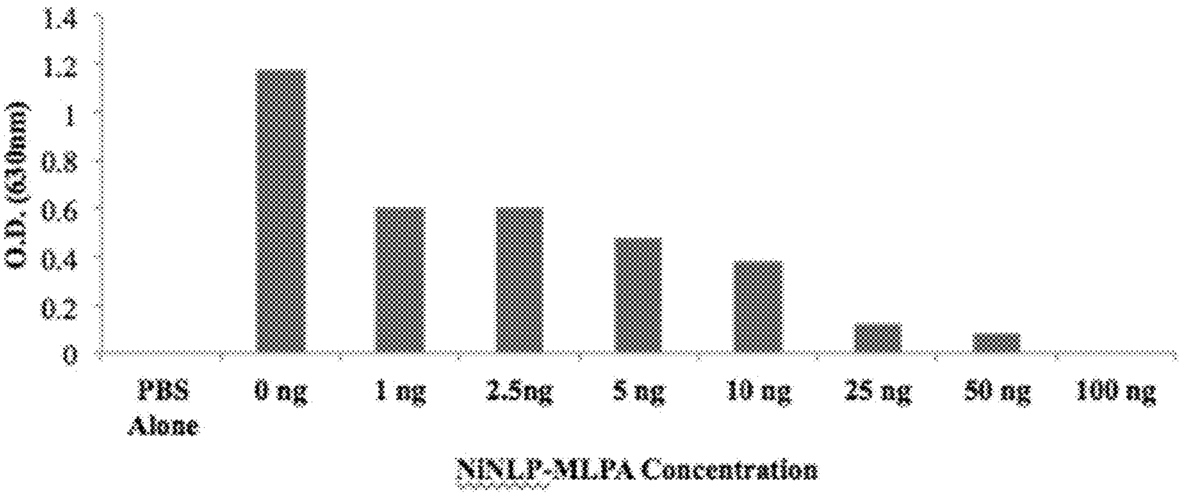

The binding of NiNLP-MPLA to mutant $A_{24}$-FMDV$2A_{6H}$ was determined by competitive ELISA. The interaction of FMDV $A_{24}$-6×-His with NiNLP-MPLA was determined by the interference to the binding of anti-6×-his antibody to FMDV A24-6×-his caused by Ni-NLP-MPLA. For this purpose, $A_{24}$ FMDV $2A_{6H}$ and $A_{24}$ FMDV $P1_{6H}$ corresponding to OD=1.0 at 630 nM were bound to the wells of Ni-NTA HisSorb Strips. After overnight binding at 4° C., the plate was washed three times with PBS and incubated with a series of concentrations of NiNLP-MPLA (1-100 ng). 0 ng Ni-NLP-MPLA was used as a control for no interference caused by NiNLP-MPLA; and the plate well coated with PBS, instead of virus, was used as negative control for reading the plate. After 45 min incubation at room temperature the plate washed three times with PBS and incubated with anti-6×-his (1:500 dilution) for 90 min at 37° C. The unbound antibody was washed by washing three times with PBS. The bound antibody was detected subsequently with 1:2000 dilution of secondary antibody (Goat anti-rabbit IgG h+l HRP conjugated, Bethyl Laboratories, Catalog No. A120-101P), as described above. The cartoon diagram displayed in FIG. 9A is a representation of the assay design. In this experiment, the extent to which NiNLP-MPLA could displace the mutant FMDV $A_{24}$ $P1_{6H}$ virus from binding to Ni-NTA plates (Qiagen) was determined. As shown in FIG. 9B, NiNLP effectively displaced His-tagged virus bound to the plate in a dose dependent manner. This observation further confirms that the binding of mutant FMDV $A_{24}$ $P1_{6H}$ plate is 6×-His tag specific.

Figure 10A:
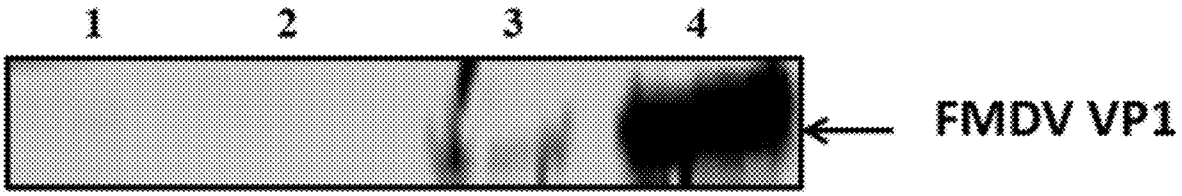
FIGS. 10A-10B show the binding of FMDV $A_{24}$ 6×-His FMD viruses to $Co^{+2}$-NTA beads.

Mock cell lysate or parental (WT)- or mutant 6×-His tagged FMDV $A_{24}$-infected cell lysates (previously clarified) were mixed with 100 μl of $Co^{2+}$-NTA resin [4] overnight at 4° C. with gentle rotation. After overnight incubation, the mixture was centrifuged at 760×g for 10 min. The supernatant was removed and the resin bound to proteins was washed with 50 mM Tris-HCl-500 mM NaCl pH 7.4 four times. The elution of bound protein was carried out using 300 mM imidazole-50 mM Tris-HCl-500 mM NaCl pH 7.4. The eluates were resolved on SDS-PAGE and transferred to nitrocellulose membrane. The protein bands were developed with 1:2000 Goat-anti rabbit VP1 (FIG. 10A). VP1-specific protein bands in western blot analysis of eluates from Co-bead bound viruses shows that the two 6×-His tagged FMDVs; $A_{24}$ FMDV $2A_{6H}$ (lane 3), $A_{24}$ FMDV $A_{24}$ $P1_{6H}$ (lane 4) bound specifically to the Co-NTA beads. FMDV $A_{24}$ Cruz WT- (lane 2) and Mock-infected (lane 1) cell lysates did not bind to the Co-NTA beads. This observation is very critical as it can be developed further and exploited for bulk purification of FMDV that will hugely help the production of large quantities of FMDV live attenuated vaccine.

Figure 10B:
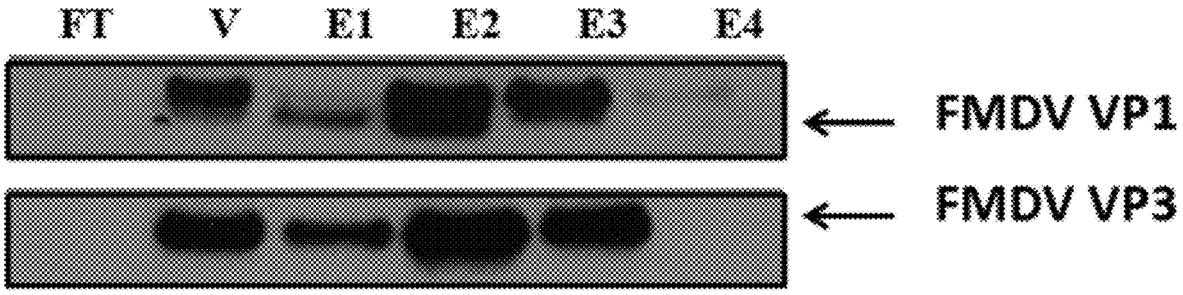

FIG. 10B depicts purification of FMDV $A_{24}$ 6×-His FMD virus using a Ni (HisTrap™ FF) column. Clarified infected cell lysate of $A_{24}$ FMDV $P1_{6H}$ virus was bound to a HisTrap™ FF crude 1 ml column, eluted with different concentrations of imidazole (100-500 mM). Crude lysates of virus (V) and different fractions from column purification (FT, E1-E4) were analyzed by western blotting for the presence of FMDV capsid proteins, VP1 and VP3. Lane FT denotes flow through fraction, lane V is initial crude virus before dialysis, and E1, E2, E3 and E4 are elution fractions 1, 2, 3 and 4 carried out with 100, 200, 300 and 500 mM imidazole, respectively. The VP1 and VP3 panels represent the protein bands recognized by FMDV $A_{24}$ VP1- and VP3-specific antibodies.

Example 5: Purification of Mutant 6×His-Tagged FMDV Capsids Using 6×His Affinity $Co^{2+}$-NTA Resin Columns The presence of surface-exposed 6×-His tags in mutant $A_{24}$ FMDV $2A_{6H}$ and $A_{24}$ FMDV $P1_{6H}$ viruses can potentially be exploited for one-step affinity purification ($Co^{++}$ or $Ni^{2+}$ affinity columns) and concentration of these viruses. After successful pull-downs of $A_{24}$ FMDV $P1_{6H}$ virus from crude cell lysates using $Co^{2+}$-NTA beads, it was attempted to purify intact virus particles from infected crude cell lysates using 6×His affinity $Co^{2+}$-NTA resin columns (G BIOSCIENCES). $Co^{2+}$-NTA resin 3 ml spin columns were washed with 5 column volume of milliQ water and equilibrated with 5 column volume of either, binding buffer (50 mM Tris-HCl, pH=7.5, 500 mM NaCl, 25 mM imidazole) for elution with imidazole or binding buffer (50 mM Tris-HCl, pH=7.5, 500 mM NaCl) for EDTA elution. 25 ml of clarified $A_{24}$ FMDV $P1_{6H}$-infected cell lysates were bound to the columns and the flow through (FT) were collected for further analysis. The columns were then washed with either 5 column volume of buffer A or B depending on the treatment and them the mutant FMDV particles were eluted with increasing concentrations of imidazole (E1=100 mM Imidazole, E2=200 mM Imidazole, E3=300 mM Imidazole, E4=500 mM Imidazole, respectively in 50 mM Tris-HCl, pH=7.5, 500 mM NaCl) or with EDTA (E1=10 mM EDTA, E2=25 mM EDTA, E3=50 mM EDTA, E4=100 mM EDTA, respectively in 50 mM Tris-HCl, pH=7.5, 500 mM NaCl. The elutions were carried out in 3 ml (1 column volume). An equivalent volume of the starting material (lysate prior column purification), unbound (FT) and different purified fractions were resolved by SDS-PAGE, transferred on to Nylon membrane and detected either by rabbit polyclonal anti-FMDV $A_{24}$ VP1 (1:2,500) or monoclonal antibody against FMDV $3D^{pol}$ (1:200). In parallel virus titers were determined by plaque assays as described above for initial and treated samples (before purification, FT and different elution samples).

Figure 11A:
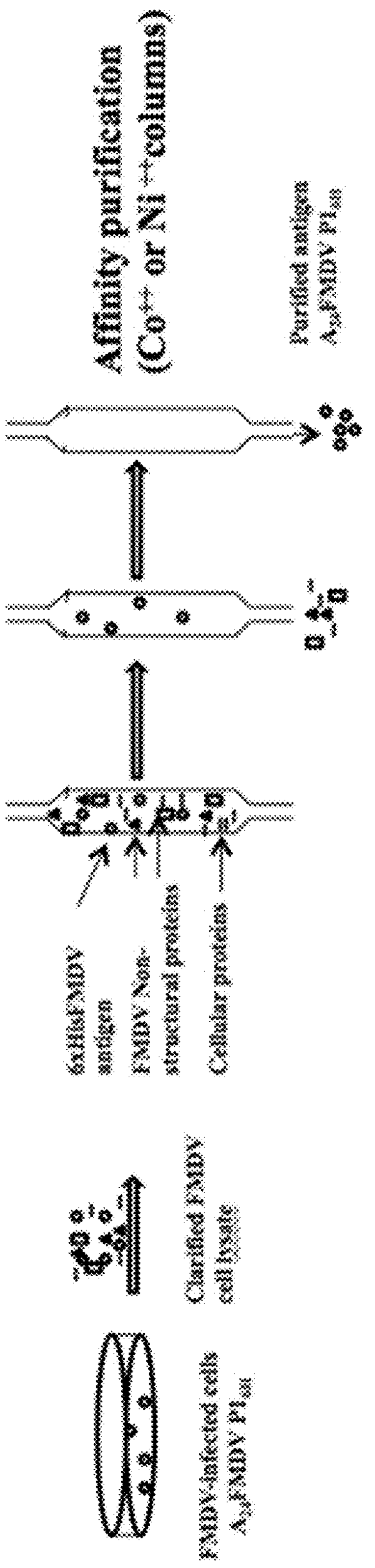
FIGS. 11A-11C depict $A_{24}$ FMDV $P1_{6H}$ virus purification by Co-NTA resin columns using two alternative elution methods.
Figure 11B:
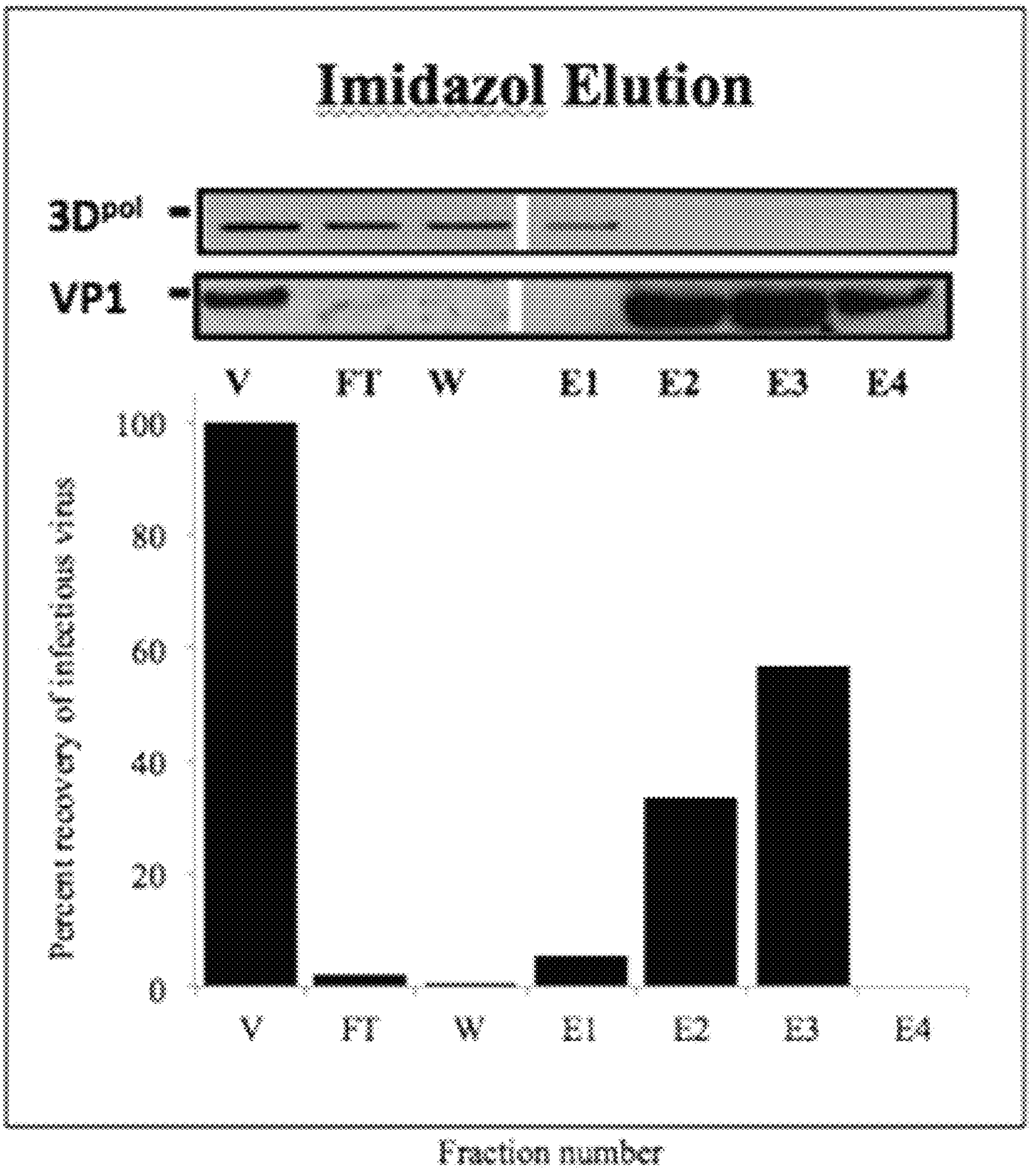
Figure 11C:
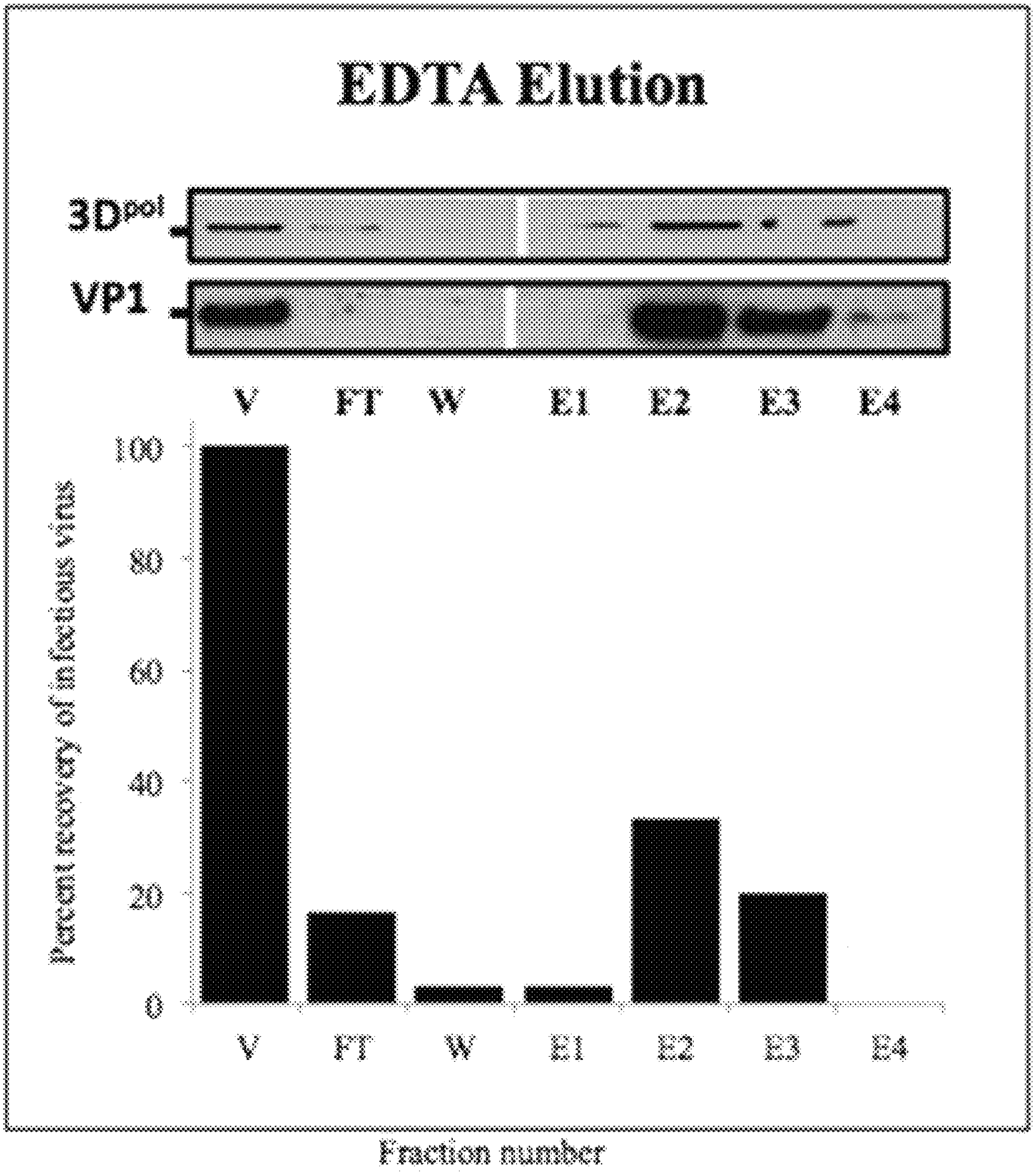

To determine the relative efficacy on recovery of infectious mutant virus and their protein contents (structural and non-structural proteins), fractions collected from pass through and eluates of $Co^{2+}$-NTA resin columns, were examined by virus plaque assays and Western Blot analysis. FIG. 11A displays a cartoon representation of the virus purification procedures that were followed. FIGS. 11B and 11C shows a side-by-side comparison of the two types of elution conditions tested: buffer containing imidazole or buffer containing EDTA. In eluates obtained using imidazole-based buffers (fractions labeled E1-E3), recovery of infectious virus was around 95% as compared to the initial material labeled "V" (FIG. 11B). In the case where elution was performed with increasing amounts of EDTA, lower virus titers, ~60% virus recovery in E1-E3, were recovered (FIG. 11C). Using Western Blot analysis (upper panel on FIGS. 11B and 11C), higher signals were observed for viral capsid protein VP1 at 100-300 mM (E1-E3) concentrations in the imidazole-based buffer, and at 10-50 mM EDTA-based buffer (E1-E3 in FIG. 11C). The presence of viral non-structural proteins, measured by the presence of $3D^{pol}$ in Western blots, showed that imidazole treatment produced purified 6×His mutant FMDV capsids in the absence of other viral proteins contaminants (FIGS. 11B and 11C, upper panel, sample labeled V). Under the EDTA-based buffer conditions tested (FIG. 11C), co-elution of 6×His tagged capsid FMDV along with non-structural proteins was detected. It is worth to note that since EDTA strips the metal off from the column, it is likely that any protein non-specifically bound to the column will also elute along with the target protein. Nonetheless, purification of $A_{24}$ FMDV $P1_{6H}$ with high efficiency highlights the achievement of the goal of one step purification of 6×His tagged FMDV using affinity column.

Example 6: $A_{24}$ FMDV Vaccine Formulated with a Commercially Available Adjuvant Proves Effective in a Mouse Model Animal experiments were performed in the high-containment facilities of the Plum Island Animal Disease Center, conducted in compliance with the Animal Welfare Act (AWA), the 2011 Guide for Care and Use of Laboratory Animals, 2002 PHS Policy for the Humane Care and Use of Laboratory Animals, and U.S. Government Principles for Utilization and Care of Vertebrates Animal Used in Testing, Research and Training (IRAC 1985), as well as an specific animal protocols reviewed and approved by the Institutional Animals Care and Use Committee (IACUC) of Plum Island Animal Disease Center (USDA/APHIS/AC Certificate number: 21-F-0001).

A FMD mouse model system has demonstrated that certain strains of adult mice, including C57BL/6, are susceptible to FMDV serotype C when infected subcutaneously (s.c.) in the footpad, developing a significant viremia and dying within a few days of infection. Furthermore, immunization with commercial vaccine protected the animals against homologous challenge with FMDV serotype C. Diaz San-Segundo et al. [43] confirmed that the model is an efficient tool for other FMDV serotypes more relevant in the field. C57BL/6 female mice, 6-7 weeks old, were purchased from Jackson Laboratories (Bar Harbor, Me.) and were acclimated for one week. Groups of 6 C57BL/6 mice were intraperitoneally (i.p.) vaccinated with different formulations of BEI-inactivated FMDV A24 vaccine as indicated in Table 4. Seven days after vaccination, animals were challenged with a lethal dose ($1\times10^5$ pfu) of FMDV serotype $A_{24}$ [43]. To perform the challenge, animals were anesthetized with isofluorane (Webster Veterinary, Devens, Mass.) and immediately infected subcutaneously (s.c.) in the left/right rear footpad with $10^5$ pfu FMDV $A_{24}$ WT in 50 ul. Animals were monitored for 8 days and blood taken at 0 days and on alternate days for the first seven days after challenge and then weekly until the end of the experiment.

TABLE 4

Experimental design of $A_{24}$Cru BEI-inactivated vaccine in mice.

| Animal # | Vaccination | Dose | Challenge (time) | Challenge (dose) |
|---|---|---|---|---|
| R15-1-R15-6 | Inactive FMDV A24[a] | 0.025 μg | 7dpv[b] | 1 × $10^5$ pfu[c] A24[d] |
| R15-7-R15-12 | Inactive FMDV A24 | 0.05 μg | 7dpv | 1 × $10^5$ pfu A24 |
| R15-13-R15-18 | Inactive FMDV A24 | 0.1 μg | 7dpv | 1 × $10^5$ pfu A24 |
| R15-19-R15-24 | Inactive FMDV A24 + ISA206 | 0.025 μg | 7dpv | 1 × $10^5$ pfu A24 |
| R15-25-R15-30 | Inactive FMDV A24 + ISA206 | 0.05 μg | 7dpv | 1 × $10^5$ pfu A24 |
| R15-31-R15-36 | Inactive FMDV A24 + ISA206 | 0.1 μg | 7dpv | 1 × $10^5$ pfu A24 |
| R15-37-R15-42 | PBS | — | 7dpv | 1 × $10^5$ pfu A24 |

[a]Intraperitoneal inoculation (200 μl/mouse)
[b]Days postvaccination
[c]Plaque forming units
[d]Challenge subcutaneous in rear foot-pad (50 μl/mouse)

Figure 12A:
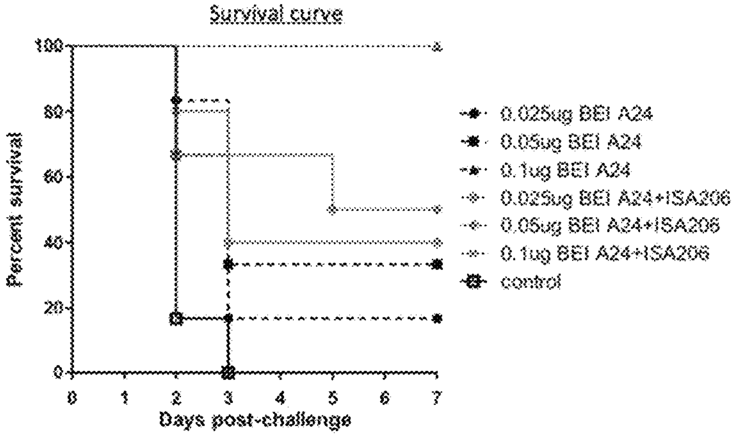
FIGS. 12A-12C The efficacy of BEI inactivated $A_{24}$ FMDV WT vaccine formulated with a commercially available adjuvant against $A_{24}$ FMDV WT challenge was evaluated in a mouse model.
Figure 12B:
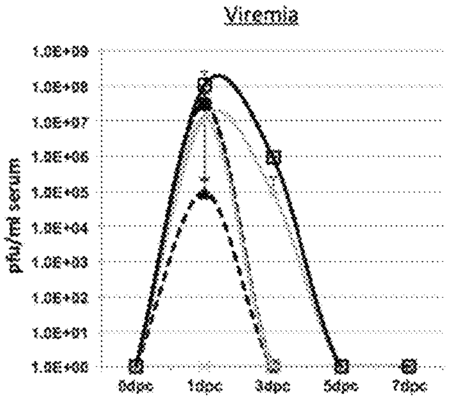

To confirm that commercial vaccine can protect C57BL/6 mice against FMDV serotype A, groups of 6 mice each were vaccinated with different doses of BEI-inactivated FMDV serotype A formulated with or without adjuvant Montanide ISA206 (Seppic Inc.) (Table 4). Seven days after vaccination, animals were challenged with a lethal dose of FMDV serotype $A_{24}$ and disease was followed for 7dpc. As previously described, all control animals died in two or three days after challenge (FIG. 12A), and developed high levels of viremia (over $1\times10^8$ pfu/ml of serum (FIG. 12B). All animals inoculated with the highest dose of vaccine (0.1 ug) with or without adjuvant were protected (FIG. 12A). Animals inoculated with vaccine plus adjuvant did not show any viremia; whereas, animals inoculated with 0.1 ug of inactivated vaccine without adjuvant showed a mild viremia ($10^5$ pfu) (FIG. 12B). Lower vaccine doses (0.05 or 0.025 ug) resulted in lower survival, with the correlation, that the lower the vaccine, the fewer animals survived the challenge. As expected, vaccine formulated with the adjuvant conferred better protection than inactivated virus alone (FIG. 12A).

Figure 12C:
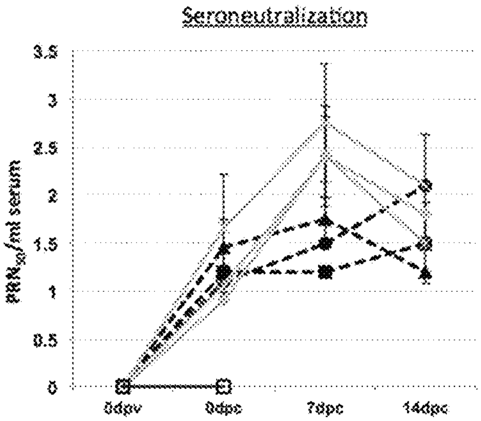

To understand the nature of protection observed in these animals, the humoral immune response induced by the different doses and formulations of inactivated vaccines was analyzed. As observed in FIG. 12C, at the moment of challenge (7dpv=0dpc), there were no statistically significant differences in the levels of neutralizing antibodies in all vaccinated groups. However, after the challenge, animals vaccinated with inactivated vaccine plus adjuvant showed a stronger response than the groups vaccinated with inactivated virus without adjuvant. The groups vaccinated with the highest dose of vaccine were the ones with the highest levels of neutralizing antibodies.

Example 7: Formulation of BEI-Inactivated $A_{24}$ FMDV $P1_6$ with NiNLP-MPLA Improves Protection In Vivo Once the mouse model was established to be successful for the BEI-inactivated $A_{24}$ Cru vaccine, it was used to test other FMD vaccine candidates against lethal challenge. A new experiment was performed to test efficacy of 6×-His tags $A_{24}$ FMDV $P1_{6H}$ mutant virus combined with NiNLP-MPLA nanoconstructs. Different concentrations (doses) of BEI-inactivated FMDV $A_{24}$ FMDV $P1_{6H}$ were tested, formulated with or without NLPs. Two control groups were included, one to test the effect of the NiNLP-MPLA alone in FMDV lethal challenge and another control group inoculated with PBS (Table 5).

TABLE 5

Experimental design: $A_{24}$-His tagged BEI-inactivated vaccine with NPLs in mice

| Animal # | Vaccination | Dose | Challenge (time) | Challenge (dose) |
|---|---|---|---|---|
| R15-117-R15-122 | Inactive FMDV A24-His[a] | 0.01 μg | 7dpv[b] | 1 × $10^5$ pfu[c] A24[d] |
| R15-99-R15-104 | Inactive FMDV A24-His | 0.025 μg | 7dpv | 1 × $10^5$ pfu A24 |
| R15-49-R15-54 | Inactive FMDV A24-His | 0.05 μg | 7dpv | 1 × $10^5$ pfu A24 |
| R15-55-R15-60 | Inactive FMDV A24-His | 0.1 μg | 7dpv | 1 × $10^5$ pfu A24 |
| R15-132-R15-128 | Inactive FMDV A24-His + NiNLP-MPLA | 0.01 μg | 7dpv | 1 × $10^5$ pfu A24 |
| R15-105-R15-110 | Inactive FMDV A24-His + NiNLP-MPLA | 0.025 μg | 7dpv | 1 × $10^5$ pfu A24 |
| R15-67-R15-72 | Inactive FMDV A24-His + NiNLP-MPLA | 0.05 μg | 7dpv | 1 × $10^5$ pfu A24 |
| R15-73-R15-78 | Inactive FMDV A24-His + NiNLP-MPLA | 0.1 μg | 7dpv | 1 × $10^5$ pfu A24 |
| R15-79-R15-84 | NiNLP-MPLA alone | 0.5 μg | 7dpv | 1 × $10^5$ pfu A24 |
| R15-129-R15-134 | PBS | — | 7dpv | 1 × $10^5$ pfu A24 |

[a]Intraperitoneal inoculation (200 μl/mouse)
[b]Days postvaccination
[c]Plaque forming units
[d]Challenge subcutaneous in rear foot-pad (50 μl/mouse)

Figure 13A:
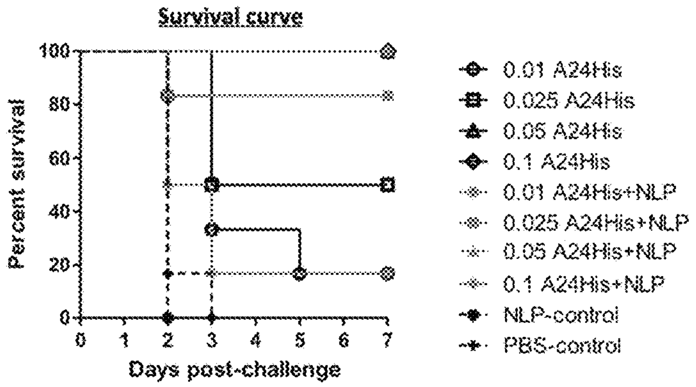
FIGS. 13A-13D show that chemically inactivated $A_{24}$FMDV $P1_{6H}$ formulated with NiNLP-MPLA improves protection against lethal challenge. 6 to 7 weeks old female C57BL/6 mice (n=6/group) were vaccinated by intraperitoneal (i.p.) injections with indicated amounts of inactivated mutant $A_{24}$FMDV $P1_{6H}$ virus with or without NiNLP-MPLA. Seven days after vaccination, animals were challenged by subcutaneous (s.c.) injection in the footpad with a lethal dose of homologous FMDV $A_{24}$Cru. Survival rates (FIG. 13A), and viremia (FIG. 13B) expressed as plaque forming units per ml of serum (pfu·ml), were followed for 7 days post challenge (dpc). Two control groups were included: one group of animals inoculated with NLP and a second group injected with phosphate-buffered saline (PBS) (n=6).
Figure 13B:
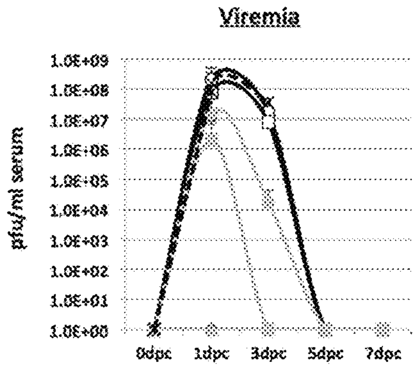

After challenge at 7dpv, all animals in the two control groups died within 48-72 hours after the challenge (FIG. 13A), indicating that the NiNLP-MPLA nanoconstructs did not interfere with the regular course of disease in mice. Furthermore, levels of viremia in the animals of both control groups are the same (FIG. 13B). All vaccinated animals with 0.1 or 0.05 ug of vaccine either formulated with or without NiNLP-MPLA survived the challenge (FIG. 13A). However, with lower doses of vaccine, there is a significant difference between animals inoculated with inactivated virus alone or in combination with NiNLP-MPLA. In particular, the survival rate in mice inoculated with BEI $A_{24}$ FMDV $P1_{6H}$ virus alone was 50% and when formulated with the NiNLP-MPLA adjuvant, the survival rate increased to 80% (FIG. 13A). Furthermore, the levels of viremia of animals inoculated with 0.025 ug of BEI-inactivated mutant virus with adjuvant NiNLP-MPLA was almost two logs lower that the mice inoculated with same dose of vaccine without NiNLPs (FIG. 13B), indicating that the addition of NiNLP-MPLA in the vaccine formulation improves protection against challenge with homologous FMDV $A_{24}$. Levels of neutralizing antibodies in vaccinated animals developed by 7 dpv and increased after challenge (7dpv). Interestingly, when levels of antibodies were compared in the mice group receiving 0.025 ug of BEI-inactivated vaccine with or without NLPs, it was observed that there was a statistically significant difference ($P<0.05$) between the two groups. Furthermore, although no statistically significant differences were observed among the groups inoculated with higher doses of vaccine (0.05 or 0.1 ug) with or without NiNLPs, it was observed that there is a tendency for animals immunized with the inactivated vaccine combined with NiNLP-MPLA to show higher levels of antibodies after the challenge.

Figure 13C:
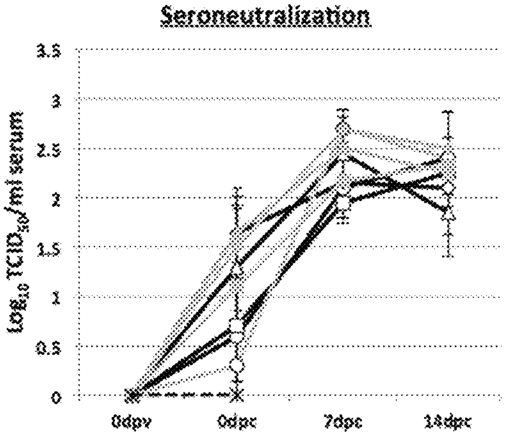
Figure 13D:
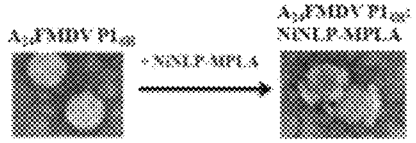

The vaccinated animals developed neutralizing antibodies at 7 dpv, and as expected a boost in the antibody titers was observed after virus challenge. Antibody titers in the group receiving 0.025 mg of BEI inactivated vaccine with NLPs, was significantly higher than those without NLPs ($P<0.05$) (FIG. 13C). In EM image, the complex formed between A24 FMDVP16H and MPLA:NiNLP in the vaccine prep used in this experiment is shown in FIG. 13D.

Example 8: Differentiation of Animals Vaccinated with 6×-His Tag Mutant Virus from Animals Infected with Parental A24Cru Virus To study the immune response to the 6×His tag in animals, sera collected from mice following aerosol inoculation with live $A_{24}$ FMDV WT (mice IDs 6.1, 6.2, 6.3, 6.4 SER pooled together) and $A_{24}$ FMDV $P1_{6H}$ (mice IDs R15-74, 75, 76, 77, 78 pooled together) were examined in an indirect sandwich ELISA (IS-ELISA) performed with modifications to the protocol specified by WHO (World Organization for Animal Health. In: *Manual of Diagnostic Tests and Vaccines for Terrestrial Animals.* 2012. OIE, Paris, France, Chapter 2.1.5. Foot and Mouth Disease). Briefly, 6×-His tagged recombinant human poly(rC) binding protein 2 (PCBP-2) was diluted in PBS to obtain 5 ng and 10 ng/μl concentrations that were bound to pre-blocked Nickel coated plates (Ni-NTA HisSorb Strips, Qiagen, Catalog No. 35023). After overnight incubation at 4°, the plates were washed four times with PBS. 1 hr blocking was performed at 37° C. with 1% bovine serum albumin (BSA) in PBS. 40 μl of test sera/well (1/6 in PBS) were applied to the plates, followed by incubation at 37° C. for 2 h. After four washes, 100 μl of peroxidase labeled goat antibody to mouse-IgG (H+L) (KPL)/well diluted 1:5,000 in (1% BSA in PBS) was added, followed by incubation for 1 h at 37° C. After four additional washes, the antigen-antibody complexes were detected by the addition of 100 μl/well of SureBlue Reserve (KPL) and stopped in 5 min with 100 μl of TMB BlueSTOP solution (KPL)/well. The optical density (OD) was determined at 630 nm on an automated ELISA plate reader.

Figure 14:
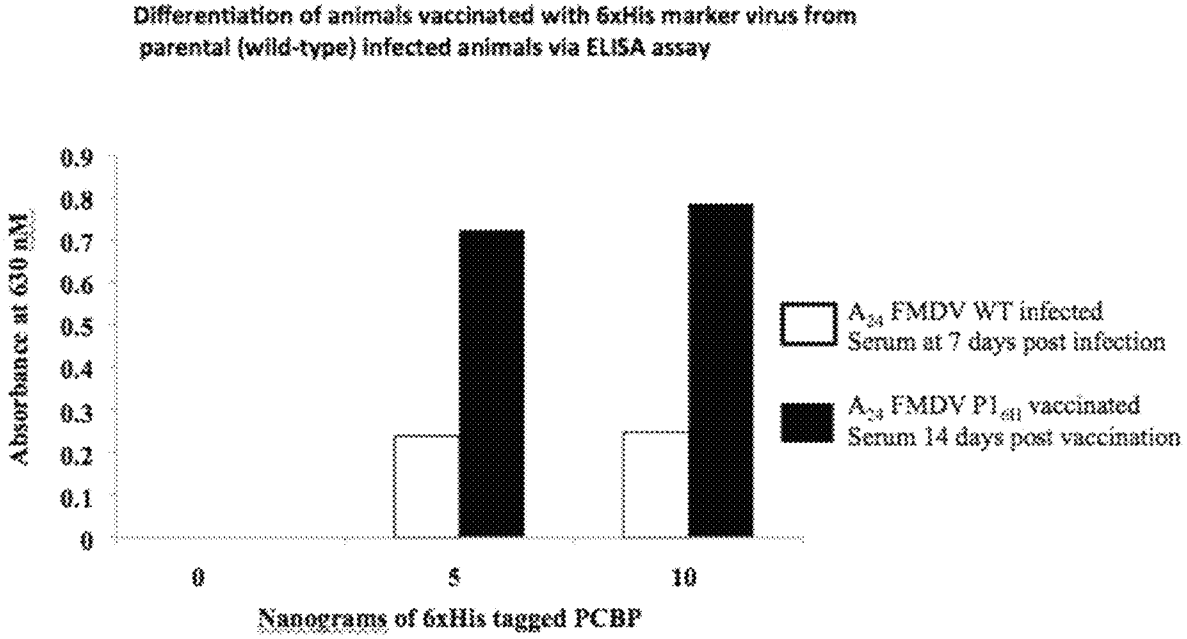
FIG. 14 depicts the differentiation of animals vaccinated with the 6×-His tag mutant virus $A_{24}$ FMDV $P1_{6H}$ from animals infected with the parental $A_{24}$Cru virus using an indirect ELISA assay. 6×-His tagged recombinant human poly (rC) binding protein 2 (PCBP-2), bound to Ni-coated plates, was utilized in an indirect sandwich ELISA (IS-ELISA) assay to differentiate serum of $A_{24}$ FMDV WT-infected mice from serum of $A_{24}$ FMDV $P1_{6H}$-infected mice. X-axis values denote the concentration of the PCBP-2 coated on the plate. The Y-axis values denote the O.D. at 630 nM and reflect the amount of anti-Histidine antibody present in a particular serum pool. White bars represent the serum from $A_{24}$ FMDV WT-infected animals and black bars represent the serum from animals vaccinated with $A_{24}$ FMDV $P1_{6H}$.

FIG. 14 shows the result from the IS-ELISA assay performed to distinguish the antibody response of animals infected with $A_{24}$ FMDV WT from $A_{24}$ FMDV $P1_{6H}$ vaccinated animals. The sharp difference in the optical densities of $A_{24}$ FMDV WT and $A_{24}$ FMDV $P1_{6H}$ in both the 5 ng and 10 ng PCBP-2 coated wells provides evidence for a diagnostic assay to distinguish the two groups indicating that the assay can be used for differentiation of the marker vaccine-immunized animals from those animals naturally infected with pathogenic FMDV.

Figure 15A:
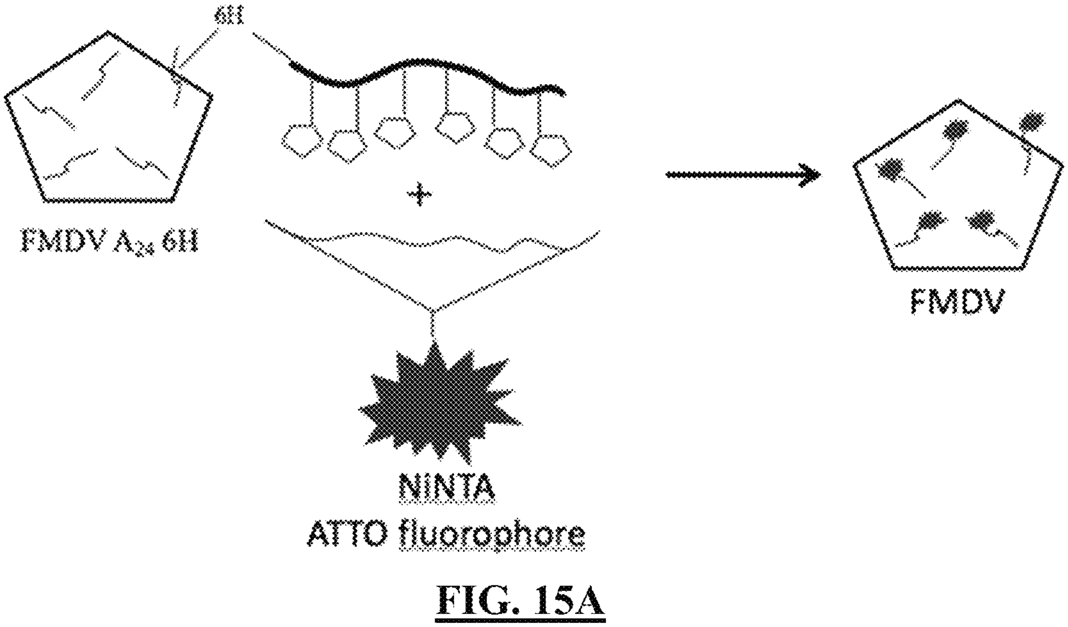
FIG. 15A shows a schematic of the mechanism of interaction between 6×-His-tagged FMDV and a NiNTA ATTO-550 fluorophore. FMDV is shown as pentagonal structure to depict the 12s or pentameric unit of FMDV. 6×-His tag (6H) is shown on the surface of the pentamer. Due to Histidine-NiNTA binding, the virus gets labelled with the NiNTA ATTO-500 fluorophore.
Figure 15B:
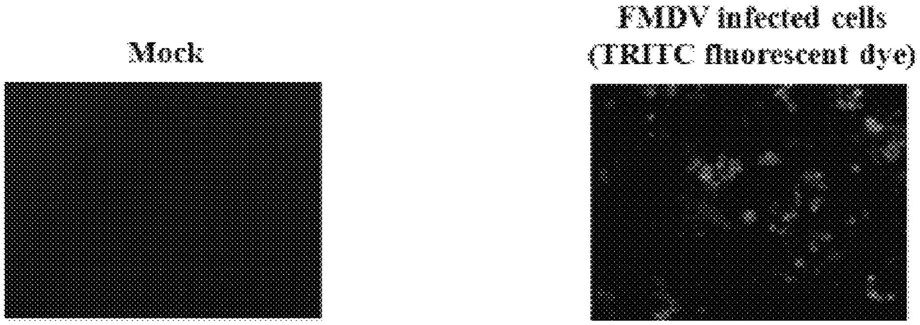
FIG. 15B shows in the lower left panel mock-infected cells showing no fluorescence. In contrast, in the lower right panel, the FMDV 6×-His infected cells show red fluorescence (shown as white spots in the dark background in FIG. 15B) associated with binding of the NiNTA ATTO-500 fluorophore.

Example 9: Live Imaging of 6×-His-Tagged FMDV with Small Fluorescent Chromophore Molecules In addition to easy one step purification and vaccine formulations consisting of Ni-doped nanolipoprotein and adjuvant, and other similar His-tag-specific formulations as described in the Examples above, chemical labeling of His-tagged virus utilizing fluorescent molecules is an attractive technique for detection of virus movement inside infected culture cells via affinity labeling (FIG. 15). Small fluorescent molecules such as NiNTA-ATTO-550 conjugate (FIG. 15A) or alternatively Ni-NTA-Cy3 or Ni-NTA-Cy5 (https://www.aatbio.com/products/his-lite-cy3-bis-nta-ni-complex) allows rapid visualization of the 6×-His mutant virus dynamics inside a cell and to provide new insight into FMDV and related virus replication. In fact, this technology (Ni-NTA-His interaction) can be extended to the detection of FMDV capsid protein interaction with other viral and cellular proteins and nucleic acid in vitro using fluorescent plate based assays and gel-electrophoretic detection. This in vitro assay can provide valuable tools to study FMDV capsid binding to small molecules or receptors. FIG. 15B shows cultured BHK-21 cells infected with FMDV A24 $P1_{6H}$ at a multiplicity of infection of 10 and incubated at 37° C. for 4 h.

In summary, provided herein are genetically engineered Foot and Mouth Disease Viruses (FMDV) modified by the strategic insertion of engineered Foot and Mouth Disease Virus (FMDV) and related engineered proteins and polynucleotides, nanolipoprotein particles, compositions, methods and systems. the genetically engineered FMDV modified by the strategic insertion of a protein tag into select regions of the FMDV genome which encode viral proteins that are exposed on the surface of the FMDV viral capsid. The inserted protein tag is displayed as a decoration or attachment on the viral capsid surface. In particular, the protein tag can be a HIS tag, two 6×his-marked mutant viruses $A_{24}$FMDV $2A_{6H}$ and $A_{24}$FMDV $P1_{6H}$ exemplify the modified viral capsids. The particular placement of the 6×-His-tag insertions enables new effective vaccine formulations, purification protocols through histidine binding of divalent cations and anti-histidine antibody recognition protocols. The design of these 6×his-mutant viruses allows the exchange of cassettes representing relevant capsid coding regions of other FMDV strains/serotypes/and subtypes of FMDV field isolates.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified NLPs and related uses to additional NLPs formed by other membrane forming lipids, polymerizable lipids scaffold proteins and possibly functionalized amphipathic compounds and membrane proteins according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P1945-US-Seq-List-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Mason, P. W., M. J. Grubman, and B. Baxt, *Molecular basis of pathogenesis of FMDV*. Virus research, 2003. 91(1): p. 9-32.
2. Rai, D. K., et al., *Novel 6×His tagged foot-and-mouth disease virus vaccine bound to nanolipoprotein adjuvant via metal ions provides antigenic distinction and effective protective immunity*. Virology, 2016. 495: p. 136-147.
3. Rieder, E., et al., *Analysis of a foot-and-mouth disease virus type A24 isolate containing an SGD receptor recognition site in vitro and its pathogenesis in cattle*. Journal of virology, 2005. 79(20): p. 12989-12998.
4. Shaw, D., et al., *Female genital cosmetic surgery*. Journal of Obstetrics and Gynaecology Canada, 2013. 35(12): p. 1108-1112.
5. Grubman, M. J. and B. Baxt, Foot-and-mouth disease. Clinical microbiology reviews, 2004. 17(2): p. 465-493.
6. Rodriguez, L. L. and C. G. Gay, *Development of vaccines toward the global control and eradication of foot-and-mouth disease*. Expert review of vaccines, 2011. 10(3): p. 377-387.
7. Smith, M. T., et al., *Foot-and-mouth disease: technical and political challenges to eradication*. Vaccine, 2014. 32(31): p. 3902-3908.
8. Caspar, D. L. and A. Klug. *Physical principles in the construction of regular viruses*. in *Cold Spring Harbor symposia on quantitative biology*. 1962. Cold Spring Harbor Laboratory Press.
9. Lawrence, P., et al., *Foot-and-mouth disease virus (FMDV) with a stable FLAG epitope in the VP1 GH loop as a new tool for studying FMDV pathogenesis*. Virology, 2013. 436(1): p. 150-161.
10. Seago, J., et al., *Characterization of epitope-tagged foot-and-mouth disease virus*. Journal of General Virology, 2012. 93(11): p. 2371-2381.
11. Seago, J., et al., *An infectious recombinant foot-and-mouth disease virus expressing a fluorescent marker protein*. Journal of General Virology, 2013. 94(7): p. 1517-1527.
12. Acharya, R., et al., *The three-dimensional structure of foot-and-mouth disease virus at 2.9 Å resolution*. 1989.
13. Fowler, V., et al., *Chimeric foot-and-mouth disease viruses: evaluation of their efficacy as potential marker vaccines in cattle*. Vaccine, 2008. 26(16): p. 1982-1989.
14. Ryan, M. D., A. M. King, and G. P. Thomas, *Cleavage of foot-and-mouth disease virus polyprotein is mediated by residues located within a 19 amino acid sequence*. Journal of General Virology, 1991. 72(11): p. 2727-2732.
15. Dawson, P. E., et al., *Synthesis of proteins by native chemical ligation*. Science, 1994. 266(5186): p. 776-780.
16. Nilsson, B. L., M. B. Soellner, and R. T. Raines, *Chemical synthesis of proteins*. Annu. Rev. Biophys. Biomol. Struct., 2005. 34: p. 91-118.
17. Zordan, R. E., et al., *Avoiding the ends: internal epitope tagging of proteins using transposon Tn7*. Genetics, 2015. 200(1): p. 47-58.
18. Logan, D., et al., *Structure of a major immunogenic site on foot-and-mouth disease virus*. Nature, 1993. 362 (6420): p. 566.
19. Biswal, J. K., et al., *Engineering foot-and-mouth disease virus serotype O IND R2/1975 for one-step purification by immobilized metal affinity chromatography*. Biologicals, 2015. 43(5): p. 390-398.
20. Yang, B., et al., *The rescue and evaluation of FLAG and HIS epitope-tagged Asia 1 type foot-and-mouth disease viruses*. Virus research, 2016. 213: p. 246-254.
21. Gullberg, M., et al., *Processing of the VP1/2A junction is not necessary for production of foot-and-mouth disease virus empty capsids and infectious viruses: characterization of "self-tagged" particles*. Journal of virology, 2013. 87(21): p. 11591-11603.
22. Fischer, N. O., et al., *Colocalized delivery of adjuvant and antigen using nanolipoprotein particles enhances the immune response to recombinant antigens*. Journal of the American Chemical Society, 2013. 135(6): p. 2044-2047.
23. Sambrook, J., E. Fritsch, and T. Maniatis, *Molecular cloning: a laboratory manual, 2nd edn. Cold Spring Laboratory Press*. New York, 1989.
24. Innis, M. A., D. H. Gelfand, and J. J. Sninsky, PCR strategies. 1995: Academic Press.
25. Fry, E., et al., *Architecture and topography of an aphthovirus*. Semin. Virol, 1990. 1: p. 439-451.
26. Hames, B. D. and S. J. Higgins, *Nucleic acid hybridisation: a practical approach*. 1985.
27. Myers, E. W. and W. Miller, *Optimal alignments in linear space*. Computer applications in the biosciences: CABIOS, 1988. 4(1): p. 11-17.
28. Smith, T. F. and M. S. Waterman, *Comparison of biosequences*. Advances in applied mathematics, 1981. 2(4): p. 482-489.
29. Needleman, S. B. and C. D. Wunsch, *A general method applicable to the search for similarities in the amino acid sequence of two proteins*. Journal of molecular biology, 1970. 48(3): p. 443-453.
30. Pearson, W. R. and D. J. Lipman, *Improved tools for biological sequence comparison*. Proceedings of the National Academy of Sciences, 1988. 85(8): p. 2444-2448.
31. Karlin, S. and S. F. Altschul, *Methods for assessing the statistical significance of molecular sequence features by using general scoring schemes*. Proceedings of the National Academy of Sciences, 1990. 87(6): p. 2264-2268.
32. Karlin, S. and S. F. Altschul, *Applications and statistics for multiple high-scoring segments in molecular sequences*. Proceedings of the National Academy of Sciences, 1993. 90(12): p. 5873-5877.
33. Zuker, M., *Mfold web server for nucleic acid folding and hybridization prediction*. Nucleic acids research, 2003. 31(13): p. 3406-3415.
34. Rieder, E., et al., *Genetically engineered foot-and-mouth disease viruses with poly (C) tracts of two nucleotides are virulent in mice*. Journal of virology, 1993. 67(9): p. 5139-5145.
35. Uddowla, S., et al., *A safe foot-and-mouth disease vaccine platform with two negative markers for differentiating infected from vaccinated animals*. Journal of virology, 2012. 86(21): p. 11675-11685.

36. Bader, H., et al., *Polymeric monolayers and liposomes as models for biomembranes*. Polymer Membranes, 1985: p. 1-62.
37. Blanchette, C. D., et al., *Kinetic analysis of his-tagged protein binding to nickel-chelating nanolipoprotein particles*. Bioconjugate chemistry, 2010. 21(7): p. 1321-1330.
38. Blanchette, C. D., et al., *Characterization and purification of polydisperse reconstituted lipoproteins and nanolipoprotein particles*. International journal of molecular sciences, 2009. 10(7): p. 2958-2971.
39. Bundy, B. C., M. J. Franciszkowicz, and J. R. Swartz, *Escherichia coli-based cell free synthesis of virus-like particles*. Biotechnology and bioengineering, 2008. 100 (1): p. 28-37.
40. Pacheco, J. M., et al., *Rapid protection of cattle from direct challenge with foot-and-mouth disease virus (FMDV) by a single inoculation with an adenovirus-vectored FMDV subunit vaccine*. Virology, 2005. 337(2): p. 205-209.
41. Domb, A., et al., *Degradable polymers for site-specific drug delivery*. Polymers for Advanced Technologies, 1992. 3(6): p. 279-292.
42. Chasin, M., *Biodegradable polymers as drug delivery systems*. Vol. 45. 1990: Informa Health Care.
43. Diaz-San Segundo, F., et al., *Venezuelan equine encephalitis replicon particles can induce rapid protection against foot-and-mouth disease virus*. Journal of virology, 2013: p. JVI. 03462-12.

The invention claimed is:

1. A vaccine comprising (i) one or more genetically modified Foot and Mouth Disease Virus (FMDV) having a viral capsid comprising a protein tag up to 100 amino acids inserted in an engineered FMDV VP1 protein and presented on an external surface of the viral capsid, and/or (ii) one or more FMD functionalized nanolipoprotein particle comprising a scaffold protein and a functionalized membrane forming lipid presenting a tag substrate attached to the protein tag presented on the external surface of the viral capsid of the one or more genetically modified FMDV, together with (iii) a pharmaceutically acceptable vehicle, wherein the protein tag is inserted in the engineered FDMV VP1 protein at an insertion position selected from any one of position −1 to position +6 relative to an FMDV 2A N-terminus of the engineered FDMV VP1 protein, and any one of position −1 to position −7 relative to an FMD VP1 C-terminus of the engineered FDMV VP1 protein.

2. The vaccine of claim 1, wherein the protein tag is from 1 to 20 amino acids in length.

3. The vaccine of claim 1, wherein the protein tag comprises a peptide tag selected from the group consisting of AviTag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, and SnoopTag.

4. The vaccine of claim 1, wherein the protein tag is a polyhistidine tag.

5. The vaccine of claim 4, wherein the sequence of the polyhistidine tag is HHHHHHKQ (SEQ ID NO:16) or HHHHHHIIAPAK (SEQ ID NO:17).

6. The vaccine of claim 1, wherein the insertion position is selected from any one of position −1 to position −4 relative to the FMD VP1 C-terminus.

7. The vaccine of claim 1, wherein the insertion position is −1 relative to the FMD VP1 C-terminus.

8. The vaccine of claim 1, wherein the genetically modified FMDV is encoded by a polynucleotide having sequence SEQ ID NO: 3.

9. The vaccine of claim 1, wherein the tag substrate is a molecule chelating a bivalent metal ion and the protein tag is a polyhistidine molecule.

10. The vaccine of claim 1, wherein the tag substrate is a negatively charged moiety and the protein tag is a polyarginine molecule.

11. The vaccine of claim 1, wherein the tag substrate is avidin or a derivative thereof and the protein tag is selected from the group consisting of Avi-Tag, SBP-tag and Strep-tag.

12. The vaccine of claim 1, wherein the functionalized membrane forming lipid is a biological molecule.

13. The vaccine of claim 1, wherein the FMDV functionalized nanolipoprotein particle further comprises a membrane forming lipid.

14. The vaccine of claim 1, wherein the scaffold protein is an apolipoprotein.

15. The vaccine of claim 1, wherein the FMDV functionalized nanolipoprotein particle further comprises one or more adjuvants attached to a tag substrate presented on the functionalized nanolipoprotein surface.

16. The vaccine of claim 15, wherein the one or more adjuvants are selected from the group consisting of f-Met-Leu-Phe, muramyl dipeptide, saponins, toxins, oligonucleotide CpG motifs, immunostimulatory carbohydrates, immunostimulatory polysaccharides, cytokines, chemokines and derivatives thereof.

17. The vaccine of claim 1, wherein the FMDV functionalized nanolipoprotein particle further comprises one or more adjuvants selected from the group consisting of hydrophobic adjuvants, amphipathic adjuvants, hydrophilic adjuvants synthetically appended with a hydrophobic moiety.

18. The vaccine of claim 1, wherein the FMDV functionalized nanolipoprotein particle further comprises at least one amphipathic adjuvant selected from the group consisting of mono-phosphorylated Lipid A, lipopolysaccharides, squalene, sorbitol oleate esters, alpha-galactosyl ceramide, lipotichoic acid and saponins.

19. The vaccine of claim 18, wherein the at least one amphipathic adjuvant are multiple amphipathic adjuvants.

20. The vaccine of claim 1, wherein the vaccine further comprises one or more additional immunomodulatory components.

21. The vaccine of claim 20, wherein the immunomodulatory component is an adjuvant or a cytokine.

22. The vaccine of claim 1, wherein the FMDV is in a chemically inactivated form.

23. A method to treat or prevent FMD in a cloven-hoofed animal, the method comprising administering to the cloven-hoofed animal an effective amount of the vaccine of claim 1.

24. The method of claim 23, wherein the vaccine comprises a chemically-inactivated genetically engineered marker FMDV in an effective amount to delay onset or severity of FMD in the cloven-hoofed animal.

25. The method of claim 23, wherein the vaccine comprises a chemically-inactivated genetically engineered marker FMDV in an effective amount to protect the cloven-hoofed animal against FMD.

26. The method of claim 23, wherein the effective amount comprises from about $10^2$ to about $10^8$ pfu of the one or more genetically modified FMDV alone or in combination with one or more FMD functionalized nanolipoprotein particle.

27. The method of claim 23, wherein the effective amount comprises from about $10^3$ to about $10^7$ pfu of the one or more genetically modified FMDV alone or in combination with one or more FMD functionalized nanolipoprotein particle.

* * * * *